US010457736B2

(12) United States Patent
Finlay

(10) Patent No.: US 10,457,736 B2
(45) Date of Patent: Oct. 29, 2019

(54) BINDING AGENTS

(71) Applicant: ULTRAHUMAN ONE LIMITED, Sandwich (GB)

(72) Inventor: William James Jonathan Finlay, Sandwich (GB)

(73) Assignee: ULTRAHUMAN ONE LIMITED, Sandwich (GB)

( * ) Notice: Subject to any disclaimer, the term of this patent is extended or adjusted under 35 U.S.C. 154(b) by 36 days.

(21) Appl. No.: 16/104,434

(22) Filed: Aug. 17, 2018

(65) Prior Publication Data

US 2019/0010241 A1 Jan. 10, 2019

Related U.S. Application Data

(63) Continuation of application No. PCT/GB2018/050239, filed on Jan. 26, 2018.

(30) Foreign Application Priority Data

Jan. 27, 2017 (GB) .................................. 1701351.7
Aug. 18, 2017 (GB) .................................. 1713296.0

(51) Int. Cl.
| | |
|---|---|
| *A61K 39/395* | (2006.01) |
| *C07K 16/28* | (2006.01) |
| *C12N 15/09* | (2006.01) |
| *C12N 15/62* | (2006.01) |
| *C07K 16/00* | (2006.01) |

(52) U.S. Cl.
CPC ........ *C07K 16/2878* (2013.01); *C07K 16/005* (2013.01); *C07K 2317/23* (2013.01); *C07K 2317/24* (2013.01); *C07K 2317/33* (2013.01); *C07K 2317/52* (2013.01); *C07K 2317/55* (2013.01); *C07K 2317/567* (2013.01); *C07K 2317/622* (2013.01); *C07K 2317/75* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2007/0098719 | A1 | 5/2007 | Smith et al. |
| 2014/0348841 | A1 | 11/2014 | Schebye et al. |

FOREIGN PATENT DOCUMENTS

| | | | |
|---|---|---|---|
| WO | WO 2006/105021 A2 | 10/2006 | |
| WO | WO 2015/031667 A2 | 3/2015 | |
| WO | WO 2015/184099 A1 | 12/2015 | |
| WO | WO 2015/187835 A2 | 12/2015 | |
| WO | WO 2016/057841 A1 | 4/2016 | |

OTHER PUBLICATIONS

Finlay, W. J. J. et al., "Optimized Generation of High-Affinity, High-Specificity Single-Chain Fv Antibodies from Multiantigen Immunized Chickens," Methods Mol Biol 2011; 681: 383-401.
International Search Report and Written Opinion dated Mar. 28, 2018 for International Application No. PCT/GB2018/050239, 11 pages.
Knee, D. A. et al., "Rationale for anti-GITR cancer immunotherapy," European Journal of Cancer 2016; 67: 1-10.
Mahne, A. E. et al., "Dual Roles for Regulatory T-cell Depletion and Costimulatory Signaling in Agonistic GITR," Cancer Research 2017; 77(5): 1108-1118.
Ponte, J. et al., "Anti-Mouse GITR monoclonal Antibody (Mab) Augments Humoral and Cellular Responses to H5N1 and H3N2 Avian Influenza Hemagglutinin," Clinical Immunology 2007; 123: p. S33.
Townsend, S. et al., "Augmented Binary Substitution: Single-pass CDR germlining and stabilization of therapeutic antibodies," PNAS 2015; 112(50): 15354-15359.
United Kingdom Search Report dated Nov. 30, 2017 for UK Application No. GB1701351.7, 4 pages.
Ahmadi, M. et al. (2014) "Small Amounts of Sub-Visible Aggregates Enhance the Immunogenic Potential of Monoclonal Antibody Therapeutics," Pharm Res., 12 pages; doi: 10.1007/s11095-014-1541.
Almagro, J. C. & Fransson, J. (2008) "Humanization of antibodies," Front Biosci 13: 1619-1633.
Bagshawe, K. D. et al. (1991) "Antibody-Enzyme Conjugates Can Generate Cytotoxic Drugs from Inactive Precursors at Tumor Sites," Antibody, Immunoconjugates and Radiopharmaceuticals 4: 915-922.
Cohen, A. D. et al. (2010) "Agonist anti-GITR monoclonal antibody induces melanoma tumor immunity in mice by altering regulatory T cell stability and intra-tumor accumulation," PLoS One 5(5): e10436, 12 pages.
Fennell, B. J. et al. (2013) "CDR-restricted engineering of native human scFvs creates highly stable and soluble bifunctional antibodies for subcutaneous delivery," mAbs 5(6): 882-895.
Finlay, W. J. et al. (2009) Affinity maturation of a humanized rat antibody for anti-RAGE therapy: comprehensive mutagenesis reveals a high level of mutational plasticity both inside and outside the complementarity-determining regions. J Mol Biol 388(3): 541-558.
Harding, F. A. et al. (2010) "The immunogenicity of humanized and fully human antibodies: residual immunogenicity resides in the CDR regions," mAbs 2(3): 256-265.
Henikoff, S. & Henikoff, J. G. (1992) "Amino acid substitution matrices from protein blocks," PNAS 89: 10915-10919.
Holliger, P. & Hudson, P. J. (2005) "Engineered antibody fragments and the rise of single domains," Nature Biotechnol. 23(9): 1126-1136.

(Continued)

*Primary Examiner* — Michael D Pak
(74) *Attorney, Agent, or Firm* — Cooley LLP; Ivor Elrifi

(57) ABSTRACT

The invention relates to antibody molecules and antigen-binding portions thereof which bind specifically to glucocorticoid-induced TNF receptor (GITR). In particular aspects of the invention, the antibody molecules specifically bind to human GITR and cynomolgus monkey GITR. The anti-GITR antibody molecules of the invention have been developed and optimized using CDR sequences derived from a murine anti-GITR antibody 6C8. Medical uses of the antibody molecules are disclosed.

20 Claims, 24 Drawing Sheets

Specification includes a Sequence Listing.

(56) References Cited

OTHER PUBLICATIONS

Hwang, W. Y. K. & Foote, J. (2005) "Immunogenicity of engineered antibodies," Methods 36(1): 3-10.
Jones, P. T. et al. (1986) "Replacing the complementarity-determining regions in a human antibody with those from a mouse," Nature 321(6069): 522-525.
Ko, K. et al. (2005) "Treatment of advanced tumors with agonistic anti-GITR mAb and its effects on tumor-infiltrating Foxp3+CD25+ CD4+ regulatory T cells," J Exp Med 202(7): 885-891.
Ledermann, J. A. et al. (1991) "A Phase-I Study of Repeated Therapy with Radiolabelled Antibody to Carcinoembryonic Antigen Using Intermittent or Continuous Administration of Cyclosporin A to Suppress the Immune Response," Int. J. Cancer 47: 659-664.
Melero, I. et al. (2013) "Agonist antibodies to TNFR molecules that costimulate T and NK cells," Clin Cancer Res 19(5):1044-1053.
Mouquet, H. et al. (2010) "Polyreactivity increases the apparent affinity of anti-HIV antibodies by heteroligation," Nature 467: 591-595.
Nelson, A. L. et al. (2010) "Development trends for human monoclonal antibody therapeutics," Nat Rev Drug Discov 9(10):767-774.
North, B. et al. (2011) "A new clustering of antibody CDR loop conformations," J Mol Biol 406(2): 228-256.
Swindells, M. B. et al. (2016) "abYsis: Integrated Antibody Sequence and Structure-Management, Analysis, and Prediction," J Mol Biol. [PMID: 27561707; Epub Aug. 22, 2016], 9 pages.
Tiller, T. et al. (2013) "A fully synthetic human Fab antibody library based on fixed VH/VL framework pairings with favorable biophysical properties," mAbs 5(3): 445-470.
Tu, C. et al. (2016) "A Combination of Structural and Empirical Analyses Delineates the Key Contacts Mediating Stability and Affinity Increases in an Optimized Biotherapeutic Single-chain Fv (scFv)," J Biol Chem 291(3): 1267-1276.
Van Aerts, L. A. G. J. M. et al. (2014) "Biosimilars entering the clinic without animal studies: A paradigm shift in the European Union," mAbs 6(5): 1155-1162.
Van Meer, P. J. K. et al. (2013) "Immunogenicity of mAbs in non-human primates during nonclinical safety assessment," mAbs 5(5): 810-816.
Zhou, F. et al. (2006) "A general user interface for prediction servers of proteins' post-translational modification sites," Nature Protocols 1: 1318-1321.
Zhou, P. et al. (2007) "Pivotal roles of CD4+ effector T cells in mediating agonistic anti-GITR mAb-induced-immune activation and tumor immunity in CT26 tumors," J Immunol 179(11): 7365-7375.

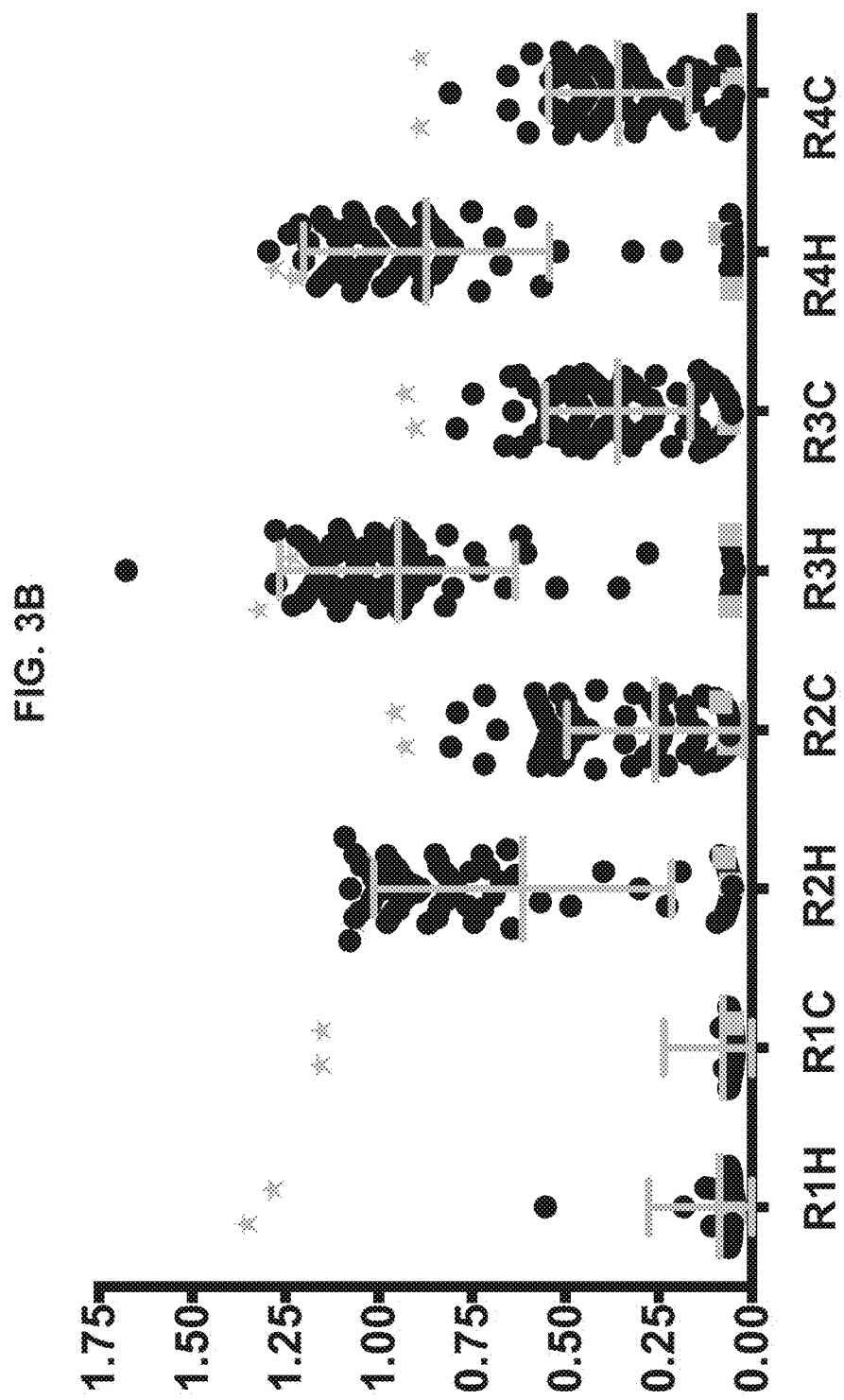

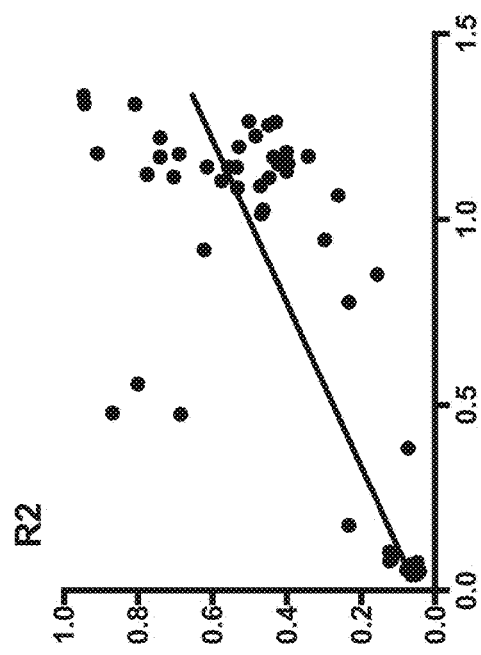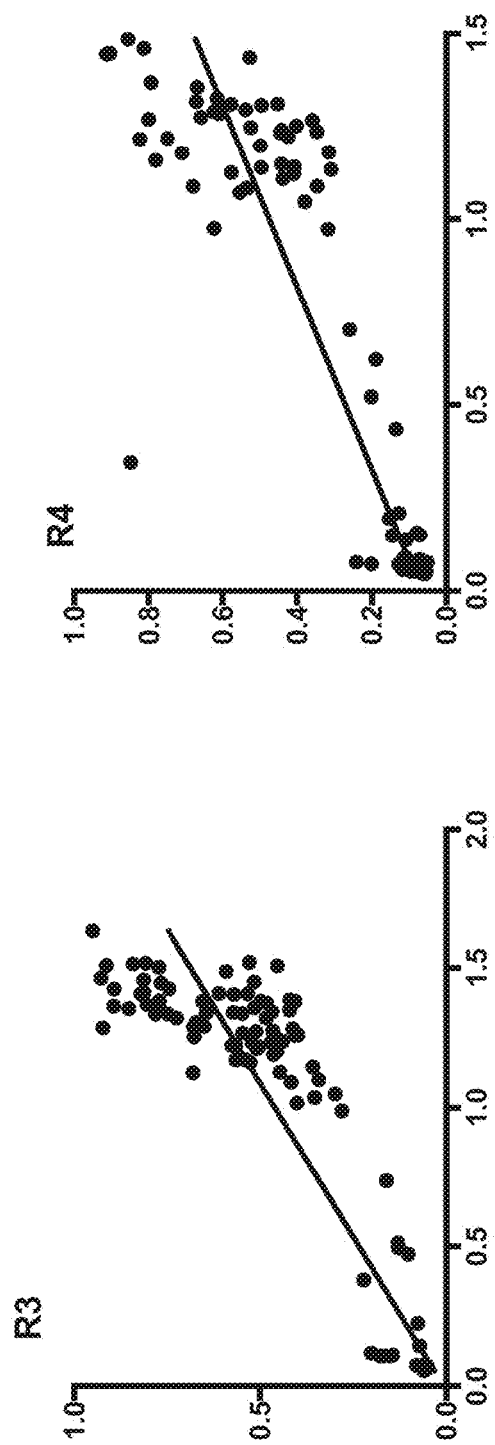
FIG. 4A

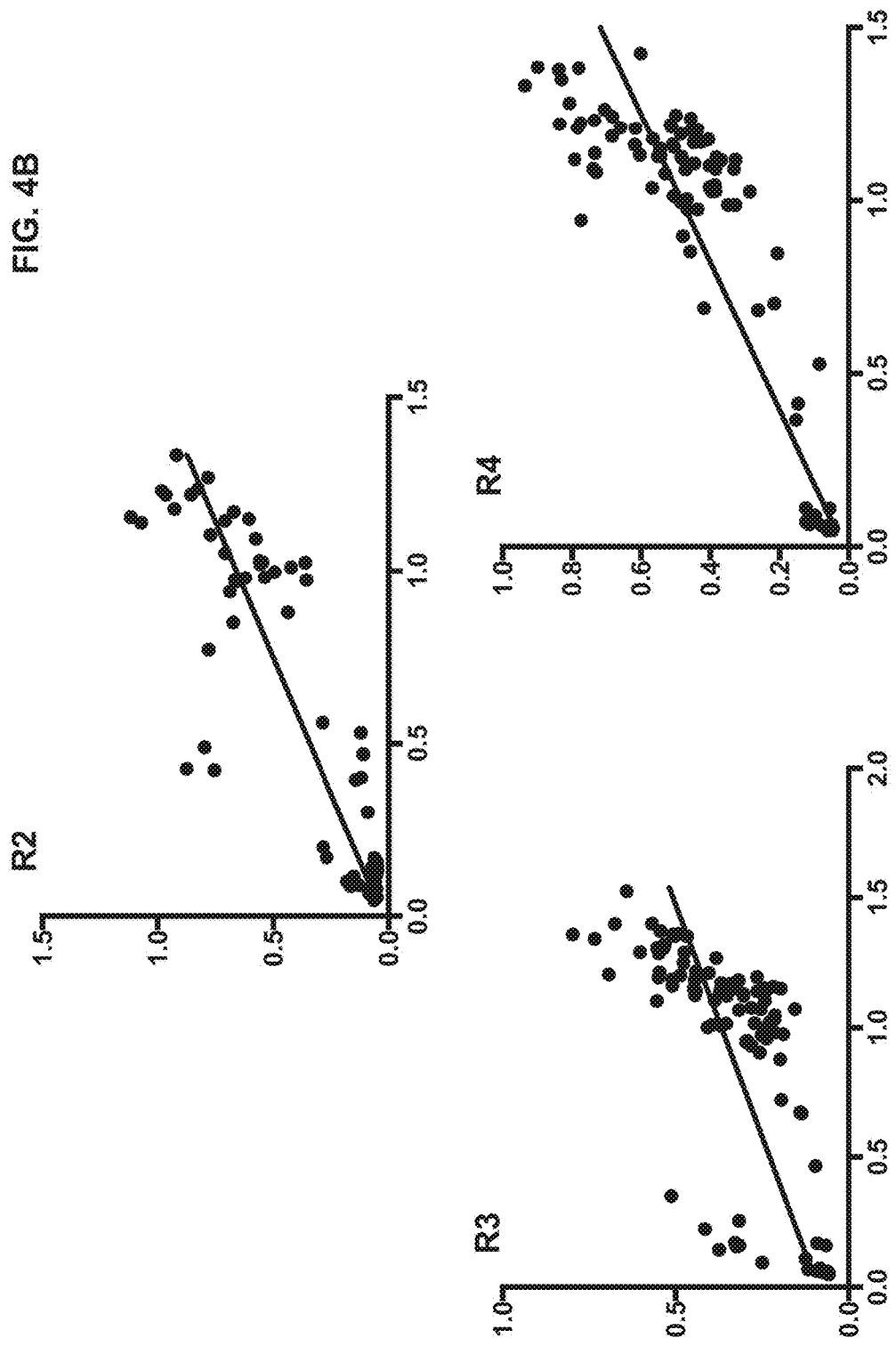

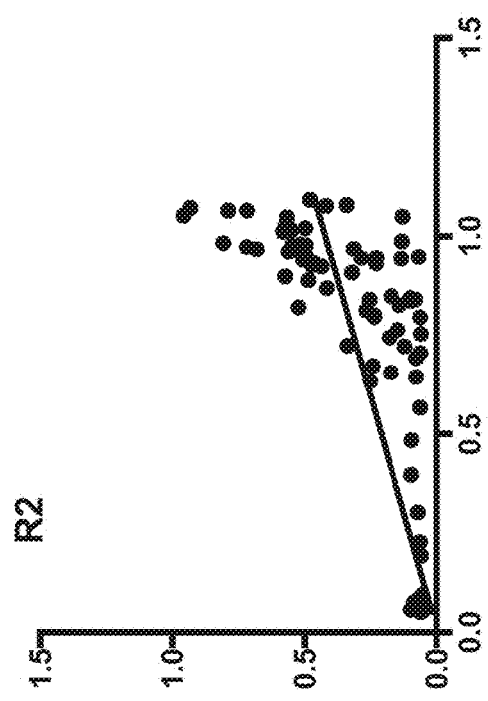
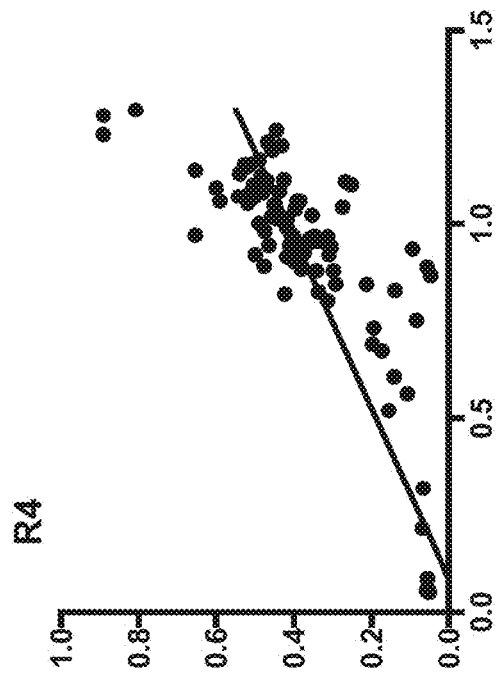
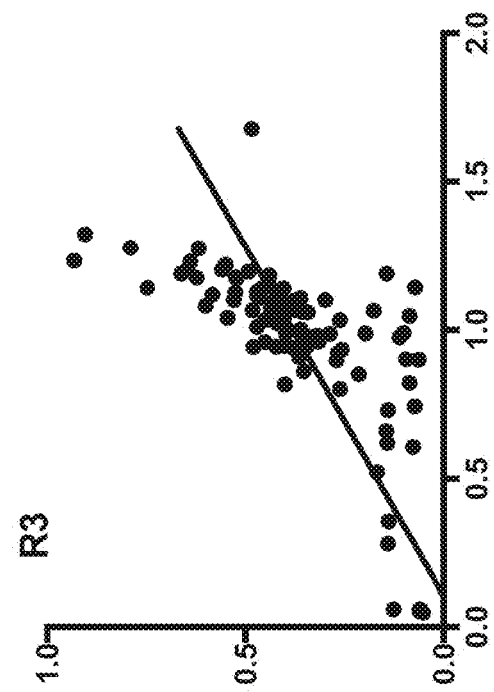
FIG. 4C

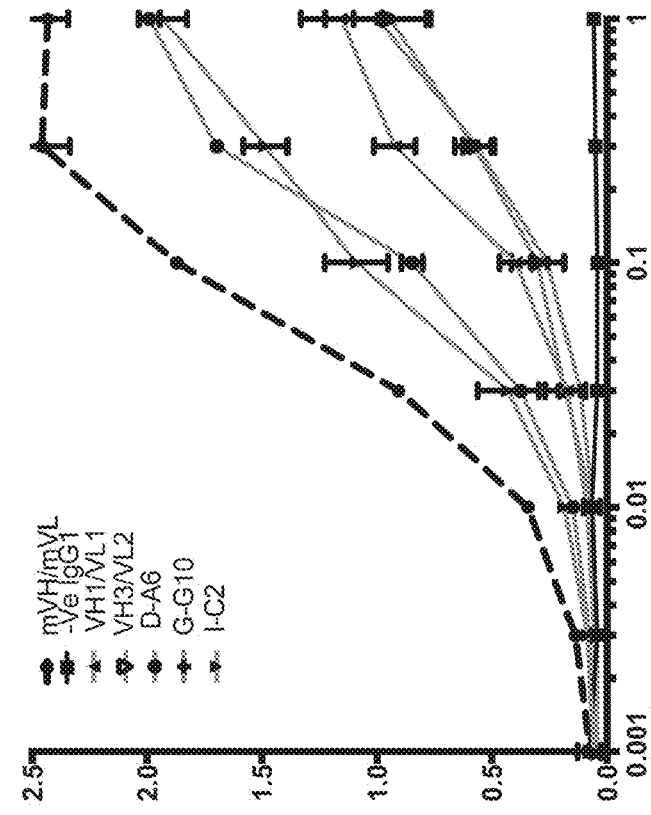
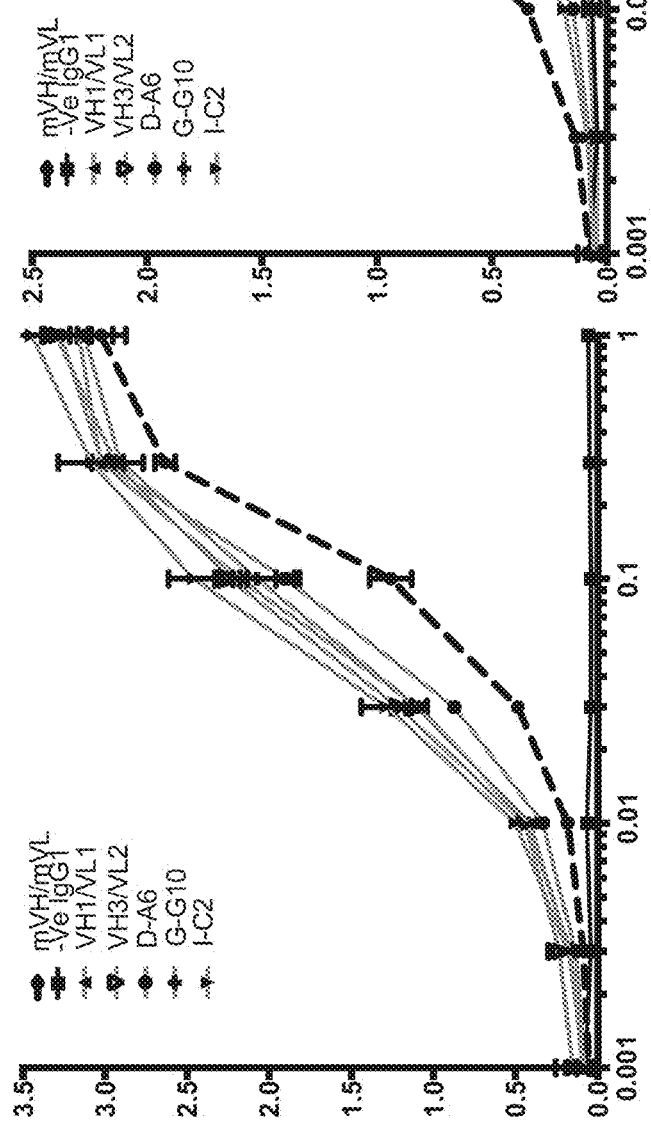
FIG. 6A
FIG. 6B

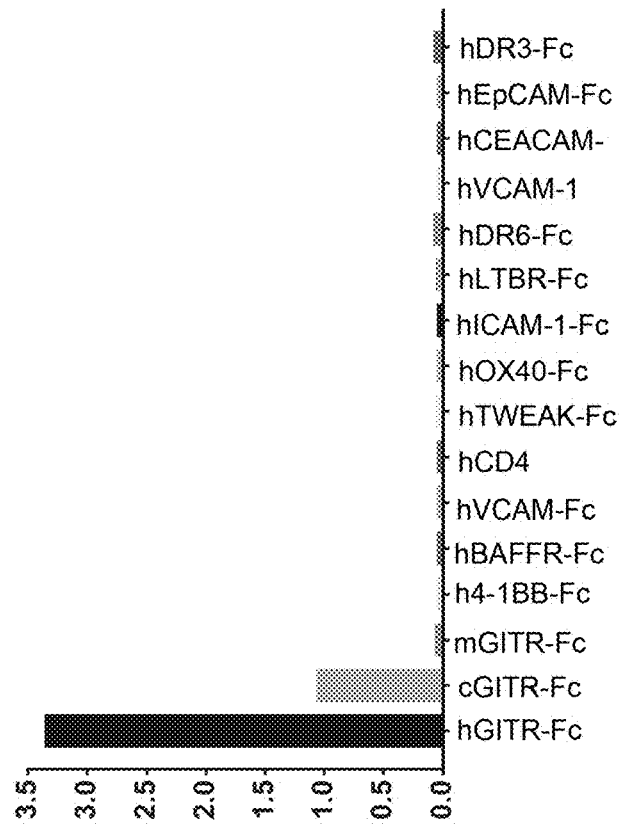
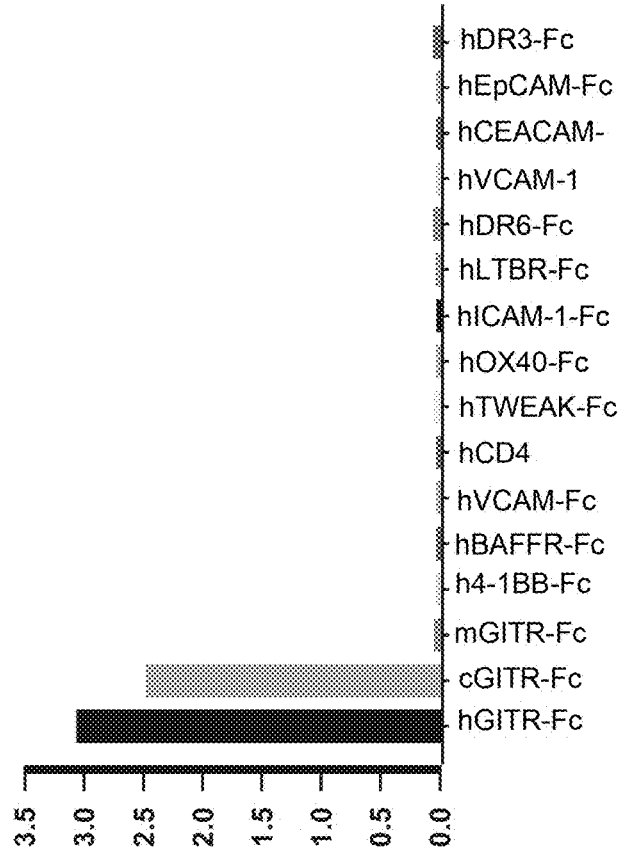

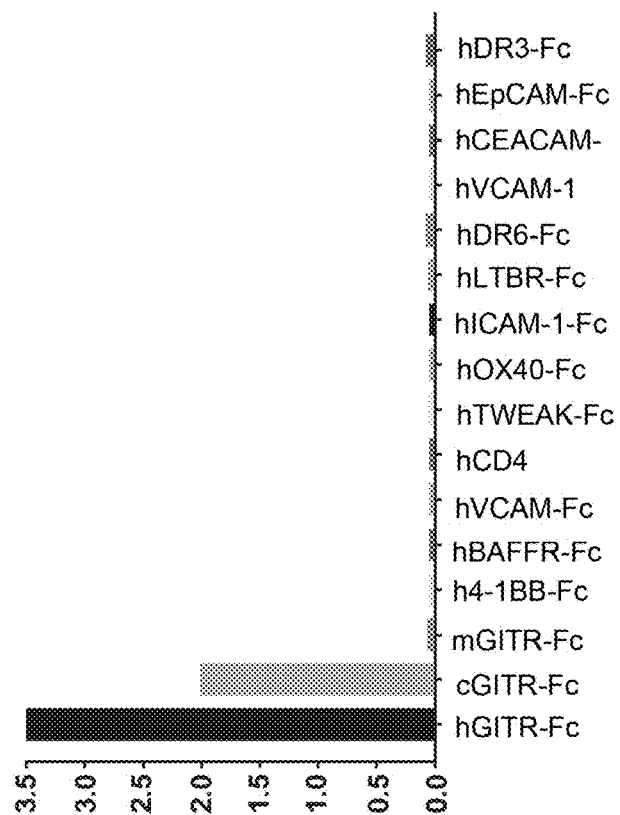
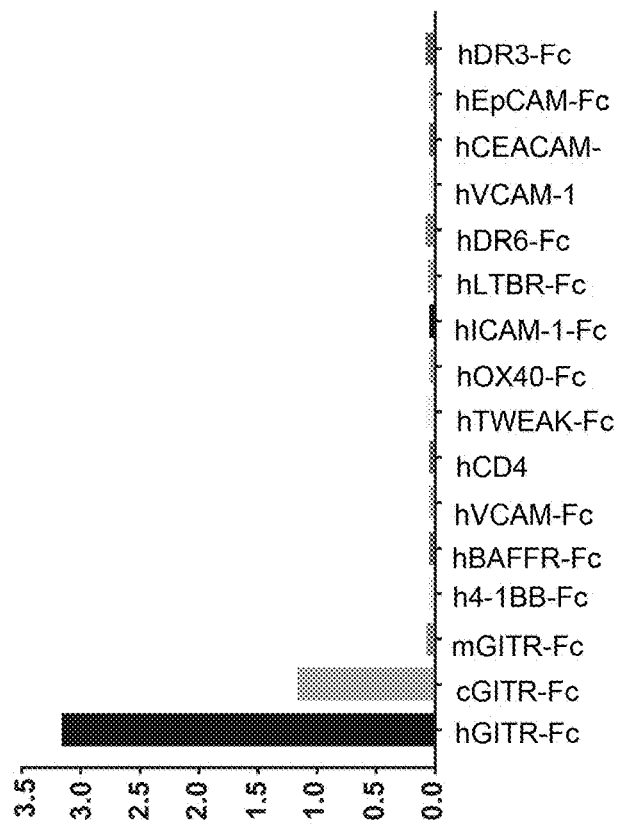

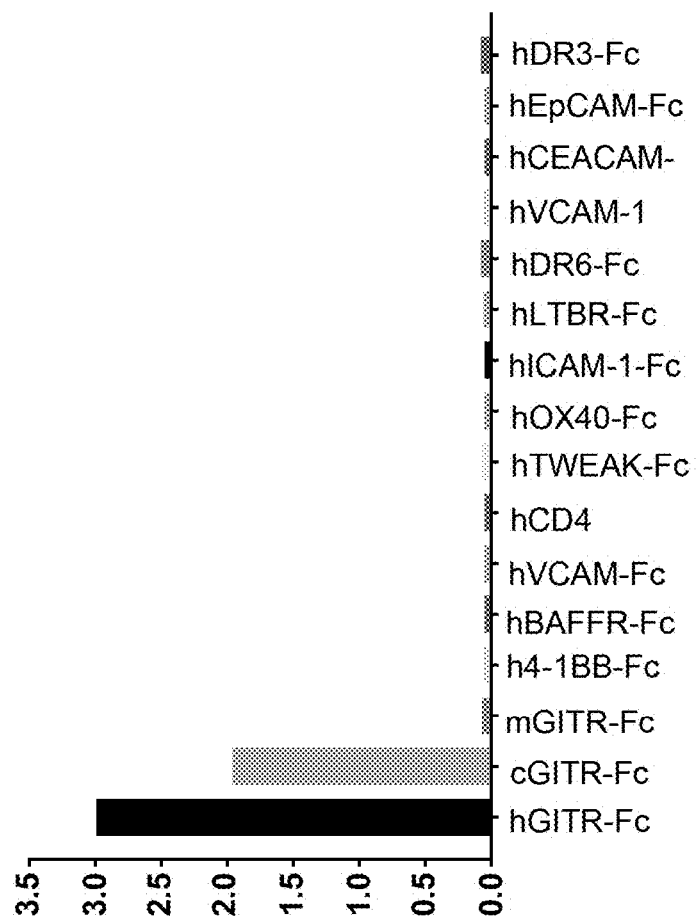

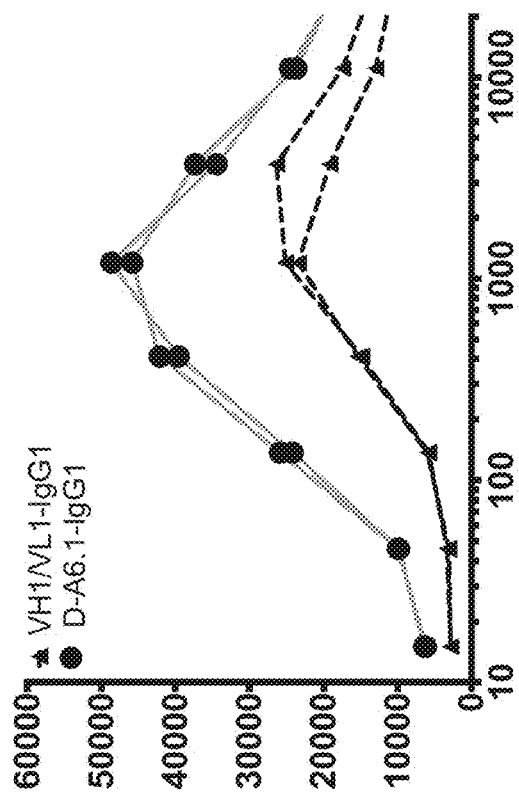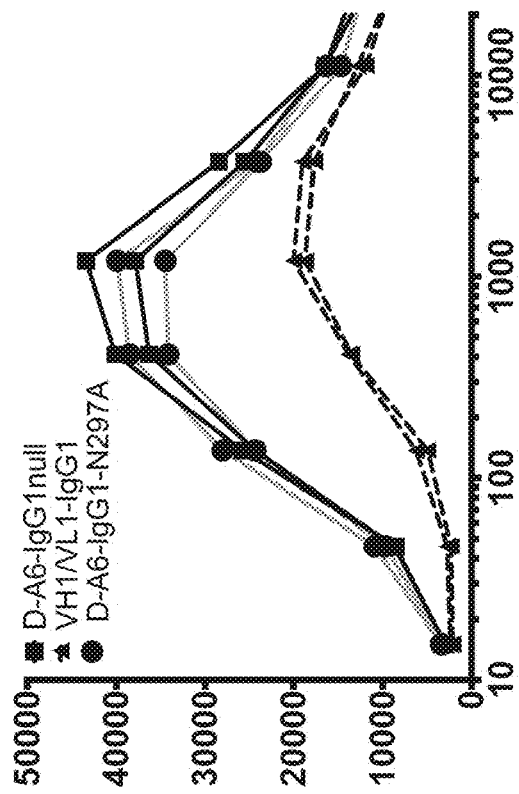

BINDING AGENTS

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULHU_001_C01US_SubSeqList.txt, date recorded: Sep. 25, 2018, file size 51,656 bytes).

FIELD OF THE INVENTION

The invention relates to antibody molecules binding specifically to glucocorticoid-induced TNF receptor (GITR) and medical uses thereof.

BACKGROUND OF THE INVENTION

GITR (also known as TNFRSF18) is a co-stimulatory member of the TNF receptor superfamily. Expression of GITR has been observed predominantly on T cells, NK cells, B cells, and to a lesser extent on some other hematopoietic cell types. GITR exhibits low expression in resting T and NK cells, but constitutively high level expression in CD4+ Foxp3+ regulatory T cells (Tregs). In vitro or in vivo engagement of GITR by GITR ligand or agonist anti-GITR antibodies causes the expansion of CD4+ and CD8+ T cells and improves the resistance of T cells to suppression by Tregs.

Preclinical evidence suggests that inducing GITR signaling can enhance the activation of effector T cells (Teffs) and reduce the activity of Tregs in experimental tumours. Dosing with agonist anti-GITR mAbs leads to enhanced endogenous Teff responses, reduction in the frequency of Tregs in the tumour microenvironment, and subsequent tumor rejection in multiple murine tumor models. Hence, anti-GITR mAbs have the potential to act as immunotherapeutic agents in cancer and other settings, and also to amplify the effectiveness of currently established cancer immunotherapies.

The majority of currently approved antibody therapeutics are derived from immunized rodents. Most of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized agonistic anti-GITR antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination.

CDR germ-lining is thus a complex, multifactorial problem, as multiple functional properties of the molecule should preferably be maintained, including in this instance: target binding specificity, affinity to GITR from both human and animal test species (e.g. cynomolgus monkey, also known as the crab-eating macaque, i.e. *Macaca fascicularis*), v-domain biophysical stability and/or IgG expression yield. Antibody engineering studies have shown that the even single residue positions in key CDRs can have dramatic effects on all of these desired molecular properties.

WO2006/105021 describes an agonistic murine anti-GITR IgG molecule termed "6C8", and also the preparation of humanized forms of 6C8. Those humanized forms of 6C8 were produced using classical humanization techniques, i.e. by grafting of Kabat-defined murine CDRs into human heavy and light chain framework sequences and some of the human framework residues back-mutated to the correspondingly positioned 6C8 murine residues. Only one amino acid modification to one of the Kabat-defined murine CDRs of 6C8 is described in WO2006/105021, to modify a potential glycosylation site. For reasons noted above, such humanized forms of 6C8 described in WO2006/105021 are not ideal.

The present invention provides a number of optimized anti-GITR antibodies and medical uses thereof.

SUMMARY OF THE INVENTION

According to one aspect of the invention, there is provided an antibody molecule which specifically binds to human GITR and optionally also cynomolgus monkey GITR, or an antigen-binding portion thereof, wherein the antibody molecule or antigen-binding portion comprises a heavy chain variable region with:

an HCDR1 having amino acids in sequence in the following order: G-F-S or a conservative substitution of S-L or a conservative substitution of L-S-T or a conservative substitution of T-S or any amino acid (for example, F)-G or a conservative substitution of G-M or any amino acid (for example, Y, F, L or W)-G or a conservative substitution of G-V or a conservative substitution of V-G or a conservative substitution of G (SEQ ID NO: 1);

an HCDR2 having amino acids in sequence in the following order: L or a conservative substitution of L-A or a conservative substitution of A-H or a conservative substitution of H-I or a conservative substitution of I-W-W-D or a conservative substitution of D-D or a conservative substitution of D-D or a conservative substitution of D-K-Y-Y-N or any amino acid (for example, V)-P or any amino acid (for example, D)-S-L or a conservative substitution of L-K-S or any amino acid (for example, G) (SEQ ID NO: 2); and an HCDR3 having amino acids in sequence in the following order: T or any amino acid (for example, G, A, N, S or I)-R or any amino acid (for example, D, T or V)-R or any amino acid (for example, Q, L, M, I or V)-Y-F or a conservative substitution of F-P-F-A-Y (SEQ ID NO: 3);

and wherein at least one of the HCDR1, HCDR2 or HCDR3 has at least one amino acid difference where permitted compared with the amino acid sequences GFSLSTSGMGVG (SEQ ID NO: 4; 6C8 murine HCDR1), LAHIWWDDDKYYNPSLKS (SEQ ID NO: 5; 6C8 murine HCDR2), LAHIWWDDDKYYQPSLKS (SEQ ID NO: 65; 6C8 mutant HCDR2) and TRRYFPFAY (SEQ ID NO: 6; 6C8 murine HCDR3), respectively.

In another aspect of the invention, the antibody molecule or antigen-binding portion comprises a heavy chain variable region with an HCDR1 having amino acids in sequence in the following order: F-S-L-S-T-S/F-G-Y-G (SEQ ID NO: 7);

an HCDR2 having amino acids in sequence in the following order: I-W-W-D-D-D-K-Y-Y-V-D-S-V-K-G (SEQ ID NO: 8); and an HCDR3 having amino acids in sequence in the following order: T-R-Q/L/V-Y-F-P-F-A (SEQ ID NO: 9).

In preferred aspects of the invention, the antibody molecule specifically binds to human GITR and also cynomolgus monkey GITR.

The antibody molecule or antigen-binding portion may further comprise a light chain variable region with:

an LCDR1 having amino acids in sequence in the following order: K or a conservative substitution of K-A or a conservative substitution of A-S-Q-N or a conservative substitution of N-V-G or a conservative substitution of G-T or a conservative substitution of T-N or any amino acid (for example, Y)-V or a conservative substitution of V-A (SEQ ID NO: 10);

an LCDR2 having amino acids in sequence in the following order: S or any amino acid (for example Y, E, D, F, L or N)-A-S or any amino acid (for example, Y)-Y or any amino acid (for example, N)-R-Y or any amino acid (for example A or D)-S or a conservative substitution of S (SEQ ID NO: 11); and an LCDR3 having amino acids in sequence in the following order: Q-Q or a conservative substitution of Q-Y or any amino acid (for example, R or H)-N or a conservative substitution of N-T or any amino acid (for example K or N)-D or any amino acid (for example, W, L, S, E, V or N)-P-L-T (SEQ ID NO: 12);

and wherein at least one of the LCDR1, LCDR2 or LCDR3 has at least one amino acid difference where permitted compared with the amino acid sequences KASQNVGTNVA (SEQ ID NO: 13) (6C8 murine LCDR1), SASYRYS (SEQ ID NO: 14) (6C8 murine LCDR2) and QQYNTDPLT (SEQ ID NO: 15) (6C8 murine LCDR3), respectively.

In another aspect, the antibody molecule or antigen-binding portion of the invention comprises a light chain variable region with:

an LCDR1 having amino acids in sequence in the following order: A-S-Q-N/S-V-G-T/S-N (SEQ ID NO: 16);

an LCDR2 having amino acids in sequence in the following order: S/Y-A-S-Y/N—R-Y-S/T (SEQ ID NO: 17); and an LCDR3 having amino acids in sequence in the following order: Y-S-T/N-D-P-L (SEQ ID NO: 18).

Also provided according to the invention is an immunoconjugate comprising the antibody molecule or antigen-binding portion thereof as defined herein linked a therapeutic agent.

In another aspect the invention provides nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-GITR antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method of producing an antibody molecule which specifically binds to human GITR and optionally also cynomolgus monkey GITR, or an antigen-binding portion thereof, comprising the steps of:

(1) grafting anti-GITR CDRs from a non-human source into a human v-domain framework to produce a humanized anti-GITR antibody molecule or antigen-binding portion thereof;

(2) generating a phage library of clones of the humanized anti-GITR antibody molecule or antigen-binding portion thereof comprising one or more mutations in the CDRs;

(3) screening the phage library for binding to human GITR and cynomolgus monkey GITR;

(4) selecting clones from the screening step (3) having binding specificity to human GITR and cynomolgus monkey GITR; and (5) producing an antibody molecule which specifically binds to human GITR and cynomolgus monkey GITR or an antigen-binding portion thereof from clones selected from step (4).

BRIEF DESCRIPTION OF THE FIGURES

FIG. 3A-3C. Direct binding ELISA of library-derived anti-GITR scFvs against human and cyno GITR-Fc proteins. FIG. 3A shows Branch A periprep ELISA (hum-cyno-hum-cyno), FIG. 3B shows Branch B periprep ELISA (cyno-hum-cyno-hum), and FIG. 3C shows Branch C periprep ELISA (hum-hum-hum-hum). Clones were derived from 3 separate phage selection branches (FIG. 3A, 3B, 3C) where phage populations were selected on biotinylated human (hum), or cynomolgus (cyno) GITR-Fc proteins in each round. After each round of selection, 92 library-derived clones (black circles) plus two positive control (grey stars) and two negative control scFvs (grey squares) per round were screened against both hum and cyno GITR-Fc. Mean±SD values in each round are represented in grey bars. In each graph, X-axis shows selection round ("R"), with "H" denoting human and "C" denoting cyno, and Y-axis shows binding signal (OD 450 nm).

FIG. 4A-4C. Linear regression correlation analysis of direct binding ELISA for selected anti-GITR scFvs against human and cyno GITR-Fc proteins. Binding values from 3 separate phage selection branches (FIG. 4A, 4B, 4C) are plotted showing the binding signals (OD 450 nm) for single clones against both hum (X-axes) and cyno (Y-axes) GITR-Fc after round ("R") 2, 3 and 4. Library-derived anti-GITR clones are represented by black circles, with a correlation trend line for each analysis. Branch FIG. 4C values show that selection only on human GITR protein results in a more biased population, with more clones showing reactivity to human and not cyno.

FIG. 6A-6D. Direct titration ELISA for IgG binding to human and cyno GITR-Fc proteins. Chimeric anti-GITR (mVH/mVL), human germline grafts (VH1/VL1, VH3/VL2) and library-derived clones in human IgG1 format were titrated (in µg/ml) in a direct binding ELISA against human (FIGS. 6A, 6C) and cyno (FIGS. 6B, 6D) GITR-Fc proteins. Clones demonstrating binding activity equivalent to, or improved over, the VH1/VL1 and VH3/VL2 IgGs against both human and cyno are shown in (FIG. 6A) and (FIG. 6B). Clones demonstrating binding activity inferior to the VH1/VL1 and VH3/VL2 IgGs against either human GITR-Fc, cyno GITR-Fc or both, are shown in (FIG. 6C) and (FIG. 6D). In each graph, X-axis shows IgG concentration in µg/ml and Y-axis shows binding signal (OD 450 nm).

FIG. 8A-8E. Binding specificity analyses for prioritized lead clones. Off-target homologue binding risk for mVH/mVL (FIG. 8A), VH3/VL2 (FIG. 8B) and lead engineered IgG clones G-G10 (FIG. 8C), I-C2 (FIG. 8D) and D-A6 (FIG. 8E) was examined by direct ELISA on GITR-Fc orthologs and a panel of 13 human TNFRSF and immunoglobulin superfamily proteins (as labelled on each X-axis). Binding to human, cyno and murine GITR-Fcs (h/c/mGITR-Fc) was performed at an IgG concentration of 1 µg/ml. Binding to all other proteins was performed at an IgG concentration of 10 µg/ml. In each plot, Y-axis shows binding signal (OD 450 nm). For all IgGs, binding was observed to hGITR-Fc and cGITR-Fc alone. No binding above background was observed for mGITR-Fc or any homologous human protein.

FIG. 12A) In this assay, the specificity of antibody binding to CHO-K1 human GITR+ cells was demonstrated by flow cytometric staining in the presence or absence of excess soluble, purified recombinant human GITR ligand (GITRL) protein. For both VH1/VL1 and D-A6 antibodies, binding signal to the GITR+ cells for the antibody at 1.1 µg/ml was reduced >10-fold in the presence of 10 µg/ml soluble GITRL protein. A negative control anti-GFP antibody showed no measurable binding to the CHO-K1 GITR cells. "N" denotes naïve cells; "A" denotes activated cells. FIG. 12B) Both D-A6 IgG1 and VH1/VL1 IgG1 also showed clear reactivity to the human HuT78 T cell line when the cells had been activated via CD3/CD28 stimulation, but not when naive. GITR upregulation on the activated cells was confirmed by strong positive staining with the anti-human GITR monoclonal reagent antibody 108-17. "Ab" denotes 1.11 µg/ml antibody; "Ab+GITRL" denotes 1.11 µg/ml antibody+10 µg/ml GITRL. X-axis shows antibody and y-axis shows MFI of live cells. In each plot, Y-axis shows MFI of live cells.

FIG. 15A-15D. GITR Jurkat cell reporter assay for prioritized leads. Duplicate analyses of cross-linking of human GITR at the cell surface for lead clones D-A6 in IgG1null and IgG1-N297A formats (FIG. 15A), D-A6.1 (FIG. 15B) and the library-derived leads G-G10 (FIG. 15C) and I-C2 (FIG. 15D), in IgG1 format, showed that all clones provoked more potent concentration-dependent agonistic activity in comparison to VH1/VL1 IgG1. In FIG. 15C and FIG. 15D, "I IgG1" denotes Isotype IgG1. In each graph, x-axis shows IgG concentration in ng/ml and y-axis shows RLU.

DETAILED DESCRIPTION OF THE INVENTION

Figure 1A:
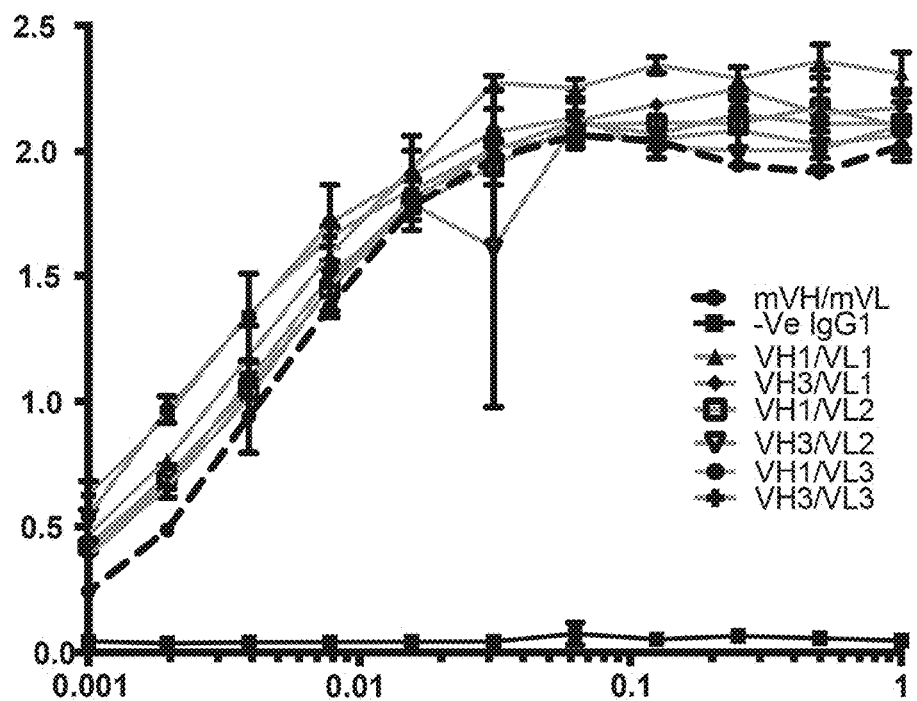
FIG. 1A-1B. Direct titration ELISA for IgG binding to human GITR-Fc. Chimeric anti-GITR and human germline grafts in human IgG1 format were titrated (in µg/ml) against human GITR-Fc protein. Clones demonstrating binding activity equivalent to the chimeric IgG (VH1 and VL3 families) are shown in FIG. 1A, and those with impaired binding (VH2 and VH4 families) in FIG. 1B. In each graph, X-axis shows IgG concentration in µg/ml and Y-axis shows binding signal (OD 450 nm).

According to a first aspect of the invention, there is provided an antibody molecule which specifically binds to human GITR and optionally also cynomolgus monkey GITR, or an antigen-binding portion thereof, wherein the antibody molecule or antigen-binding portion comprises a heavy chain variable region with:

an HCDR1 having amino acids in sequence in the following order: G-F-S or a conservative substitution of S-L or a conservative substitution of L-S-T or a conservative substitution of T-S or any amino acid (for example, F)-G or a conservative substitution of G-M or any amino acid (for example, Y, F, L or W)-G or a conservative substitution of G-V or a conservative substitution of V-G or a conservative substitution of G (SEQ ID NO: 1);

an HCDR2 having amino acids in sequence in the following order: L or a conservative substitution of L-A or a conservative substitution of A-H or a conservative substitution of H-I or a conservative substitution of I-W-W-D or a conservative substitution of D-D or a conservative substitution of D-D or a conservative substitution of D-K-Y-Y-N or any amino acid (for example, V)-P or any amino acid (for example, D)-S-L or a conservative substitution of L-K-S or any amino acid (for example, G) (SEQ ID NO: 2); and an HCDR3 having amino acids in sequence in the following order: T or any amino acid (for example, G, A, N, S or I)-R or any amino acid (for example, D, T or V)-R or any amino acid (for example, Q, L, M, I or V)-Y-F or a conservative substitution of F-P-F-A-Y (SEQ ID NO: 3);

and wherein at least one of the HCDR1, HCDR2 or HCDR3 has at least one amino acid difference, for example one, two, three, four, five or more amino acid differences, where permitted according to the above definition, compared with the amino acid sequences GFSLSTSGMGVG (SEQ ID NO: 4; 6C8 murine HCDR1), LAHIWWDDDKYYNPSLKS (SEQ ID NO: 5; 6C8 murine HCDR2), LAHIWWDDDKYYQPSLKS (SEQ ID NO: 65; 6C8 mutant HCDR2) and TRRYFPFAY (SEQ ID NO: 6; 6C8 murine HCDR3), respectively.

The sequence LAHIWWDDDKYYNPSLKS (SEQ ID NO: 5) defining HCDR2 from 6C8 murine antibody as disclosed in WO2006/105021 includes the wild-type murine sequence with N at position N. A mutant form thereof disclosed in WO2006/105021 with Q at position N (LAHIWWDDDKYYQPSLKS; SEQ ID NO: 65) is stated to remove a putative glycosylation site.

The HCDR1, HCDR2 and HCDR3 of the antibody molecule or antigen-binding portion thereof may each have at least one amino acid difference, for example one, two, three, four, five or more amino acid differences, where permitted according to the above definition, compared with the amino acid sequences GFSLSTSGMGVG (SEQ ID NO: 4; 6C8 murine HCDR1), LAHIWWDDDKYYNPSLKS (SEQ ID NO: 5; 6C8 murine HCDR2), LAHIWWDDDKYYQPSLKS (SEQ ID NO: 65; 6C8 mutant HCDR2) and TRRYFPFAY (SEQ ID NO: 6; 6C8 murine HCDR3), respectively.

The antibody molecule or antigen-binding portion thereof according to the invention may further comprise a light chain variable region with:

an LCDR1 having amino acids in sequence in the following order: K or a conservative substitution of K-A or a conservative substitution of A-S-Q-N or a conservative substitution of N-V-G or a conservative substitution of G-T or a conservative substitution of T-N or any amino acid (for example, Y)-V or a conservative substitution of V-A (SEQ ID NO: 10);

an LCDR2 having amino acids in sequence in the following order: S or any amino acid (for example Y, E, D, F, L or N)-A-S or any amino acid (for example, Y)-Y or any amino acid (for example, N)-R-Y or any amino acid (for example A or D)-S or a conservative substitution of S (SEQ ID NO: 11); and an LCDR3 having amino acids in sequence in the following order: Q-Q or a conservative substitution of Q-Y or any amino acid (for example, R or H)-N or a conservative substitution of N-T or any amino acid (for example K or N)-D or any amino acid (for example, W, L, S, E, V or N)-P-L-T (SEQ ID NO: 12);

and wherein at least one of the LCDR1, LCDR2 or LCDR3 has at least one amino acid difference, for example one, two, three, four, five or more amino acid differences, where permitted according to the above definition, compared with the amino acid sequences KASQNVGTNVA (SEQ ID NO: 13; 6C8 murine LCDR1), SASYRYS (SEQ ID NO: 14; 6C8 murine LCDR2) and QQYNTDPLT (SEQ ID NO: 15; 6C8 murine LCDR3), respectively.

The LCDR1, LCDR2 and LCDR3 of the antibody molecule or antigen-binding portion thereof may each have at least one amino acid difference, for example one, two, three, four, five or more amino acid differences, where permitted according to the above definition, compared with the amino acid sequences KASQNVGTNVA (SEQ ID NO: 13; 6C8 murine LCDR1), SASYRYS (SEQ ID NO: 14; 6C8 murine LCDR2) and QQYNTDPLT (SEQ ID NO: 15; 6C8 murine LCDR3), respectively.

As elaborated herein, the present inventors have succeeded for the first time in generating a number of optimized anti-GITR antibody molecules using CDR sequences derived from the murine anti-GITR antibody 6C8 disclosed in WO2006/105021. Preferred antibody molecules of the invention have been selected to have binding specificity to both human GITR as well as cynomolgus monkey GITR (in order to facilitate studies in an animal test species). Further refining of the optimized antibody molecules as described herein has provided improved binding to the cynomolgus monkey orthologue of GITR, improved potency in agonism of human GITR signaling, improved engagement of the FcγRIIIa receptor to drive ADCC responses in vivo, good variable domain stability, high expression yields, and/or reduced immunogenicity.

Preferred optimized anti-GITR antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-GITR binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to GITR. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence G-F-S/T-L/F-S-T/A-S/F-G/S-M/Y/F/L/W-G/A-V/M-G/S (SEQ ID NO: 19);

the HCDR2 may have the amino acid sequence L/V-A/S-H/N-I/V-W-W-D/E-D/S-D/E-K-Y-Y-N/V-P/D-S-L/V-K-S/G (SEQ ID NO: 20); and the HCDR3 may have the amino acid sequence T/G/A/N/S/I-R/D/T/V-R/Q/L/M/I/V-Y-F/Y-P-F-A-Y (SEQ ID NO: 21).

For example, the HCDR1 may have the amino acid sequence G-F-S/T-L/F-S-T/A-S/F-G/S-M/Y/F/L/W-G/A-V/M-G/S (SEQ ID NO: 19);

the HCDR2 may have the amino acid sequence L/V-A/S-H/N-I/V-W-W-D/E-D/S-D/E-K-Y-Y-V-D-S-V-K-G (SEQ ID NO: 30); and the HCDR3 may have the amino acid sequence T/G/A/N/S/I-R/D/T/V-R/Q/L/M/I/V-Y-F/Y-P-F-A-Y (SEQ ID NO: 21).

In the antibody molecule or antigen-binding portion thereof, the LCDR1 may have the amino acid sequence K/R-A/T-S-Q-N/D/S-V-G/S-T/S/N-N/Y-V/L-A (SEQ ID NO: 22);

the LCDR2 may have the amino acid sequence S/Y/E/D/F/L/N-A-S/Y-Y/N-R-Y/A/D-S/T (SEQ ID NO: 23); and the LCDR3 may have the amino acid sequence Q-Q/H-Y/R/H-N/S/R-T/K/N-D/W/L/S/E/V/N-P-L-T (SEQ ID NO: 24).

For example, the LCDR1 may have the amino acid sequence R-A/T-S-Q-N/D/S-V-G/S-T/S/N-N/Y-V/L-A (SEQ ID NO: 174);

the LCDR2 may have the amino acid sequence S/Y/E/D/F/L/N-A-S/Y-Y/N-R-Y/A/D-S/T (SEQ ID NO: 23); and the LCDR3 may have the amino acid sequence Q-Q/H-Y/R/H-N/S/R-T/K/N-D/W/L/S/E/V/N-P-L-T (SEQ ID NO: 24).

In another aspect of the invention, there is provided an antibody molecule which specifically binds to human glucocorticoid-induced TNF receptor (GITR) and cynomolgus monkey GITR, or an antigen-binding portion thereof, wherein the antibody molecule or antigen-binding portion comprises a heavy chain variable region with:

an HCDR1 having amino acids in sequence in the following order: F-S-L-S-T-S/F-G-Y-G (SEQ ID NO: 7);

an HCDR2 having amino acids in sequence in the following order: I-W-W-D-D-D-K-Y-Y-V-D-S-V-K-G (SEQ ID NO: 8); and an HCDR3 having amino acids in sequence in the following order: T-R-Q/L/V-Y-F-P-F-A (SEQ ID NO: 9).

The CDR sequences above are defined using the shorter "AHo" definition, rather than the "Unified" definition, as set out in Table 1. The AHo definition is based on structural biology and aims to unify nomenclature for all immunoglobulin v-domains.

The antibody molecule or antigen-binding portion as defined above using Aho CDR definitions may alternatively be defined using the Unified definition such that:

the HCDR1 comprises amino acids in sequence in the following order: G-F-S-L-S-T-S/F-G-Y-G-V-G (SEQ ID NO: 25);

the HCDR2 comprises amino acids in sequence in the following order: L-A-H-I-W-W-D-D-D-K-Y-Y-V-D-S-V-K-G (SEQ ID NO: 26); and the HCDR3 comprises amino acids in sequence in the following order: T-R-Q/L/V-Y-F-P-F-A-Y (SEQ ID NO: 27).

In this aspect of the invention, the antibody molecule or antigen-binding thereof may comprise a light chain variable region with:

an LCDR1 having amino acids in sequence in the following order: A-S-Q-N/S-V-G-T/S-N (SEQ ID NO: 16);

an LCDR2 having amino acids in sequence in the following order: S/Y-A-S-Y/N-R-Y-S/T (SEQ ID NO: 17); and an LCDR3 having amino acids in sequence in the following order: Y-S-T/N-D-P-L (SEQ ID NO: 18).

Again, the CDR sequences above are defined using the AHo definition. Alternatively, using the Unified definition, the antibody molecule or antigen-binding thereof may comprise a light chain variable region in which:

the LCDR1 comprises amino acids in sequence in the following order: R-A-S-Q-N/S-V-G-T/S-N-L-A (SEQ ID NO: 28);

the LCDR2 comprises amino acids in sequence in the following order: S/Y-A-S-Y/N-R-Y-SIT (SEQ ID NO: 17); and the LCDR3 comprises amino acids in sequence in the following order: Q-Q-Y-S-T/N-D-P-L-T (SEQ ID NO: 173).

Specific embodiments of this aspect of the invention include an antibody molecule or antigen-binding portion thereof comprising:

(a) the amino acid sequences GFSLSTSGYGVG (SEQ ID NO: 29) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASYRYT (SEQ ID NO: 33) (LCDR2) and QQYSTDPLT (SEQ ID NO: 34) (LCDR3) [Clone D_A6]; or (b) the amino acid sequences GFSLSTFGYGVG (SEQ ID NO: 35) (HCDR1), LAHIWWDDDKYYVDSVKG (SEQ ID NO: 26) (HCDR2), TRQYFPFAY (SEQ ID NO: 31) (HCDR3), RASQSVGTNLA (SEQ ID NO: 36) (LCDR1), YASYRYT (SEQ ID NO: 37) (LCDR2) and QQYSNDPLT (SEQ ID NO: 38) (LCDR3) [Clone G_G10]; or (c) the amino acid sequences GFSLSTSGYGVG (SEQ ID NO: 29) (HCDR1), LAHIQWWDDDKYYVDSVKG (SEQ ID NO: 26) (HCDR2), TRLYFPFAY (SEQ ID NO: 39) (HCDR3), RASQNVGSNLA (SEQ ID NO: 40) (LCDR1), SASNRYS (SEQ ID NO: 41) (LCDR2) and QQYSTDPLT (SEQ ID NO: 34) (LCDR3) [Clone I_C2]; or (d) the amino acid sequences GFSLSTSGYGVG (SEQ ID NO: 29) (HCDR1), LAHIWWDDDKYYVDSVKG (SEQ ID NO: 26) (HCDR2), TRVYFPFAY (SEQ ID NO: 42) (HCDR3), RASQNVGTNLA (SEQ ID NO: 43) (LCDR1), SASYRYT (SEQ ID NO: 33) (LCDR2) and QQYSTDPLT (SEQ ID NO: 34) (LCDR3) [Clone H_B3]; or (e) the amino acid sequences GFSLSTSGYGVG (SEQ ID NO: 29) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASNRYT (SEQ ID NO: 44) (LCDR2) and QQYSTDPLT (SEQ ID NO: 34) (LCDR3) [Clone A6.1].

The antibody molecule or antigen-binding portion thereof comprising the CDR sequences of Clone D_A6 as defined above is a particular specific embodiment of the invention.

The antibody molecule or antigen-binding portion according to this invention may have improved GITR activation compared with a humanized murine anti-GITR IgG antibody labelled as "HuN6C8-Agly" in WO2006/105021.

The known antibody HuN6C8-Agly is understood to be synonymous with the antibody "TRX-518" (or "TRX518") currently being developed by Leap Therapeutics, Inc. The HuN6C8-Agly/TRX-518 antibody comprises "SEQ ID NO: 53" as defined in WO2006/105021 (and corresponding to the "GITR-VH1" sequence in Table 2 below) and "SEQ ID NO: 44" as defined in WO2006/105021 (and corresponding to GITR-VL1 sequence in Table 2 below). The complete sequence of the HuN6C8-Agly/TRX-518 light chain is defined by "SEQ ID NO: 58" of WO2006/105021, and the complete sequence of the HuN6C8-Agly/TRX-518 heavy chain is defined by "SEQ ID NO: 61" of WO2006/105021.

Improved GITR activation as used herein may be defined as exhibiting a maximum signal (RLU value or fold activation) in the Promega GITR Bioassay Kit (CS184006), for example as described in Example 1 below, that is at least 1.5-fold higher than that observed for the antibody TRX-518.

The antibody molecule or antigen-binding portion according to this invention may have improved in silico immunogenicity compared with the antibody TRX-518.

In silico immunogenicity may be determined using the Lonza Epibase IS system (Version 3), for example as described in Example 1 below.

The antibody molecule or antigen-binding portion according to this invention may have an in silico immunogenicity total DRB1 score of less than 1600, for example less than 1500, less than 1100, or particularly less than 900, as determined by the Lonza Epibase IS system (Version 3).

The antibody molecule or antigen-binding portion according to this invention may have improved affinity for cynomolgus monkey GITR compared with the antibody TRX-518. Affinity may be determined using SPR analysis as described in Example 1 below.

In other specific embodiments of the invention, the antibody molecule or antigen-binding portion thereof may comprise:

(a) the amino acid sequences GFSLSTSGMGMS (SEQ ID NO: 61) (HCDR1), LAHIWWDDDKYYVDSVKG (SEQ ID NO: 26) (HCDR2), NRRYFPFAY (SEQ ID NO: 45) (HCDR3), RASQNVGSNLA (SEQ ID NO: 40) (LCDR1), SASYRAT (SEQ ID NO: 46) (LCDR2) and QQYSNDPLT (SEQ ID NO: 38) (LCDR3) [Clone C_B10]; or (b) the amino acid sequences GFSLSTSGYGVS (SEQ ID NO: 47) (HCDR1), LAHVWWDDEKYYVDSVKG (SEQ ID NO: 48) (HCDR2), NRRYFPFAY (SEQ ID NO: 45) (HCDR3), RASQSVGTNVA (SEQ ID NO: 49) (LCDR1), SASYRAT (SEQ ID NO: 46) (LCDR2) and QQYNNWPLT (SEQ ID NO: 50) (LCDR3) [Clone C_D5]; or (c) the amino acid sequences GFSFSTSGYGVS (SEQ ID NO: 51) (HCDR1), LAHIWWDDEKYYVDSVKG (SEQ ID NO: 52) (HCDR2), NRRYFPFAY (SEQ ID NO: 45) (HCDR3), RASQNVGTNLA (SEQ ID NO: 43) (LCDR1), SASYRAS (SEQ ID NO: 53) (LCDR2) and QQYSTDPLT (SEQ ID NO: 34) (LCDR3) [Clone C_F2]; or (d) the amino acid sequences GFSLSTSGMGVS (SEQ ID NO: 54) (HCDR1), VAHIWWDDEKYYVDSVKG (SEQ ID NO: 55) (HCDR2), NRRYFPFAY (SEQ ID NO: 45) (HCDR3), RASQSVGSNLA (SEQ ID NO: 32) (LCDR1), SASYRAT (SEQ ID NO: 46) (LCDR2) and QQYSTDPLT (SEQ ID NO: 34) (LCDR3) [Clone F_B11]; or (e) the amino acid sequences GFSFSTSGMGVS (SEQ ID NO: 56) (HCDR1), VAHIWWDDEKYYVDSVKG (SEQ ID NO: 55) (HCDR2), NRRYFPFAY (SEQ ID NO: 45) (HCDR3), RASQSVGSNVA (SEQ ID NO: 57) (LCDR1), SASNRYT (SEQ ID NO: 44) (LCDR2) and QQYSTDPLT (SEQ ID NO: 34) (LCDR3) [Clone F_B9]; or (f) the amino acid sequences GFSLSTSGMGMG (SEQ ID NO: 58) (HCDR1), LAHIWWDDDKYYVDSVKG (SEQ ID NO: 26) (HCDR2), SRRYFPFAY (SEQ ID NO: 59) (HCDR3), RASQNVGSNLA (SEQ ID NO: 40) (LCDR1), SASYRYT (SEQ ID NO: 33) (LCDR2) and QQYSTDPLT (SEQ ID NO: 34) (LCDR3) [Clone H_A3]; or (g) the amino acid sequences GFSLSTSSYGVS (SEQ ID NO: 60) (HCDR1), VAHIWWDDEKYYVDSVKG (SEQ ID NO: 55) (HCDR2), TRLYFPFAY (SEQ ID NO: 39) (HCDR3), RASQSVGTNLA (SEQ ID NO: 36) (LCDR1), SASYRYT (SEQ ID NO: 33) (LCDR2) and QQYSNDPLT (SEQ ID NO: 38) (LCDR3) [Clone J_C5]; or (h) the amino acid sequences GFSLSTSGMGMS (SEQ ID NO: 61) (HCDR1), LAHIWWDDEKYYVDSVKG (SEQ ID NO: 52) (HCDR2), NRRYFPFAY (SEQ ID NO: 45) (HCDR3), RASQSVGTNVA (SEQ ID NO: 49) (LCDR1), SASYRAS (SEQ ID NO: 53) (LCDR2) and QQYSTDPLT (SEQ ID NO: 34) (LCDR3) [Clone K_A12]; or (i) the amino acid sequences GFSLSTSGYGMS (SEQ ID NO: 62) (HCDR1), VAHIWWDDEKYYVDSVKG (SEQ ID NO: 55) (HCDR2), TRQYFPFAY (SEQ ID NO: 31) (HCDR3), RASQSVGSNLA (SEQ ID NO: 32) (LCDR1), SASYRAT (SEQ ID NO: 46) (LCDR2) and QQYSTDPLT (SEQ ID NO: 34) (LCDR3) [Clone MH]; or (j) the amino acid sequences GFSLSTSGMGMS (SEQ ID NO: 61) (HCDR1), VAHIWWDDEKYYVDSVKG (SEQ ID NO: 55) (HCDR2), TRQYFPFAY (SEQ ID NO: 31) (HCDR3), RASQSVGSNLA (SEQ ID NO: 32) (LCDR1), SASYRAT (SEQ ID NO: 46) (LCDR2) and QQYSTDPLT (SEQ ID NO: 34) (LCDR3) [Clone MH-1]; or (k) the amino acid sequences GFSLSTSGYGVS (SEQ ID NO: 47) (HCDR1), VAHIWWDDEKYYVDSVKG (SEQ ID NO: 55) (HCDR2), TRQYFPFAY (SEQ ID NO: 31) (HCDR3), RASQSVGSNLA (SEQ ID NO: 32) (LCDR1), SASYRAT (SEQ ID NO: 46) (LCDR2) and QQYSTDPLT (SEQ ID NO: 34) (LCDR3) [Clone MH-2]; or (l) the amino acid sequences GFSLSTSGYGMS (SEQ ID NO: 62) (HCDR1), VAHIWWDDEKYYVDSVKG (SEQ ID NO: 55) (HCDR2), TRQYFPFAY (SEQ ID NO: 31) (HCDR3), RASQNVGSNLA (SEQ ID NO: 40) (LCDR1), SASYRAT (SEQ ID NO: 46) (LCDR2) and QQYSTDPLT (SEQ ID NO: 34) (LCDR3) [Clone MH-3]; or (m) the amino acid sequences GFSLSTSGYGMS (SEQ ID NO: 62) (HCDR1), VAHIWWDDEKYYVDSVKG (SEQ ID NO: 55) (HCDR2), TRQYFPFAY (SEQ ID NO: 31) (HCDR3), RASQSVGSNVA (SEQ ID NO: 57) (LCDR1), SASYRAT (SEQ ID NO: 46) (LCDR2) and QQYSTDPLT (SEQ ID NO: 34) (LCDR3) [Clone MH-4]; or (n) the amino acid sequences GFSLSTSGYGMS (SEQ ID NO: 62) (HCDR1), VAHIWWDDEKYYVDSVKG (SEQ ID NO: 55) (HCDR2), TRQYFPFAY (SEQ ID NO: 31) (HCDR3), RASQSVGSNLA (SEQ ID NO: 32) (LCDR1), SASYRYT (SEQ ID NO: 33) (LCDR2) and QQYSTDPLT (SEQ ID NO: 34) (LCDR3) [Clone MH-5]; or (o) the amino acid sequences GFSLSTSGYGVG (SEQ ID NO: 29) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASNRYT (SEQ ID NO: 44) (LCDR2) and QQYSTNPLT (SEQ ID NO: 63) (LCDR3) [Clone A6.2]; or (p) the amino acid sequences GFSLSTSGYGVS (SEQ ID NO: 47) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASNRYT (SEQ ID NO: 44) (LCDR2) and QQYSTDPLT (SEQ ID NO: 34) (LCDR3) [Clone A6.3]; or (q) the amino acid sequences GFSLSTSGYGMS (SEQ ID NO: 62) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASNRYT (SEQ ID NO: 44) (LCDR2) and QQYSTDPLT (SEQ ID NO: 34) (LCDR3) [Clone A6.4]; or (r) the amino acid sequences GFSLSTSGYGMG (SEQ ID NO: 64) (HCDR1), LAHIWWDDDKYYVDSVKG (SEQ ID NO: 26) (HCDR2), TRQYFPFAY (SEQ ID NO: 31) (HCDR3), RASQSVGSNLA (SEQ ID NO: 32) (LCDR1), SASNRYT (SEQ ID NO: 44) (LCDR2) and QQYSTDPLT (SEQ ID NO: 34) (LCDR3) [Clone A6.5].

In other specific embodiments of the invention, the antibody molecule or antigen-binding portion thereof may comprise the HCDR1-3 and LCDR1-3 sequences recited for further individual clones identified in Tables 3 and 4 below.

Where a specific clone include an underscore in their name, the underscore may be replaced by a hyphen for the same clone. For example, the names "D_A6" and "D-A6" refer to the same clone, and these names are used interchangeably herein.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 6C8 murine LCDR1 (as defined herein, i.e. the amino acid sequence KASQNVGTNVA (SEQ ID NO: 13)) has been identified to have a putative O-link glycosylation site at residue 8 (T). Removal of this site, for example by conservative substitution (such as to S, A or N), is envisaged (as for example in clone D_A6 and other clones in Tables 3 and 4).

Similarly, the 6C8 murine LCDR3 (as defined herein, i.e. the amino acid sequence QQYNTDPLT (SEQ ID NO: 15)) has been identified to have a putative deamidation site at residue 4 (N). Removal of this site, for example by conservative substitution (such as to S, H, D, T, K, G, E, Q or R), is envisaged (as for example in clone D_A6 and other clones in Tables 3 and 4).

Also by way of example, the 6C8 murine HCDR1 (as defined herein, i.e. the amino acid sequence GFSLSTSGMGVG (SEQ ID NO: 4)) has been identified to have a putative oxidation site at residue 9 (M). Removal of this site, for example by substitution to any amino acid (such as to Y, F, L or W), is envisaged (as for example in clone D_A6 and other clones in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted.

The antibody molecule or antigen-binding portion thereof may comprise an IGHV3-7 human germline scaffold into which the corresponding HCDR sequences have been inserted.

The antibody molecule or antigen-binding portion thereof may comprise an IGKV3-11 human germline scaffold into which the corresponding LCDR sequences have been inserted.

The antibody molecule or antigen-binding portion thereof may comprise an immunologically inert constant region.

The antibody molecule or antigen-binding portion thereof may be a Fab fragment, a F(ab)$_2$ fragment, an Fv fragment, a tetrameric antibody, a tetravalent antibody, a multispecific antibody (for example, a bivalent antibody), a domain-specific antibody, a single domain antibody, a monoclonal antibody or a fusion protein. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the antifolates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein.

Further provided is a vector comprising the nucleic acid molecule of the invention as defined herein.

Also provided is a host cell comprising the nucleic acid molecule or the vector of the invention as defined herein.

In a further aspect there is provided a method of producing an anti-GITR antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

The cancer may for example be selected from the group consisting of: pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The pharmaceutical composition of the invention may comprise a pharmaceutically acceptable excipient. A pharmaceutically acceptable excipient may be a compound or a combination of compounds entering into a pharmaceutical composition which does not provoke secondary reactions and which allows, for example, facilitation of the administration of the anti-GITR antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-GITR antibody molecule.

In some embodiments, the anti-GITR antibody molecule may be provided in a lyophilised form for reconstitution prior to administration. For example, lyophilised antibody molecules may be re-constituted in sterile water and mixed with saline prior to administration to an individual.

The anti-GITR antibody molecules will usually be administered in the form of a pharmaceutical composition, which may comprise at least one component in addition to the antibody molecule. Thus pharmaceutical compositions may comprise, in addition to the anti-GITR antibody molecule, a pharmaceutically acceptable excipient, carrier, buffer, stabilizer or other materials well known to those skilled in the art. Such materials should be non-toxic and should not interfere with the efficacy of the anti-GITR antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-GITR antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-GITR antibody molecule may be administered alone or in combination with other treatments, either simultaneously or sequentially dependent upon the condition to be treated.

An anti-GITR antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-GITR antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmacokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-GITR antibody molecules as described herein may be administered as sub-cutaneous injections. Sub-cutaneous injections may be administered using an auto-injector, for example for long term prophylaxis/treatment.

In some preferred embodiments, the therapeutic effect of the anti-GITR antibody molecule may persist for several half-lives, depending on the dose. For example, the therapeutic effect of a single dose of the anti-GITR antibody molecule may persist in an individual for 1 month or more, 2 months or more, 3 months or more, 4 months or more, 5 months or more, or 6 months or more.

The invention also provides a method of producing an antibody molecule which specifically binds to human GITR and optionally also cynomolgus monkey GITR, or an antigen-binding portion thereof, comprising the steps of:

(1) grafting anti-GITR CDRs from a non-human source into a human v-domain framework to produce a humanized anti-GITR antibody molecule or antigen-binding portion thereof;

(2) generating a phage library of clones of the humanized anti-GITR antibody molecule or antigen-binding portion thereof comprising one or more mutations in the CDRs;

(3) screening the phage library for binding to human GITR and optionally also cynomolgus monkey GITR;

(4) selecting clones from the screening step (3) having binding specificity to human GITR and optionally also cynomolgus monkey GITR; and (5) producing an antibody molecule which specifically binds to human GITR and optionally also cynomolgus monkey GITR or an antigen-binding portion thereof from clones selected from step (4).

Refinements applicable to the above method are as described in Example 1 below.

As used herein, the terms "glucocorticoid-induced TNF receptor" and "GITR" refer to glucocorticoid-induced TNF receptor and variants thereof that retain at least part of the biological activity of GITR. As used herein, GITR includes all mammalian species of native sequence GITR, including human, rat, mouse and chicken. The term "GITR" is used to include variants, isoforms and species homologs of human GITR. Antibodies of the invention may cross-react with GITR from species other than human, in particular GITR from cynomolgus monkey (*Macaca fascicularis*). In certain embodiments, the antibodies may be completely specific for human GITR and may not exhibit non-human cross-reactivity.

As used herein, an "antagonist" as used in the context of the antibody of the invention or an "anti-GITR antagonist antibody" (interchangeably termed "anti-GITR antibody") refers to an antibody which is able to bind to GITR and inhibit GITR biological activity and/or downstream pathway(s) mediated by GITR signalling. An anti-GITR antagonist antibody encompasses antibodies that can block, antagonize, suppress or reduce (including significantly) GITR biological activity, including downstream pathways mediated by GITR signalling, such as receptor binding and/or elicitation of a cellular response to GITR. For the purposes of the present invention, it will be explicitly understood that the term "anti-GITR antagonist antibody" encompass all the terms, titles, and functional states and characteristics whereby GITR itself, and GITR biological activity (including but not limited to its ability to enhance the activation of Teffs and reduce the activity of Tregs), or the consequences of the activity or biological activity, are substantially nullified, decreased, or neutralized in any meaningful degree.

GITR "specifically binds" "specifically interacts", "preferentially binds", "binds" or "interacts" with GITR if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to GITR. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. When choosing FR to flank CDRs, for example when humanizing or optimizing an antibody, FRs from antibodies which contain CDR sequences in the same canonical class are preferred. Such FRs may nevertheless be modified for example by mutation or deletion, including by increasing or shortening their length if required.

The "Unified" CDR definition used in the present application combines the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (when referred to as the "Unified" definition or "Ours") incorporates the lessons of all such prior insights and includes all appropriate loop positions required to sample the full residue landscape that potentially mediates target-binding complementarity.

Table 1 shows the amino acid sequences of the 6C8 murine anti-GITR antibody CDRs as defined herein according to the "Unified" definition, in comparison to well-known alternative systems for defining the same CDRs. Antibody molecules of antigen-binding portions thereof of the present invention may be defined using any of the CDR definitions set out in Table 1.

For reference purposes, the full classical Kabat numbering for the C68 murine anti-GITR antibody heavy and light chains variable regions (as disclosed in WO2016/105021) is as follows.

Variable Heavy Chain:
H1 Q, H2 V, H3 T, H4 L, H5 K, H6 E, H7 S, H8 G, H9 P, H10 G, H11 I, H12 L, H13 K, H14 P, H15 S, H16 Q, H17 T, H18 L, H19 S, H20 L, H21 T, H22 C, H23 S, H24 F, H25 S, H26 G, H27 F, H28 S, H29 L, H30 S, H31 T, H32 S, H33 G, H34 M, H35 G, H35A V, H35B G, H36 W, H37 I, H38 R, H39 Q, H40 P, H41 S, H42 G, H43 K, H44 G, H45 L, H46 E, H47 W, H48 L, H49 A, H50 H, H51 I, H52 W, H53 W, H54 D, H55 D, H56 D, H57 K, H58 Y, H59 Y, H60 N, H61 P, H62 S, H63 L, H64 K, H65 S, H66 Q, H67 L, H68 T, H69 I, H70 S, H71 K, H72 D, H73 T, H74 S, H75 R, H76 N, H77 Q, H78 V, H79 F, H80 L, H81 K, H82 I, H82A T, H82B S, H82C V, H83 D, H84 T, H85 A, H86 D, H87 A, H88 A, H89 T, H90 Y, H91 Y, H92 C, H93 A, H94 R, H95 T, H96 R, H97 R, H98 Y, H99 F, H100 P, H100A F, H101 A, H102 Y, H103 W, H104 G, H105 Q, H106 G, H107 T, H108 L, H109 V, H110 T, H111 V, H112 S, H113 S, H114-.

Variable Light Chain:
L1 D, L2 I, L3 V, L4 M, L5 T, L6 Q, L7 S, L8 Q, L9 K, L10 F, L11 M, L12 S, L13 T, L14 S, L15 V, L16 G, L17 D, L18 R, L19 V, L20 S, L21 V, L22 T, L23 C, L24 K, L25 A, L26 S, L27 Q, L28 N, L29 V, L30 G, L31 T, L32 N, L33 V, L34 A, L35 W, L36 Y, L37 Q, L38 Q, L39 K, L40 P, L41 G, L42 Q, L43 S, L44 P, L45 K, L46 A, L47 L, L48 I, L49 Y, L50 S, L51 A, L52 S, L53 Y, L54 R, L55 Y, L56 S, L57 G, L58 V, L59 P, L60 D, L61 R, L62 F, L63 T, L64 G, L65 S, L66 G, L67 S, L68 G, L69 T, L70 D, L71 F, L72 T, L73 L, L74 T, L75 I, L76 N, L77 N, L78 V, L79 H, L80 S, L81 E, L82 D, L83 L, L84 A, L85 E, L86 Y, L87 F, L88 C, L89 Q, L90 Q, L91 Y, L92 N, L93 T, L94 D, L95 P, L96 L, L97 T, L98 F, L99 G, L100 A, L101 G, L102 T, L103 K, L104 L, L105 E, L106 I, L107 K.

As used herein the term "conservative substitution" refers to replacement of an amino acid with another amino acid which does not significantly deleteriously change the functional activity. A preferred example of a "conservative substitution" is the replacement of one amino acid with another amino acid which has a value 0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| Y | −2 | −2 | −2 | −3 | −2 | −1 | −2 | −3 | 2 | −1 | −1 | −2 | −1 | 3 | −3 | −2 | −2 | 2 | 7 | −1 |
| V | 0 | −3 | −3 | −3 | −1 | −2 | −2 | −3 | −3 | 3 | 1 | −2 | 1 | −1 | −2 | −2 | 0 | −3 | −1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to GITR and is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen GITR to inhibit 50% of activity measured in a GITR activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to GITR.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neo-adjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-GITR Therapeutic Antibodies

Introduction

In this example, we successfully generate a panel of agonistic, optimized anti-GITR antibodies. These anti-GITR antibodies are well expressed, biophysically stable, highly soluble and of maximized identity to preferred human germlines.

Materials and Methods

IgG Cloning, Transient Expression, Purification

Antibody v-domain encoding DNA sequences were cloned via restriction-ligation cloning into separate IgG heavy and light-chain expression cassettes in separate plasmid vectors. IgGs were transiently expressed in HEK-293expi cells after transfection with endotoxin-free IgG expression plasmid preparations, per manufacturer's protocols. IgGs were purified using a single-step protocol: Conditioned media were loaded (neat) onto a 1 ml ProA sepharose column, pre-equilibrated in PBS pH7.4. The column was washed with 5 column volumes of PBS pH7.4, before the protein was eluted with 100 mM glycine, pH 2.7 and subjected to dialysis in PBS pH 7.4 using 30 kDa cutoff dialysis membrane.

IgG Titration Binding ELISAs

To coat Greiner Bio-One High bind ELISA plates, target proteins were diluted to 1 µg/ml in carbonate buffer and added at 100 µl per well, at 4° C., o/n. Coated plates were washed 3× with PBS pH7.4, blocked with 1% BSA in PBS (380 µl/well) for 1 hr at RT, then washed 3× with PBS-Tween 20 (PBST). GITR antibodies (100 µl/well; diluted in PBST) were then added and then incubated 1 hr at RT. Plates were then washed 3× with PBST and goat anti-human kappa chain-HRP added (100 µl/well) at RT, for 1 hr. Plates were then washed 3× with PBST and twice with PBS before the addition of 100 µl TMB per well. Reactions were stopped by adding 100 µl 2M $H_2SO_4$/well and OD was read on a plate reader at 450 nm. IgG binding analysis via ELISA on negatively charged biomolecular surfaces were performed as previously described (see Mouquet et al., 2010, Nature 467: 591-595).

GITR Cell-Based Assays

The GITR Bioassay Kit (CS184006) from Promega was used to analyse anti-GITR IgGs for their ability to cross-link GITR and agonise the receptor. This assay is based on "GloResponse" NFkB-luc2/GITR Jurkat cells. The assay was performed per the manufacturer's instructions, using HA-tagged human GITRL protein plus anti-HA tag antibody as positive control. A human IgG1 with specificity for an unrelated receptor was used as the isotype negative control.

The ADCC Bioassay Kit (G7015) from Promega was used to analyse anti-GITR IgGs for their ability to induce ADCC after binding human or cyno GITR-expressing CHO-K1 cells. This assay is based on engineered Jurkat effector cells stably expressing the FcγRIIIa receptor, V158 (high affinity) variant, and an NFAT response element driving expression of firefly luciferase. The assay was performed per the manufacturer's instructions, using anti-GITR antibodies in both IgG1 and aglycosylated IgG1 forms.

G-VL1-VH3 Library Generation and Selection

The G-VL2-VH3 scFv repertoire was assembled by mass oligo synthesis and PCR. The amplified scFv repertoire was then cloned via restriction-ligation into a phagemid vector, transformed into E. coli TG-1 cells, characterized and the phage repertoire rescued essentially as previously described in detail (Finlay et al., 2011, Methods Mol Biol 681: 383-401).

Phage selections were performed by coating streptavidin magnetic microbeads with GITR-Fc protein (either human or cyno), washing the beads thrice with PBS and resuspending in PBS pH7.4 plus 5% skim milk protein (MPBS). These beads were coated at 200 nM target protein in round 1 of selection, followed by 100, 50 and 10 nM in subsequent rounds.

HTRF Binding Competition Assay

A competition HTRF assay was established to examine epitope competition against VH1/VL1 IgG by grafted and library-derived clones. The purified VH1/VL1 IgG was labelled with terbium using a labelling kit (CisBio) per the manufacturer's instructions. The final reaction mix contained biotinylated human GITR-Fc, SA-XL665 (CisBio), terbium-labelled parental XT-M4, and competitor IgG of interest, prepared as described above, in a total reaction volume of 20 µl in 1× assay buffer [50 mM sodium phosphate, pH 7.5, 400 mM potassium fluoride, and 0.1% BSA (w/v)]. Reagents were added sequentially on a MiniTrak Liquid Handling Platform (Perkin-Elmer) into 384-well low-volume black plates (Nunc). Reactions proceeded for 1 h at room temperature, and plates were subsequently read on a plate reader with excitation at 340 nm and two emission readings at 615 nm (measuring input donor fluorescence from VH1-VL1-cryptate) and 665 nm (measuring output acceptor fluorescence from SAXL665). Readings were expressed as 665 nm/615 nm ratios.

Binding Specificity Analyses

Anti-GITR antibodies were tested for polyreactivity by ELISA. Purified, recombinant, target and non-target antigens were coated in 96-well Nunc maxisorp plates at 100 ng per well in carbonate buffer, at 4° C. overnight. Plates were then washed 3× with PBS, blocked with 1% BSA in PBS, then washed 3× with PBS-Tween20. A dilution series of primary antibodies was then applied, plates were washed 3× with PBS-Tween20 followed by application of goat anti-human kappa chain-HRP 1:4,000 secondary antibody. Wells were then washed 3× with PBS-Tween20 and 2× with PBS, 100 µl TMB peroxidase substrate was added per well, the was reaction stopped by adding 100 µl 2M $H_2SO_4$ and absorbances were read at 450 nm.

Anti-GITR antibodies were also tested for binding specificity by flow cytometry. HuT78 cells were activated by incubation with anti-CD3/anti-CD28 beads for 3 days. Naïve cells were incubated in media alone. At the end of the incubation the cells were harvested and the beads removed from the activated cells using a magnet. Cells were incubated with viability dye and then stained with anti-GITR antibodies at 4° C. Commercially available anti-human GITR monoclonal antibody 108-17 (directly labelled with PE; obtained from BioLegend Inc., Cat. #371202) was also included as positive controls. Binding of VH1/VL1 and D-A6 IgG1 proteins were detected by subsequent incubation with a PE labelled goat anti-human IgG. Cells were fixed with 4% PFA before being stored in PBS at 4° C. overnight. Cells were analysed the next day using a BD Fortessa flow cytometer running Diva software. Analysis was performed using FlowJo software. Single cells were gated by scatter and live cells using the viability dye. The median fluorescence intensity (MFI) in the PE channel of the single live cells was determined and plotted. Each staining condition was performed in duplicate.

Biacore Affinity Analysis of Anti-GITR Fab Fragments

As both IgG1 and GITR-Fc proteins are multimeric, achieving accurate 1:1 binding affinity measurements via surface plasmon resonance (SPR) is challenging. To minimise this issue, monomeric Fab fragments ("Fabs") were prepared from both the VH1/VL1 and D-A6 IgG1 proteins, using the GingisKHAN kit (Genovis). Fabs were then buffer exchanged into HBE-EP buffer for use in Biacore analyses.

For affinity estimation, anti-human IgG Fc antibody was amine coupled at pH 5 onto three flow cells (Fc 1 to Fc 3) of a Biacore CM5 chip. The level of anti-Fc antibody immobilised onto the chip was approximately 550 RU. Human and cyno GITR-Fc and irrelevant receptor-Fc proteins were then captured onto the anti-Fc antibodies (by injecting over the antibody surface until nearly/completely saturated) in order that 80-100 RU were captured. Fab monomers were then injected over the Fc proteins captured on the chip at 37° C. a flow rate of 50 µl/min for 120 seconds, followed by Biacore running buffer (HBS-EP) being flowed over the chip for 240 seconds at 50 µl/min. The chip was regenerated between cycles using 2×15 second injections of 10 mM Glycine pH 2. The concentrations of Fab samples tested were 400, 200, 100, 50, 25, 12.5, and 6.25 nM. A Biacore running buffer control (0 nM) was also included as a control.

Results and Discussion

CDR Grafting onto Preferred Human Germline v-Genes

The CDRs of an agonistic murine anti-GITR IgG 6C8 (mVH/mVL; see WO2006/105021 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds which are known to have high stability and are used at high frequency in the expressed human antibody repertoire.

As a reference molecule we also grafted the CDRs to closest germline frameworks (hVH1/VL1). Those scaffolds and grafted CDR definitions are outlined in Table 2. The heavy and light chain sequences for murine anti-GITR antibody are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. In this study, this process was further complicated by the fact that the parental antibody uses a canonical HCDR1 structure (H1-15-1), which is used at low frequency in the human antibody repertoire. This observation might lead the skilled person to an assumption that the antibodies should be humanized onto "closest germline" sequences (those human germlines with closest amino acid homology), but the closest heavy chain germline (IGHV2-70) is rarely used in the functionally-expressed human antibody repertoire, making the resulting antibodies at risk of unfavourable pharmacological and manufacturing qualities.

Seven v-domain grafts (4 VH, 3 VL) were designed in silico, using CDR definitions as outlined in Table 1. The v-domain gene sequences of the grafted and mVH/mVL v-domains were synthesized as double-stranded DNA cassettes and cloned into plasmids designed for the expression of full-length human IgG1 antibodies. These plasmids were used to perform transient transfection of HEK-293 cells and the expressed IgGs purified via protein A column. To test all possible combinations of CDR-grafted v-domains for function, all 4 humanized heavy chains were co-expressed with each of the 3 humanized light chains, making 12 IgGs grouped into 4 families (VH1-4).

Figure 1B:
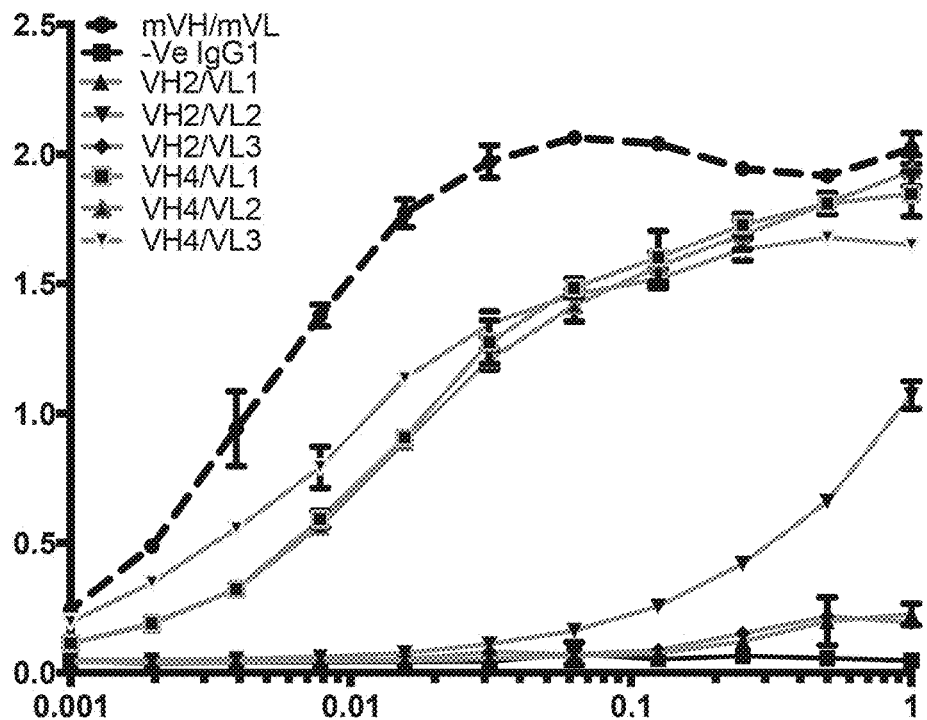

Retention of GITR-binding function in the purified IgG1 proteins was first examined by titration in direct binding ELISA against human GITR-Fc. These experiments showed impaired target binding in comparison to the mVH/mVL IgG ($EC_{50} \geq 0.004$ µg/ml) for the VH2 and VH4 families, with all binding function being essentially ablated in the VH2 family (FIG. 1B). This finding demonstrated that the CDRs of the parental antibody could not simply be grafted into any randomly-chosen human v-domain framework, if function was to be retained. Importantly, the >100-fold loss of binding function in the VH2 IgG family further illustrated that the HCDR1 could not be fully germ-lined a priori to match the native sequence of the human germline HCDR1 found in the framework used for grafting (IGHV3-7). Binding function equivalent to, or improved over, the mVH/mVL IgG1 was observed for antibodies in the VH1 and VH3 families (FIG. 1A).

Figure 2:
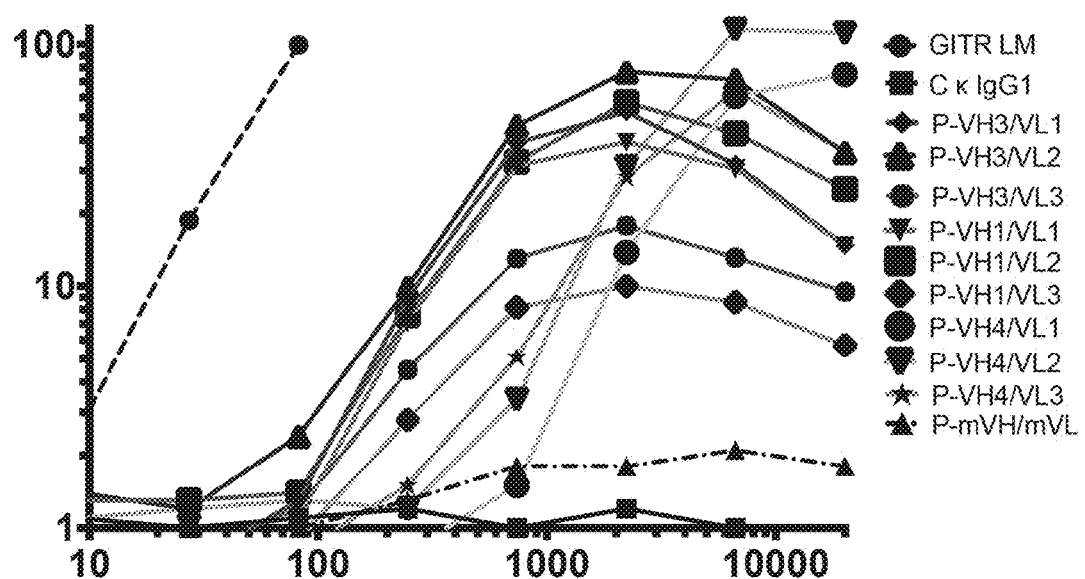
FIG. 2. GITR Jurkat cell reporter assay (GITR agonism). Human germline grafted antibodies in human IgG1 format were applied in the Promega GITR+ Jurkat cell reporter assay. This assay showed that amongst the IgGs in graft families VH1, VH3 and VH4, clone VH3/VL2 exhibited the most potent, concentration-dependent agonistic activity. The VH2 family of grafts were omitted due to lack of effective target binding by ELISA. X-axis shows concentration of mAb in ng/ml, and Y-axis shows fold induction. In the figure legend, "LM" refers to ligand multimer and "C" refers to control.

Based on the ELISA binding data, the mVH/mVL, VH1, VH3 and VH4 family IgGs were tested for concentration-dependent agonist activation of GITR in a cell-based recombinant receptor reporter assay. This assay demonstrated that the VH3/VL2 combination gave the strongest concentration-dependent receptor activation (FIG. 2). This graft was therefore taken forward as the template for CDR mutagenesis and selection of improved clones.

Library Generation and Screening

The v-domain sequences VL2 and VH3 were combined into a VL-VH scFv format and a mutagenesis library cassette was generated by mass oligo synthesis and assembly. The final scFv library (named G-VL2-VH3) was ligated into a phage display vector and transformed into E. coli via electroporation to generate $3.0 \times 10^8$ independent clones. Library build quality was verified by deep sequencing >100,000 clones. This sequencing data showed that the positions encoding either the murine or human germline residue at each position of variance had been effectively sampled at a frequency of 50%. Libraries were rescued using helper phage M13 and selections performed on biotinylated human and cynomolgus monkey GITR-Fc proteins.

Figure 3A:
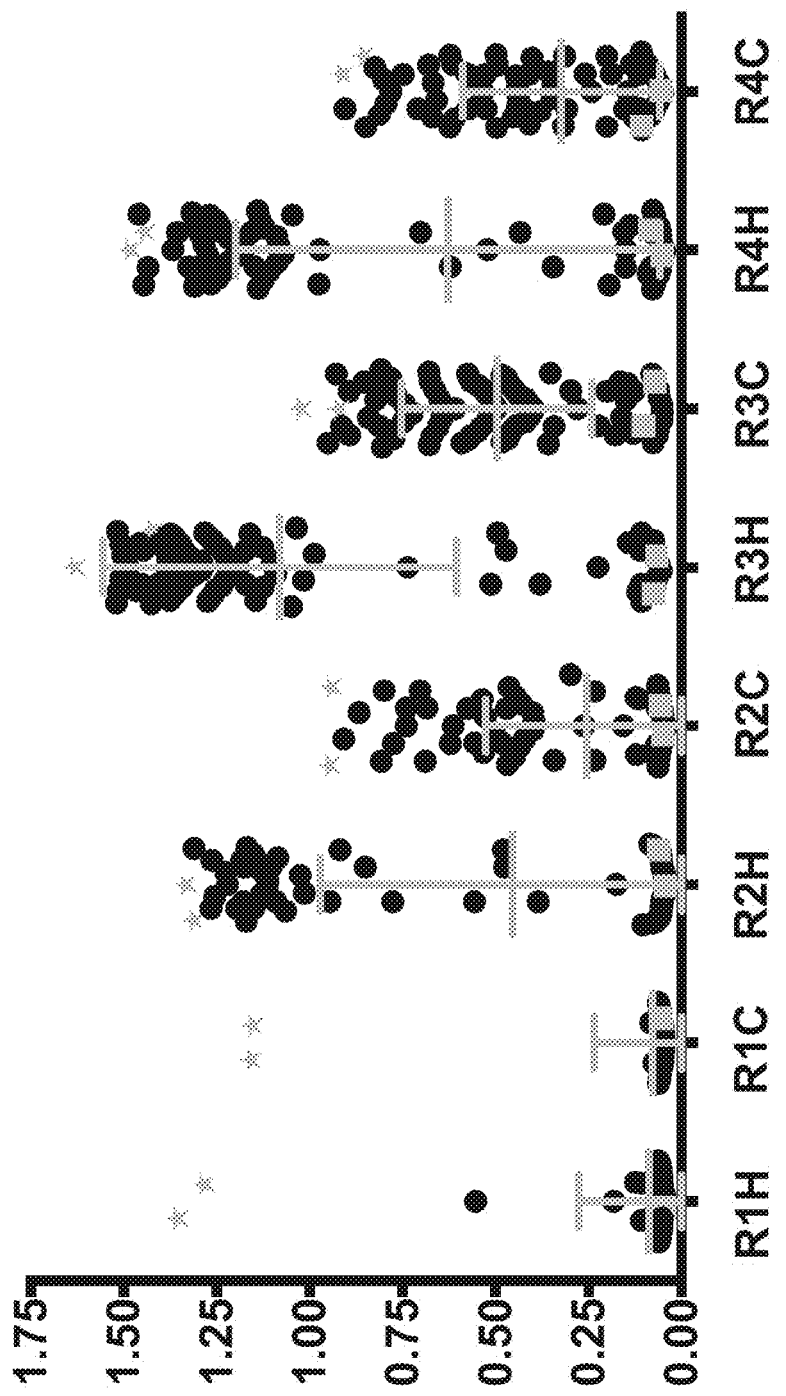
Figure 3C:
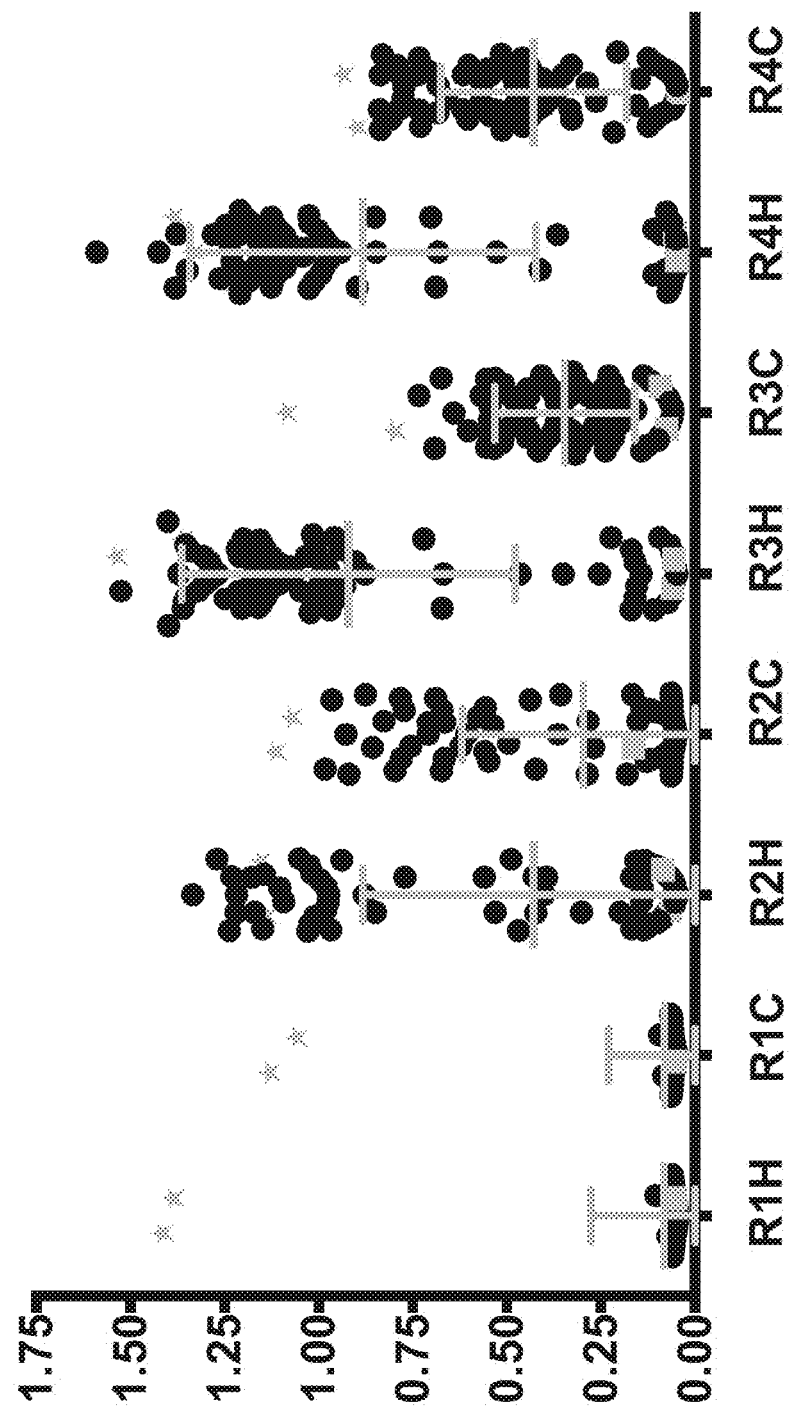

Post-selection screening (FIGS. 3A, B, C) and DNA sequencing revealed the presence of 132 unique, human and cyno GITR-binding, scFv clones with significantly increased human content within the CDRs, while the framework sequences remained fully germline. Of these 132 clones, 74 clones were found to have germ-lining mutations in all CDRs (Table 3). Lead clones were ranked based on level of CDR germ-lining versus ELISA signal for binding to both human and cyno GITR-Fc (FIG. 4). The v-domains of the 11 top clones from this ranking were then sub-cloned into IgG expression vectors for further testing as below (see Table 4).

Figure 5A:
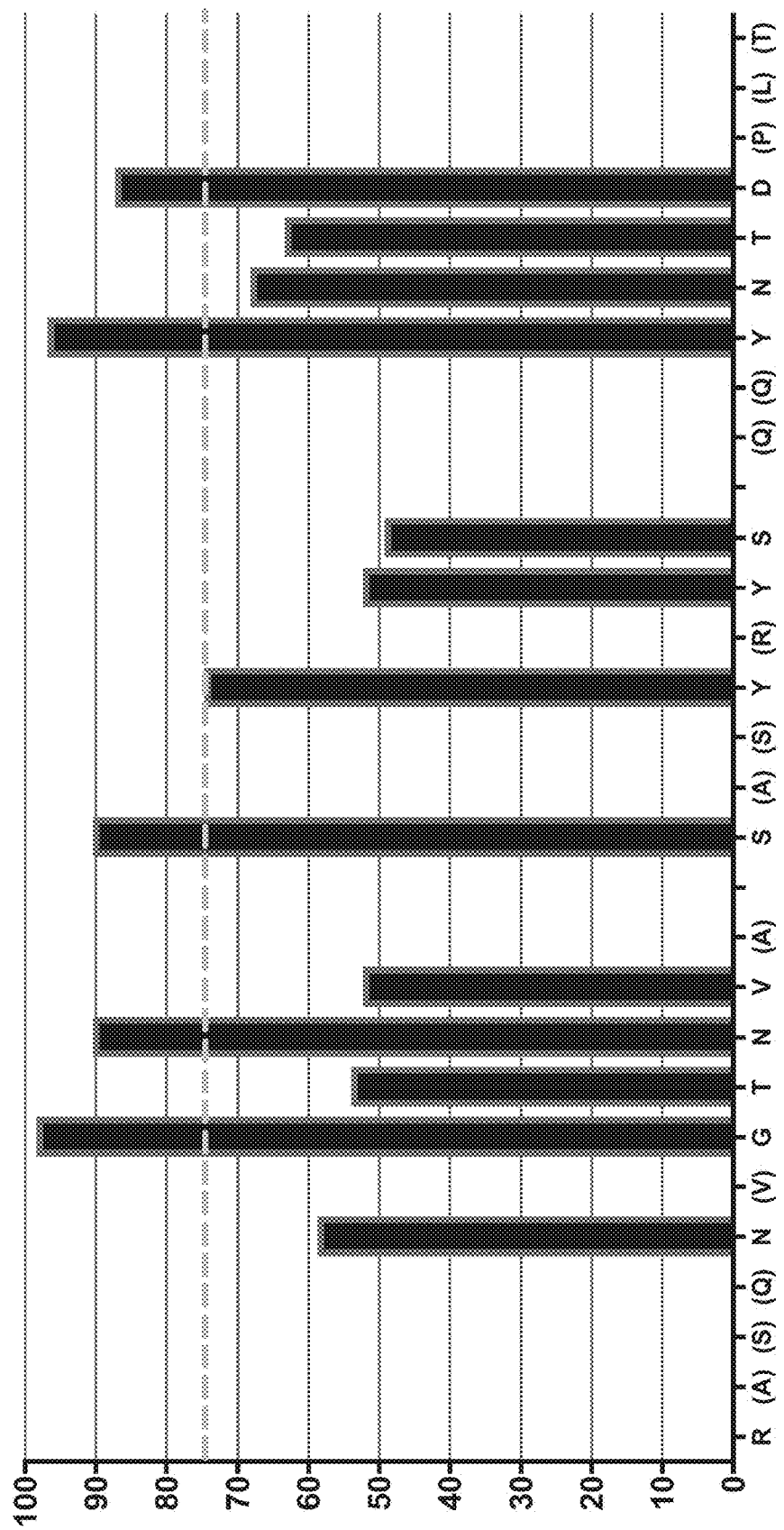
FIG. 5A-5B. Analysis of CDR residue tolerance for mutation to germline. A plot of murine amino acid retention frequencies in the CDRs of the ELISA-positive population of 132 unique GITR-binding scFv clones is shown for (FIG. 5A) $V_L$ (SEQ ID NOs: 145, 14 and 15) and (FIG. 5B) $V_H$ (SEQ ID NOs: 4, 5 and 6) domains, respectively. Only those residues targeted for human/murine residue mutagenesis are plotted, other than in the HCDR3. In each plot, Y-axis shows percentage retention of murine residues and CDR residues are shown in the X-axis. CDR residues noted in parentheses on the X-axes were identical to those found in the human germlines used for grafting (IGKV3-11 and IGHV3-7). Those residues that are not in parentheses, but whose values are set at 0, were mutated to human germline during the grafting process. In both FIG. 5A and FIG. 5B, the dashed line in grey at 75% represents the cutoff for tolerance of murine residue replacement by human germline.
Figure 5B:
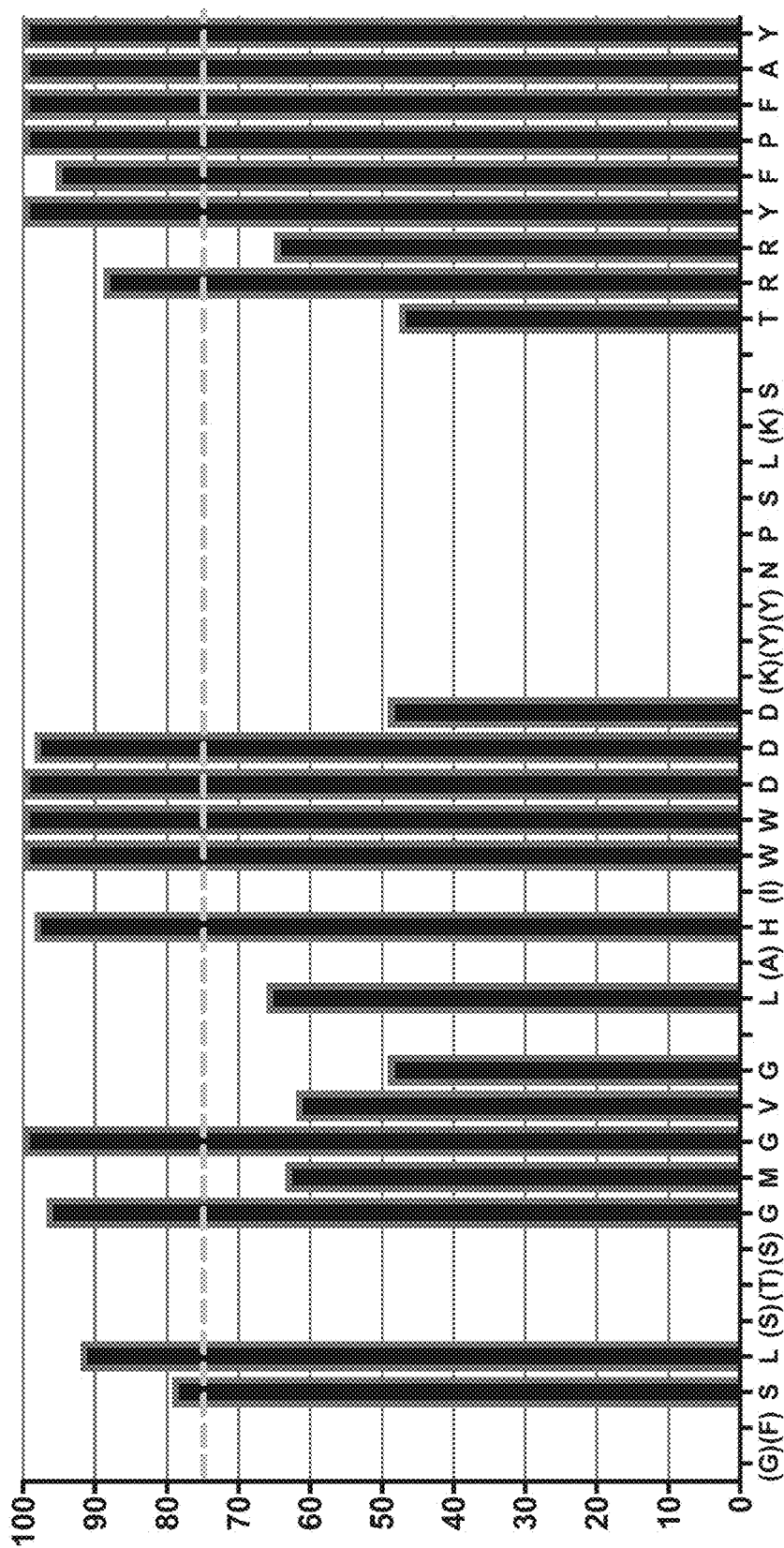

While germ-lining mutations were observed in all CDRs for the lead clones derived directly from library selections, it remained possible that sequence analyses might allow further clones to be designed to have maximal humanization. The 132 sequence-unique hits with binding signals against human and cyno protein were therefore used to analyse the retention frequency (RF) for murine amino acids in the CDRs of this functionally characterized population. Positional amino acid RF was expressed as a percentage found in the VL and VH domains (FIGS. 5A&B). Murine residues with RF<75% were regarded as positions that are not essential to the target-binding paratope and are likely to be open to germ-lining, in a series of combinatorial designs.

A design containing murine residues only with RF>75% was designated "MH" (MH=Maximally Humanized). This clone and 5 further designer clones (MH-1 to MH-5; see Table 4) that added murine residues back into the CDRs were generated by gene synthesis and cloned into human IgG1 expression vectors for production, as with the 11 library-derived clones outlined above. All 17 IgGs were readily expressed and purified from transient transfections of HEK-293 cells. After a single protein A column purification step, analytical HPLC Size Exclusion Chromatography showed all leads to have monomeric IgG content ranging from 97.65 to 99.75%.

Lead IgG Affinity, Stability and Specificity Characteristics

Figure 6C:
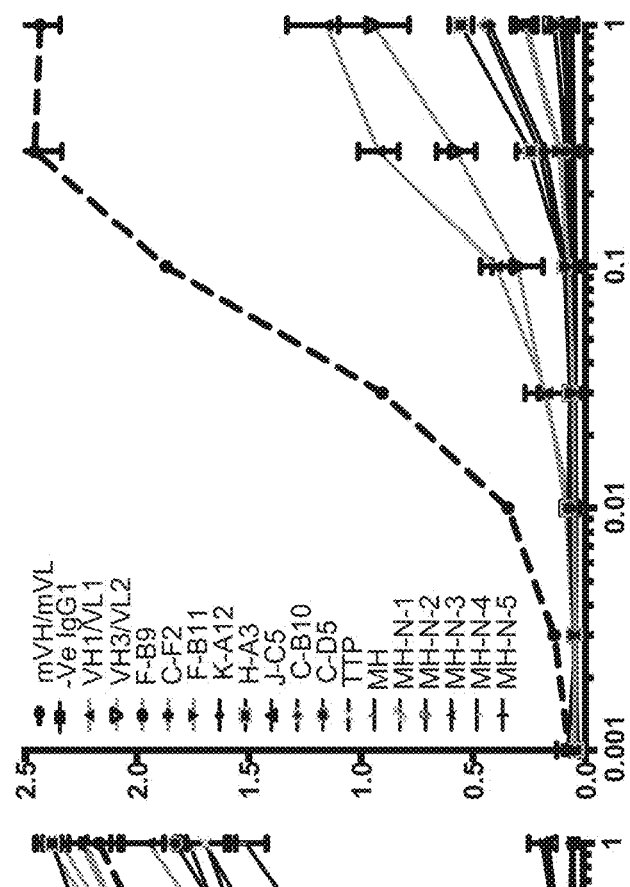
Figure 6D:
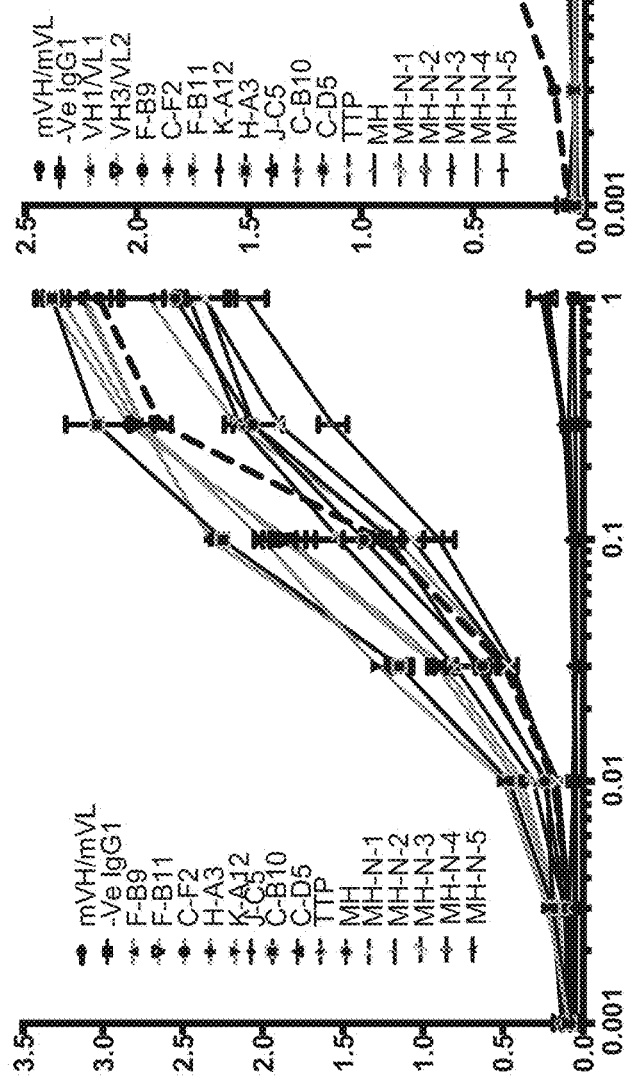
Figure 7A:
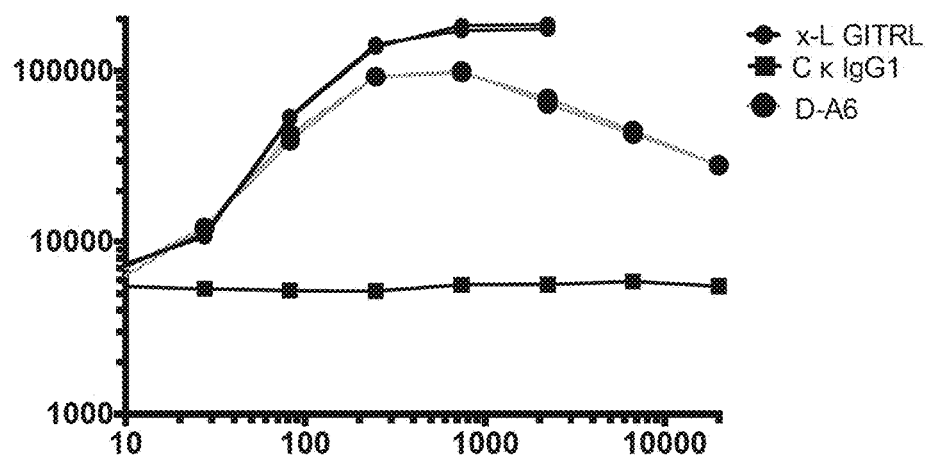
FIG. 7A-7C. GITR Jurkat cell reporter assay for prioritized leads. Duplicate analyses of cross-linking of human GITR at the cell surface for lead clones D-A6 (FIG. 7A), I-C2 (FIG. 7B) and G-G10 (FIG. 7C) in human IgG1 format showed that all 3 clones provoked concentration-dependent agonistic activity in a similar concentration range as anti-HA antibody cross-linked human GITRL protein (x-linked ["x-L"] GITRL), with D-A6 being the closest mimic of ligand activity. In each graph, X-axis shows mAb concentration in ng/ml, Y-axis shows relative light units (RLU), and control K IgG1 is designated "C K IgG1".
Figure 7B:
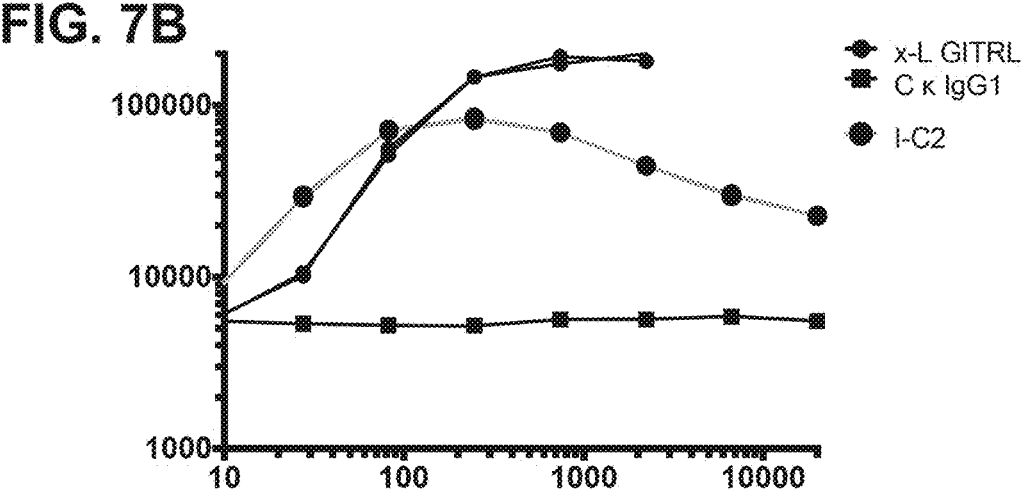
Figure 7C:
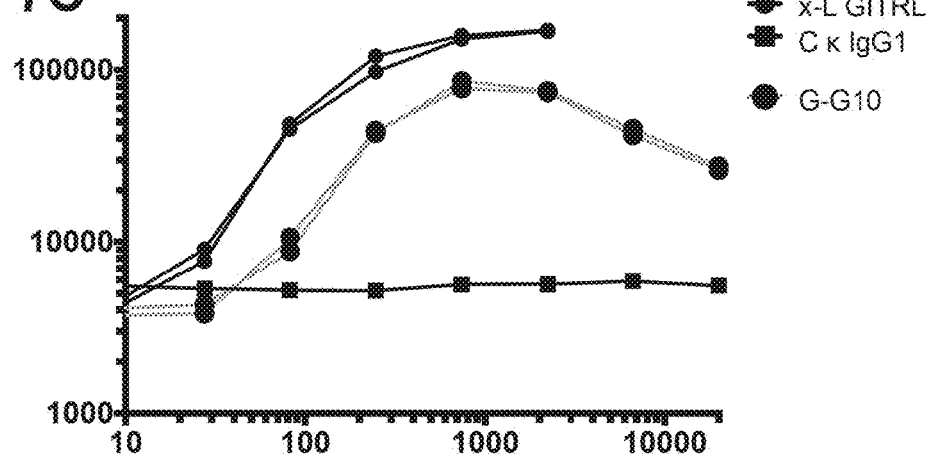

The 17 purified IgGs described above were then tested for binding to human and cyno GITR-Fc in direct titration ELISA format. Surprisingly, this analysis demonstrated that while many (14/17) clones retained binding affinity for human GITR that was comparable to the VH1/VL1 and VH3/VL2 IgGs (including the designer clones MH, MH1-4), only three clones (D-A6, I-C2 and G-G10) maintained comparable or better binding to cyno GITR-Fc (FIG. 6). In the GITR agonism reporter assay, D-A6, I-C2 and G-G10 all also exhibited concentration-dependent receptor activation of human GITR in the same concentration ranges as the antibody cross-linked human GITRL (FIG. 7A-C). Maximum signal for all IgGs and the GITRL was observed at 1000-2000 ng/ml.

To ensure that that lead clones had not suffered from loss of target specificity during the mutation and reselection process; D-A6, I-C2, G-G10, mVH/mVL and VH3/VL2 clones were tested for binding to a panel of 14 purified proteins, including murine GITR-Fc and human TNFRSF members and general immunoglobulin superfamily members (FIG. 8 A-E). All five IgGs exhibited binding signals at 1 µg/ml to GITR-Fc (human OD450 nm>3.0, cyno>1.0), and no detectable binding (OD450 nm<0.1) against any other protein.

HTRF Analysis of Epitope Competition with the VH1/VL1 Human IgG Graft

Figure 9:
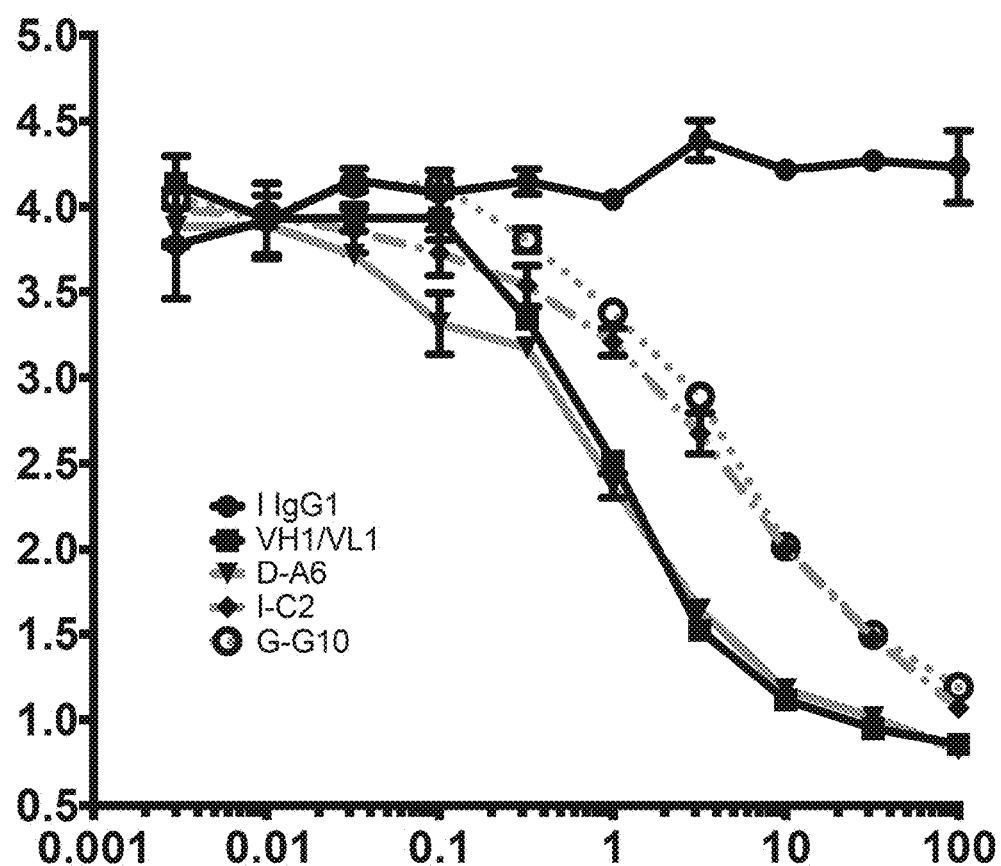
FIG. 9. HTRF competition assay for lead and control IgGs against VH1/VL1 IgG binding to human GITR-Fc. HTRF binding signal for the VH1/VL1 IgG was examined in the presence of titrated competitor IgGs including library-derived leads D-A6, I-C2 and G-G10, Isotype ("I") IgG1 as a negative control, plus unlabeled VH1/VL1 as a positive control. X-axis shows IgG1 concentration in µg/ml and Y-axis shows HTRF 665/615 ratio. All library-derived IgGs demonstrated concentration-dependent reduction in VH1-VL1 binding, suggesting maintenance of a shared epitope.

To examine the competition of the library-derived clones with the unaltered, closest-germline grafted CDRs of VH1/VL1 IgG, an Homogeneous Time Resolved Fluorescence (HTRF) assay was established. This assay incorporated terbium-labelled VH1/VL1 IgG, Biotinylated hGITR-Fc and streptavidin-XL665, in solution-phase binding. Unlabeled IgGs VH1/VL1 (positive control), an isotype control and lead IgGs D-A6, G-G10 and I-C2 were then added across a broad concentration range (0.003-100 µg/ml). IgGs VH1/VL1, D-A6, G-G10 and I-C2 all showed concentration-dependent reduction of binding signal, indicating that they block the binding of VH1/VL1 IgG to GITR (FIG. 9). Importantly, clone D-A6 exhibited an inhibition curve fully overlapping with that of the unlabeled VH1/VL1 IgG in the linear phase, suggesting full maintenance of both affinity and epitope specificity in clone D-A6, despite having 12 CDR mutations (to human germline) in comparison to mVH/mVL.

In Vitro Analysis of Potency of GITR Agonism for D-A6 IgG1 Versus VH1/VL1 IgG1

Figure 11:
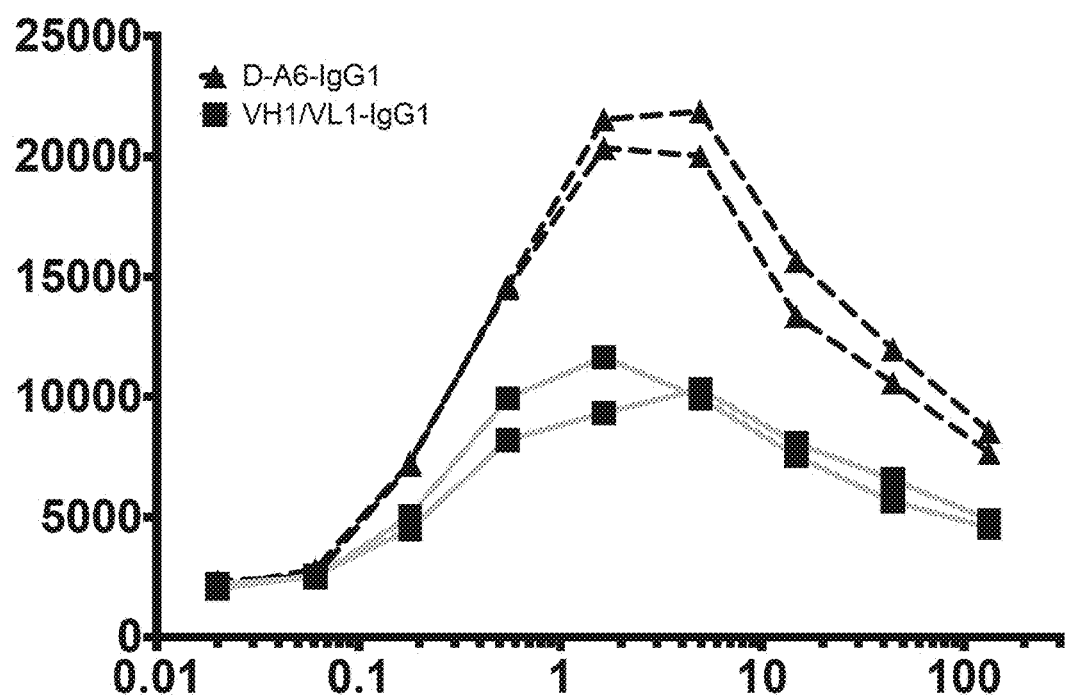
FIG. 11. Relative potency of double-purified, monomeric versions of the D-A6 and VH1/VL1 IgG1 antibodies in GITR Jurkat cell reporter assay. ProA-SEC purified D-A6 and VH1/VL1 antibodies in human IgG1 format were applied in the Promega GITR+ Jurkat cell reporter assay. This assay showed that clone D-A6 was significantly more potent than VH1/VL1 in induction of GITR signalling. X-axis shows concentration of mAb in nM, and Y-axis shows RLU.

Based on the flow cytometric, epitope competition and receptor agonism data, the IgG D-A6 was prioritized for further in vitro analyses. Active aggregates of IgGs such as dimers are commonly produced during IgG1 expression and purification procedures. These aggregates can create false-positive or exaggerated signals in receptor agonism assays. To ensure that accurate comparison was made between the D-A6 and VH1/VL1 IgGs, they were each purified twice: firstly, by protein A column binding and secondly by Size Exclusion Chromatography to remove any protein species larger than the expected molecular with of a human IgG1 (approximately 150 kDa). The fully purified IgG1 proteins were then tested for concentration-dependent agonist activation of GITR in the cell-based reporter assay. This assay demonstrated that, unexpectedly, the D-A6 IgG1 exhibits significantly stronger concentration-dependent receptor activation then the VH1/VL1 IgG (FIG. 11). In this assay, using duplicate analyses of both antibodies, the D-A6 clone exhibited: 1. Higher total potency with a maximum RLU value of 21876 for D-A6, versus 11664 for VH1/VL1; 2. Higher signal at all concentrations of D-A6 IgG1 tested from 0.1 to 133 nM, in comparison to VH1/VL1.

Flow Cytometric Analyses of Lead IgG Binding Specificity at the Cell Membrane

Figure 10A:
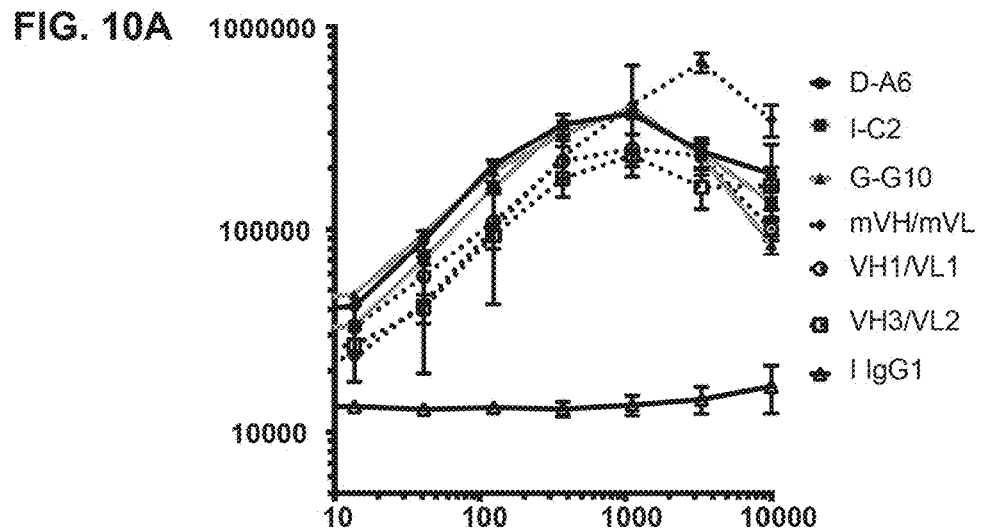
FIG. 10A-10C. Flow cytometric testing of leads and control IgGs in binding to human and cyno GITR+ stably-transfected murine cells. Lead library-derived and control IgGs ("I IgG1" represents Isotype IgG1) were examined for specific binding on (FIG. 10A) human and (FIG. 10B) cyno-transfected murine cells. Concentration-dependent binding was observed against both cell lines. As in the GITR agonism assay on human GITR-transfected human Jurkat cells, maximum binding signal in this experiment was observed at approximately 1000 ng/ml for all humanized and grafted clones. No binding signals above background were observed against murine cells transfected with an unrelated human receptor (FIG. 10C). In each graph, X-axis shows concentration of IgG1 in ng/ml, and Y-axis shows mean fluorescence intensity (MFI).
Figure 10B:
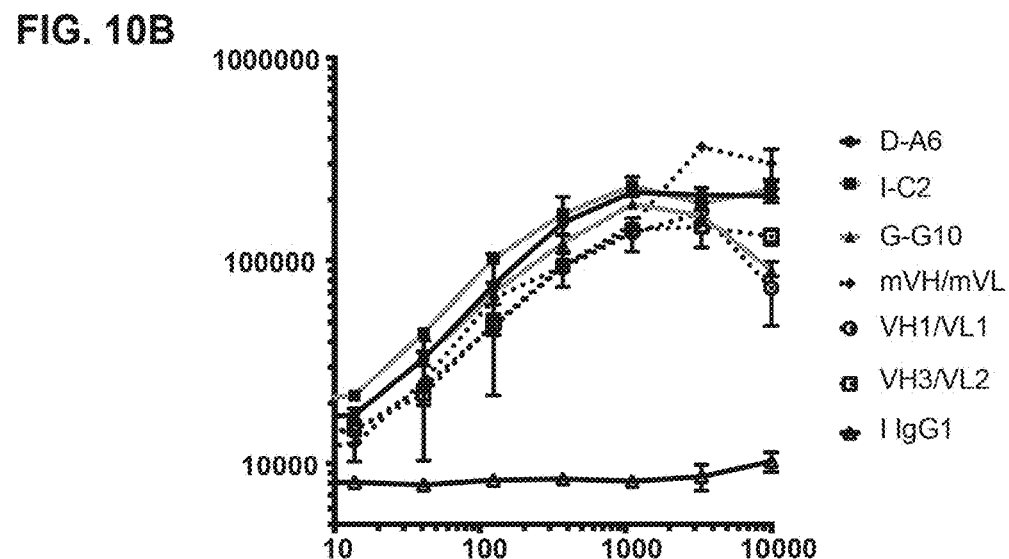
Figure 10C:
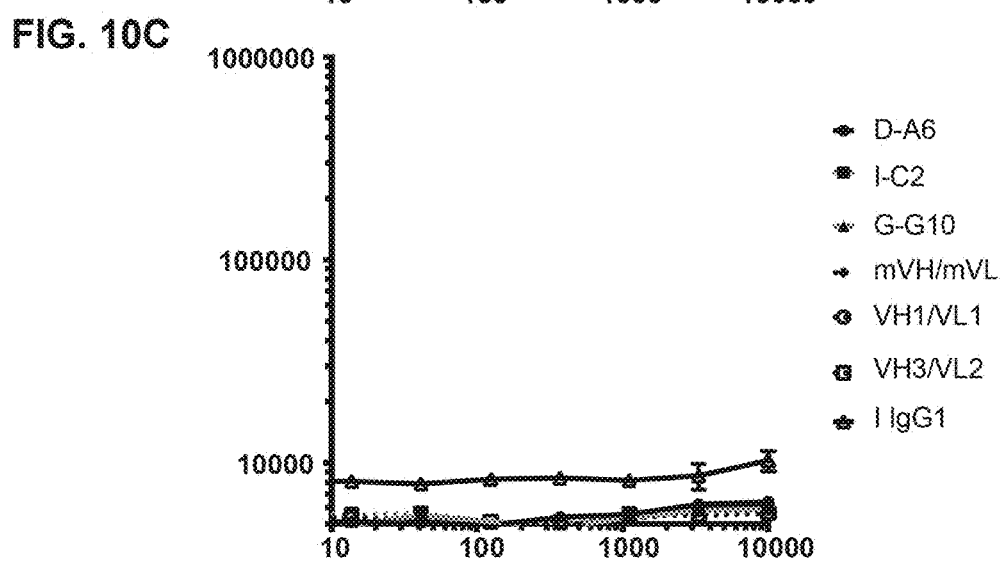

Concentration-dependent binding to GITR at the cell surface was analysed using flow cytometry. As none of the IgGs were observed to bind to mouse GITR-Fc, proprietary murine blastoma and CHO-K1 cells were stably transfected with either human or cyno GITR full-length cDNAs. IgGs mVH/mVL, VH1/VL1, VH3/VL2, D-A6, G-G10, I-C2 and an isotype control IgG1 were then tested over a concentration range of 10,000-13.7 ng/ml for binding to human, cyno or negative control (stably transfected with an unrelated human receptor) murine blastoma cells (FIG. 10). All IgGs other than the isotype control showed concentration-dependent binding to human and cyno GITR+ cells, with a maximum MFI in each case being at approximately 1111 ng/ml. No measurable binding was observed for any IgG, at any concentration, to the negative control cell line.

Figure 12A:
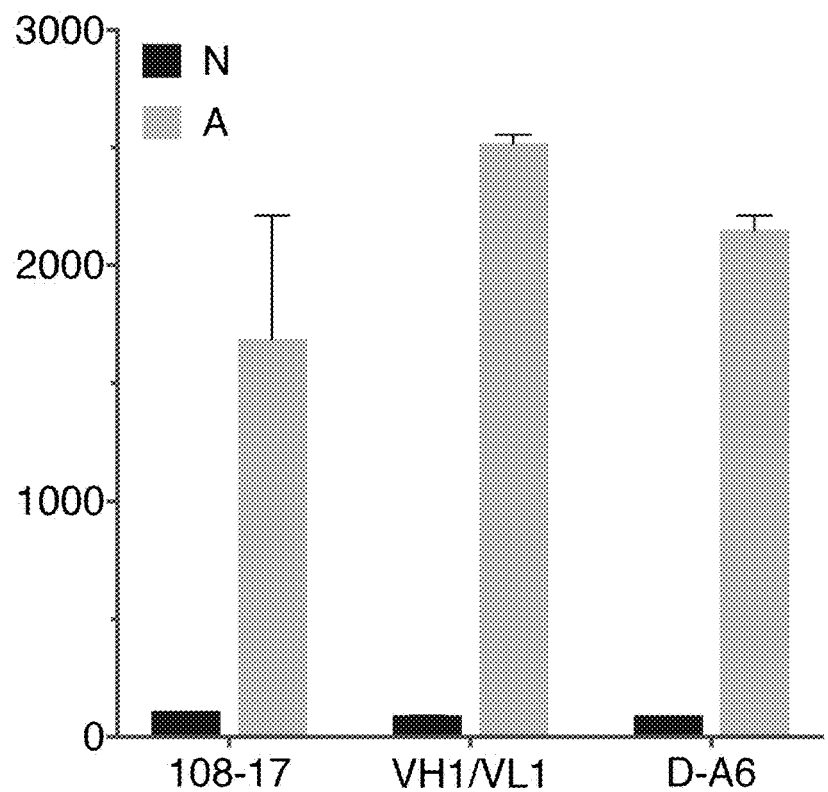
FIG. 12A-12B. Specificity of membrane binding in flow cytometry of GITR expressing cells.
Figure 12B:
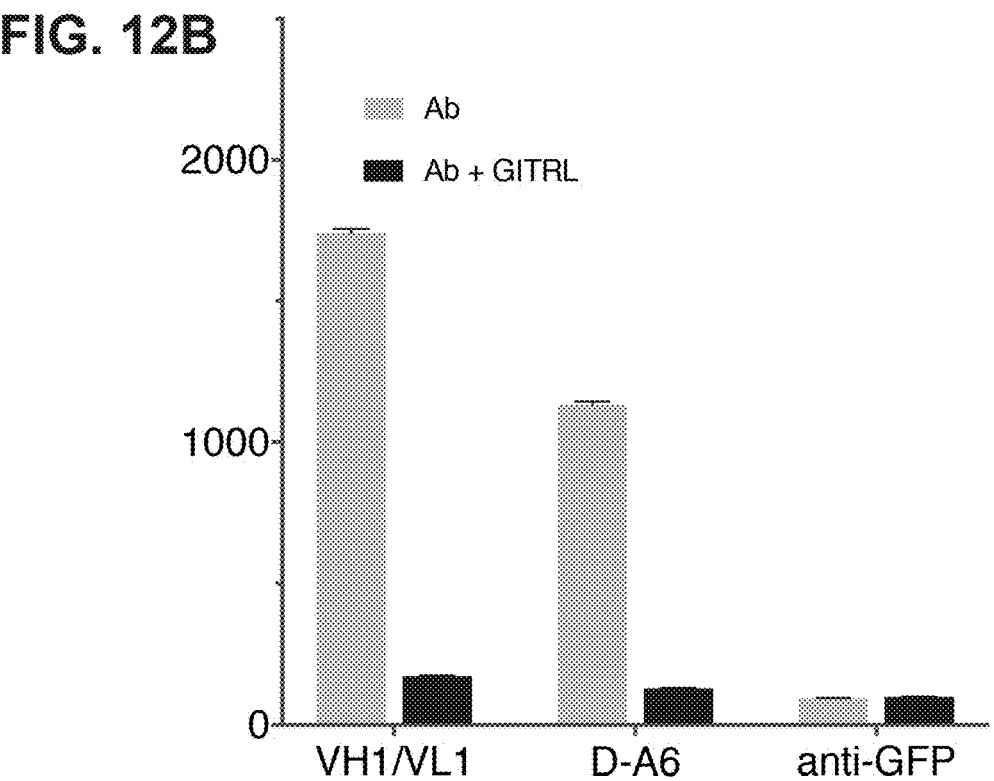

To examine the binding of the lead IgGs to GITR+ human cells, HuT78 cells were activated by incubation with anti-CD3/anti-CD28 beads for 3 days. Activation of t-cells is associated with the upregulation of GITR expression. Naïve cells were incubated in media alone. IgGs VH1/VL1, D-A6 and an anti-GITR commercial control antibody '108-17' were then tested at 10 μg/ml for binding to activated and naïve cells. All 3 antibodies showed strong binding to the activated cells, but no discernible binding to naïve cells (FIG. 12A). Similarly activated HuT78 cells were then stained with IgG1s VH1/VL1, D-A6 and a negative control, human IgG1 kappa anti-GFP commercial antibody 'AbD18705_hIgG1' at 1.1 μg/ml. In each case staining was performed in the presence or absence of 10 μg/ml human GITR ligand protein. The anti-GFP control showed no binding to the activated cells in either analysis, whereas IgGs VH1/VL1 and D-A6 both showed binding in the absence of excess GITRL protein (FIG. 12B). This assay showed that clone D-A6 specifically binds GITR on activated human T-cells and that its binding site overlaps with that of GITRL, the natural binding partner for GITR.

In Vitro Analysis of Concentration-Dependent FcγRIIIa Engagement by IgG1 and IgG1-N297A Antibodies The humanized form of monoclonal 6C8, also known as TRX-518, is a non-glycosylated human IgG1. The removal of the canonical n-linked glycosylation is achieved by adding the mutation N297A to the human IgG1 Fc CH2 region. This aglycosylated Fc region is rendered null for binding to all human Fcγ receptors, including the critically important FcγRIIIa receptor, which is associated with driving ADCC by NK cells against antibody-bound cells. It is possible that the presence of ADCC activity in an anti-GITR agonist antibody may be highly beneficial, as it may allow the depletion of immunosuppressive tumour-infiltrating Treg cells, which are known to express high levels of GITR.

Figure 13A:
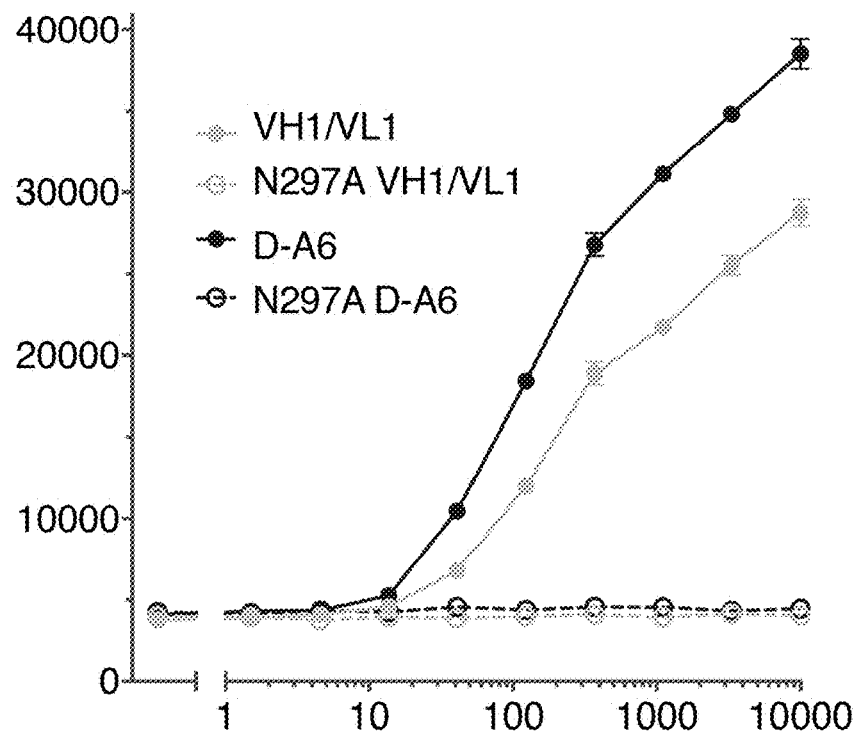
FIG. 13A-13B. Relative potency of the D-A6 VH1/VL1 IgG1, D-A6 IgG1-N297A and VH1/VL1 IgG1-N297A (aglycosylated) antibodies in induction of FcγRIIIa signalling in a Jurkat cell reporter assay using CHO-K1 human cells (FIG. 13A) and cyno GITR+ cells (FIG. 13B). In each graph, x-axis shows antibody concentration in ng/ml and y-axis shows RLU. This assay showed that the D-A6 and VH1/VL1 antibodies in IgG1 form is capable of inducing FcγRIIIa signalling (representative of induction of ADCC activity in NK cells), while neither D-A6 IgG1-N297A nor VH1/VL1 IgG1-N297A antibodies induced signalling. Importantly, D-A6 IgG1 was significantly more potent in inducing signalling than the VH1/VL1 IgG1.
Figure 13B:
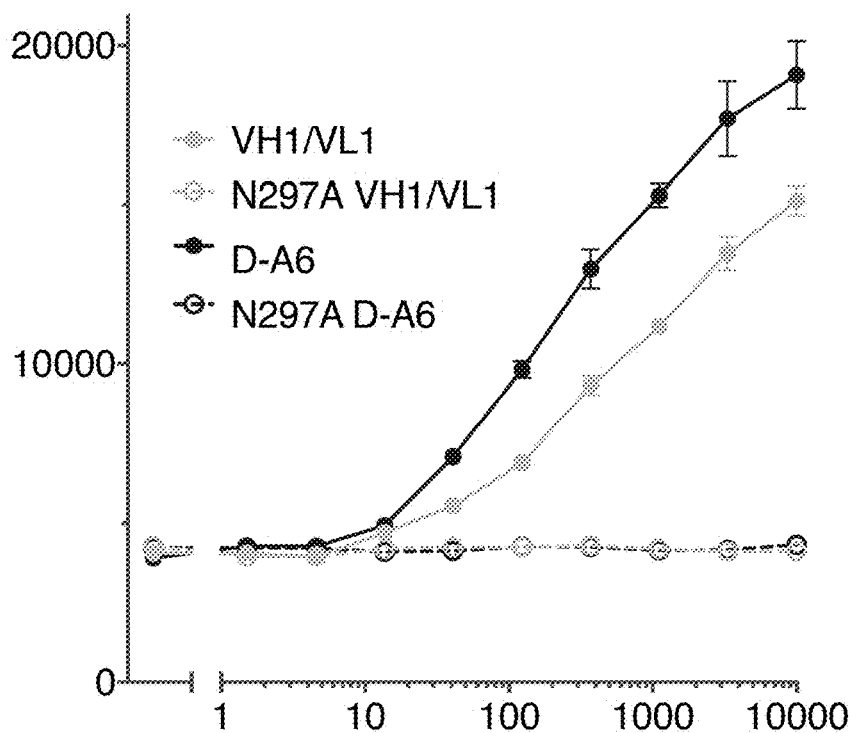

To examine the ability of the VH1/VL1 (in which the v-domains are identical in amino acid sequence to TRX-518) and D-A6 v-domains to drive ADCC, both antibodies were expressed in human IgG1 and IgG1-N297A formats. These antibodies were proA-SEC purified as above and then used in the Promega ADCC assay, with CHO-K1 target cells stably expressing either human or cyno GITR as the target cell population. On both human (FIG. 13A) and cyno (FIG. 13B) CHO-K1 cells, both VH1/VL1 and D-A6 IgG1 antibodies showed dose-dependent FcγRIIIa activation, whereas neither IgG1-N297A antibody induced signalling at any concentration used. Importantly, the D-A6 IgG1 was significantly more potent (>2-fold) than the VH1/VL1 IgG1 (FIG. 13A, 13B). On human GITR cells, observed EC50 values were 15.4 nM for D-A6 IgG1 vs 35.6 nM for VH1/VL1 IgG1. On cyno GITR cells, observed EC50 values were 57.9 nM for D-A6 IgG1 vs 160.0 nM for VH1/VL1 IgG1.

Lead IgG D-A6 Analysis in 'Developability' ELISA Assays

Figure 14A:
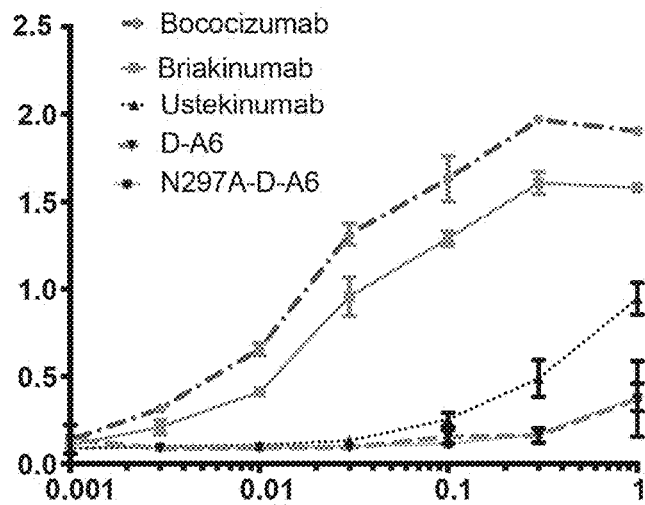
FIG. 14A-14C. Development risk ELISAs. This assay showed that the D-A6 antibody in IgG1 and IgG1-N297A forms is negative for binding to the negatively charged biomolecules Insulin (FIG. 14A), double-stranded DNA (dsDNA) (FIG. 14B) and single-stranded DNA (ssDNA) (FIG. 14C). In each graph, X-axis shows IgG concentration in µg/ml and Y-axis shows binding signal (OD 450 nm). Strong off-target binding to these molecules has been shown to be a high-risk indicator of poor clinical performance of therapeutic antibodies.
Figure 14B:
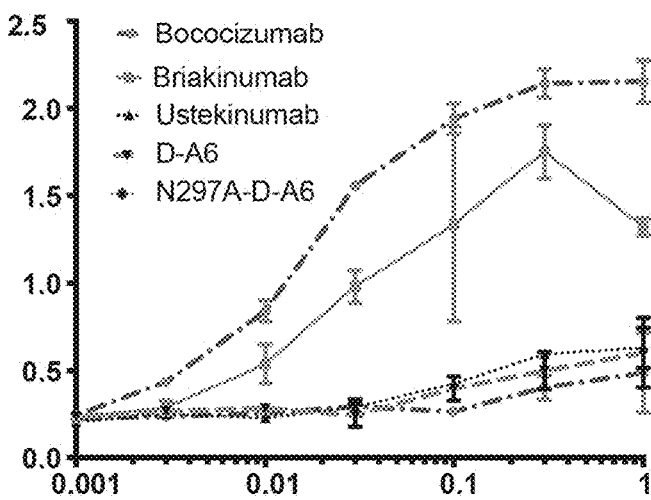
Figure 14C:
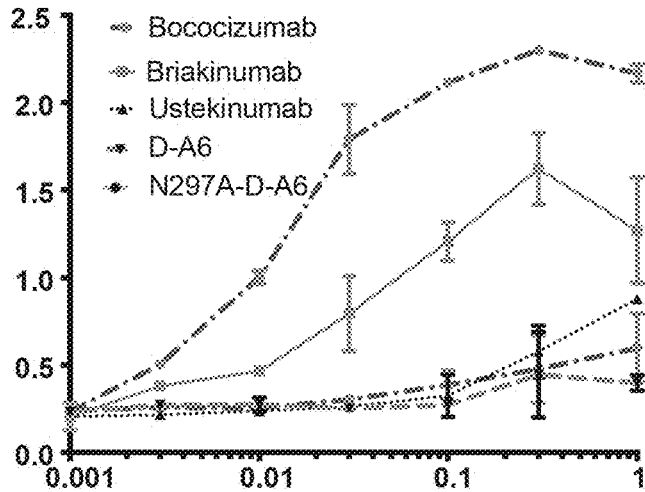

It is known in the art that the binding of IgGs intended for therapeutic use to several indicative biological substrates is an indicator of high risk for poor performance in patients due to poor bioavailability and short in vivo half-life. Three such biological substrates are Insulin, dsDNA and ssDNA. These three substrates were therefore used to coat ELISA plates an examine the binding of the IgG1 and IgG1-N297A versions of the optimised lead D-A6. Binding signals for these human IgG-based antibodies was compared to "positive control" human IgG antibodies that have been found to have polyreactivity and poor performance stopped their progress in clinical trials (Bococizumab and Briakinumab human IgG1 analogues). For a negative control human IgG1 antibody, an IgG1 Ustekinumab analogue was used as it reacts with the same therapeutic target as Briakinumab, but has longer pK and was successfully approved as a therapeutic product. In the ELISA analyses shown in FIG. 14, the positive control antibodies exhibited the expected strong reactivity to all 3 substrates, while the negative control showed low reactivity. Importantly, both the D-A6 IgG1 and IgG1-N297A proteins showed binding the negative control against all 3 substrates. This finding underlined the maintenance of highly specific target-driven binding in optimised clone D-A6.

In Silico Immunogenicity Analyses of Lead v-Domains

Recent US FDA guidance has recommended in silico immunogenicity assessment of t-cell epitope risk for all antibodies intended for therapeutic development (see USFDA [2014] Guidance for Industry—Immunogenicity Assessment for Therapeutic Protein Products). To examine the anti-GITR antibodies for human t-cell epitope content, the v-domain sequences for IgGs mVH/mVL, VH3/VL2, D-A6, G-G10 and I-C2 were submitted to the Lonza Epibase IS™ system (Version 3) for DRB1 score based on global human population statistics (Table 5). In this analysis, human t-cell immunogenicity risk is given a total score across both v-domains. The starting murine clone mVH/mVL received a score of 1680.4, which is in the lower end of predicted immunogenicity range for chimeric antibodies currently approved for use as therapeutics (1500 to >2400). Grafted clone VH3/VL2 (direct germline graft with no back mutations in the frameworks) exhibited a reduced score of 994.0, in the lower end of predicted immunogenicity range for humanized antibodies currently approved for use as therapeutics (1000 to 1600). Lead clones D-A6 and G-G10 received scores of 932.5 and 842.8, respectively. These scores placed in the predicted immunogenicity range for fully human antibodies currently approved for use as therapeutics (250 to 1200).

Comparison of the sequences of clones D-A6 (full function retained) and MH (cyno GITR binding and human GITR agonism ablated) showed only 5 amino acid differences. To examine the influence of these mutations on immunogenicity and function, five further designer mutants (A6.1 to A6.5, see Table 4 for CDR sequences) were also submitted for Epibase analysis (Table 5). This assessment showed that the total DRB1 score for these mutants could further reduce the predicted immunogenicity of D-A6 down to a low of 845.9 in clone A6.4. However, when ELISA binding analyses were performed on the IgG1 proteins for A6.1 to A6.5, all clones retained binding to human GITR, but only A6.1 retained binding to cyno GITR comparable to VH1/VL1 and D-A6. Cyno GITR binding was greatly diminished for all of clones A6.2 to A6.5.

SPR Affinity Analyses for Anti-GITR Fab Fragments Vs hGITR-Fc and cGITR-Fc

As GITR agonism and ADCC analyses had all shown lead clone D-A6 to be significantly improved over VH1/VL1, we analysed the affinity values for these two antibodies on Biacore. Monomeric Fab fragments were generated and flowed in the mobile phase on human and cyno GITR-Fc coated biosensor chips, to derive 1:1 binding values. This data showed that the $K_D$ values for VH1/VL1 and D-A6 Fabs were near identical on human GITR but, in agreement with the ELISA data, D-A6 Fab showed approximately 4-fold improved affinity for cyno GITR (Table 6). Chi2 values for all analyses were <0.15, indicating that the data accurately fits to 1:1 Langmuir kinetics models.

In Vitro Analysis of Potency of GITR Agonism for Further Lead IgG1s Versus VH1/VL1 IgG1

Figure 15D:
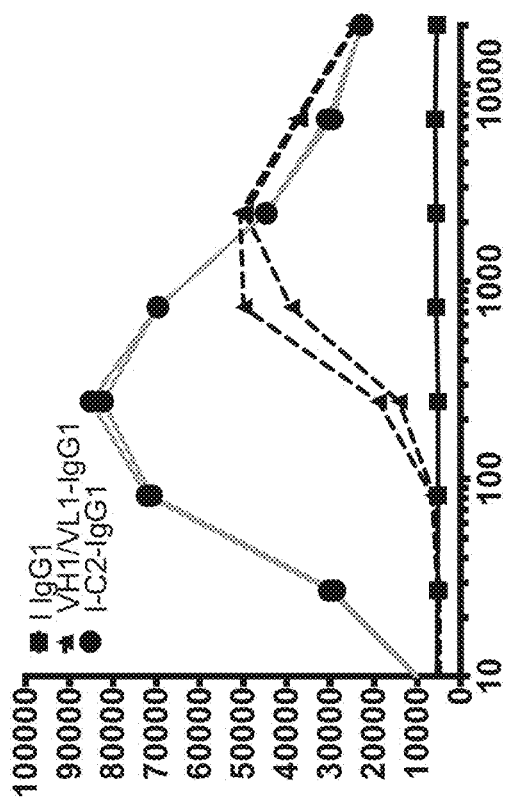
Figure 15C:
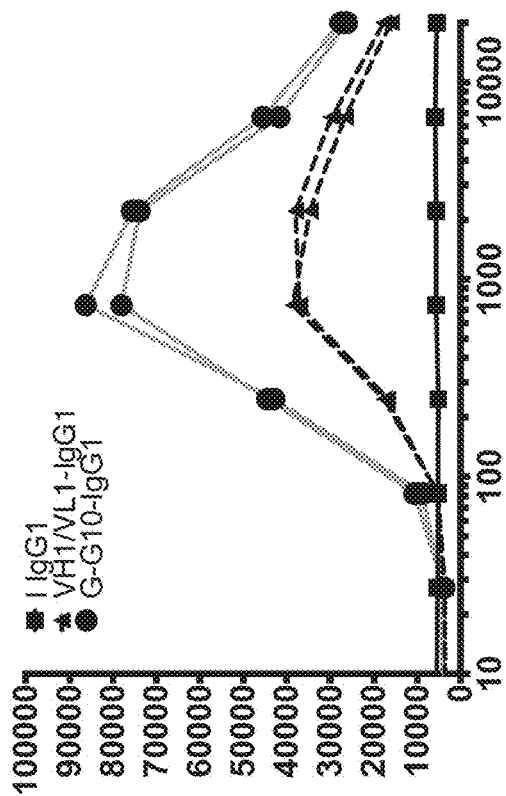

As the IgG D-A6 had exhibited improved potency in receptor agonism in IgG1 format, a series of further leads were prioritized for additional GITR agonism analyses. This assay demonstrated that the D-A6 clone in both IgG1null and IgG1-N297A formats (FIG. 15A), the D-A6.1 clone (FIG. 15B) and the library-derived leads G-G10 (FIG. 15C) and I-C2 (FIG. 15D), in IgG1 format, all also exhibit significantly stronger concentration-dependent receptor activation than the VH1/VL1 IgG. In this assay, using duplicate analyses of all antibodies, the IgG clones exhibited: 1. Higher total potency in their maximum RLU values; 2. Higher signal at all concentrations of IgG tested in comparison to VH1/VL1, with the exception of I-C2. Isotype human IgG1 was also included (FIG. 15C, 15D), which showed no ability to agonise the receptor.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

In each of Tables 1-4 below, SEQ ID NOs are shown in parenthesis below each sequence.

TABLE 1

Amino acid sequences murine anti-GITR CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GFSLSTSGMGVG (4) | LAHIWWDDDKYYNPSLKS (5) | TRRYFPFAY (6) | KASQNVGTNVA (13) | SASYRYS (14) | QQYNTDPLT (15) |
| Kabat | TSGMGVG (66) | HIWWDDDKYYNPSLKS (67) | TRRYFPFAY (6) | KASQNVGTNVA (13) | SASYRYS (14) | QQYNTDPLT (15) |
| Chotia | GFSLSTSGM (68) | WWDDDK (69) | ARTRRYFPFAY (70) | KASQNVGTNVA (13) | SASYRYS (14) | QQYNTDPLT (15) |
| IMGT | GFSLSTSGMG (71) | IWWDDDK (72) | ARTRRYFPFAY (70) | QNVGTN (73) | SAS | QQYNTDPLT (15) |
| AHo | FSLSTSGMG (74) | IWWDDDKYYNPSLKS (75) | TRRYFPFA (76) | ASQNVGTN (77) | SASYRYS (14) | YNTDPL (78) |
| Abm | GFSLSTSGMGVG (4) | HIWWDDDKYY (79) | TRRYFPFAY (6) | KASQNVGTNVA (13) | SASYRYS (14) | QQYNTDPLT (15) |
| Contact | STSGMGVG (80) | LAHIWWDDDKYY (81) | ARTRRYFPFA (82) | GTNVAWY (83) | LLIYSASYRY (84) | QQYNTDPL (85) |

TABLE 2

Amino acid sequence of 6C8 murine anti-GITR v-domains (GITR-mVH/mVL) and human germline CDR grafts (GITR-VH1-4/VL1-3).
(1) Human germline definitions used for grafting based on IMGT system. (2) Sequence dashes in this CDR are added to show the spacing of sampled residues, based on sequence alignment. (3) CDR residues are in bold and underlined. As noted above, some CDR definitions used in this manuscript are an expanded definition in comparison to the classical Kabat definition.

| V DOMAIN | Human germ- line (1) | Amino acid sequence (3) |
|---|---|---|
| GITR-mVH | n/a | QVTLKESGPGILKPSQTLSLTCSFSGFSLSTSGMGVGWIRQPSGKGLEWLAHIWWDDDKYYNPSLKSQLTISKDTSRNQVFLKITSVDTADAATYYCARTRRYFPFAYWGQGTLVTVSS (SEQ ID NO: 86) |
| GITR-VH1 | IGHV2-70 | QVTLRESGPALVKPTQTLTLTCTFSGFSLSTSGMGVGWIRQPPGKALEWLAHIWWDDDKYYNPSLKSRLTISKDTSKNQVVLTMTNMDPVDTATYYCARTRRYFPFAYWGQGTLVTVSS (SEQ ID NO: 87) |
| GITR-VH2 | IGHV3-7- XH (2) | EVQLVESGGGLVQPGGSLRLSCAASGFTFS-SYMMSWVRQAPGKGLEWLAHIWWDDDKYYVDSVKGRFTISRDNAKNSLYLQMNSLRAEDTAVYYCARTRRYFPFAYWGQGTLVTVSS (SEQ ID NO: 88) |
| GITR-VH3 | IGHV3-7 | EVQLVESGGGLVQPGGSLRLSCAASGFSLSTSGMGVGWVRQAPGKGLEWLAHIWWDDDKYYVDSVKGRFTISRDNAKNSLYLQMNSLRAEDTAVYYCARTRRYFPFAYWGQGTLVTVSS (SEQ ID NO: 89) |
| GITR-VH4 | IGHV5-51 | EVQLVQSGAEVKKPGESLKISCKGSGFSLSTSGMGVGWVRQMPGKGLEWLAHIWWDDDKYYSPSFQGQVTISADKSISTAYLQWSSLKASDTAMYYCARTRRYFPFAYWGQGTLVTVSS (SEQ ID NO: 90) |
| GITR-mVL | n/a | DIVMTQSQKFMSTSVGDRVSVTCKASQNVGTNVAWYQQKPGQSPKALIYSASYRYSGVPDRFTGSGSGTDFTLTINNVHSEDLAEYFCQQYNTDPLTFGAGTKLEIK (SEQ ID NO: 91) |
| GITR-VL1 | IGKV3-15 | EIVMTQSPATLSVSPGERATLSCKASQNVGTNVAWYQQKPGQAPRLLIYSASYRYSGIPARFSGSGSGTEFTLTISSLQSEDFAVYYCQQYNTDPLTFGGGTKVEIK (SEQ ID NO: 92) |
| GITR-VL2 | IGKV3-11 | EIVLTQSPATLSLSPGERATLSCRASQNVGTNVAWYQQKPGQAPRLLIYSASYRYSGIPARFSGSGSGTDFTLTISSLEPEDFAVYYCQQYNTDPLTFGGGTKVEIK (SEQ ID NO: 93) |
| GITR-VL3 | IGKV1-39 | DIQMTQSPSSLSASVGDRVTITCRASQNVGTNVAWYQQKPGKAPKLLIYSASYRYSGVPSRFSGSGSGTDFTLTISSLQPEDFATYYCQQYNTDPLTFGGGTKVEIK (SEQ ID NO: 94) |

TABLE 3

Amino acid sequences of CDRs of 74 unique anti-GITR v-domains and % sequence identity to human germline (% ID) in the CDRs.

| Clone name | HCDR3 | HCDR1 | HCDR2 | LCDR3 | LCDR1 | LCDR2 | % ID |
|---|---|---|---|---|---|---|---|
| D_A6 | TRQYFPFAY (31) | GFSLSTSGYGVG (29) | LAHIWWDDDKYYVDSVKG (26) | QQYSTDPLT (34) | RASQSVGSNLA (32) | SASYRYT (33) | 65% |
| G_G10 | TRQYFPFAY (31) | GFSLSTFGYGVG (35) | LAHIWWDDDKYYVDSVKG (26) | QQYSNDPLT (38) | RASQSVGTNLA (36) | YASYRYT (37) | 63% |
| I_C2 | TRLYFPFAY (39) | GFSLSTSGYGVG (29) | LAHIWWDDDKYYVDSVKG (26) | QQYSTDPLT (34) | RASQNVGSNLA (40) | SASNRYS (41) | 63% |
| C_A9 | TRMYFPFAY (95) | GFTFSTSSYGMS (96) | LANIWWDDEKYYVDSVKG (97) | QQYNNDPLT (98) | RASQSVGSYLA (99) | EASYRAS (100) | 75% |
| D_F8 | TRIYFPFAY (101) | GFSLSTSYGVS (60) | VANIWWDDEKYYVDSVKG (102) | QQYSNDPLT (38) | RASQSVGTYVA (103) | DASNRYT (104) | 74% |
| H_G1 | GRRYFPFAY (112) | GFSFSTSGYGMG (105) | LANIWWDDDKYYVDSVKG (106) | QQYSNWPLT (107) | RASQNVGSNLA (40) | SASYRAT (46) | 72% |
| H_B5 | ARRYFPFAY (108) | GFSFSTSGYGMG (105) | LANIWWDDDKYYVDSVKG (106) | QQYNTWPLT (109) | RASQSVGSYLA (99) | SASYRAT (46) | 72% |
| D_B1 | TRIYFPFAY (101) | GFSLSTSSMGMS (110) | LANIWWDDEKYYVDSVKG (97) | QQYSTDPLT (34) | RASQNVGSYVA (111) | SASNRYT (44) | 71% |
| K_D10 | GRRYFPFAY (112) | GFTFSTSGYGMG (113) | VANIWWDDEKYYVDSVKG (102) | QQYSTWPLT (114) | RASQSVGTNLA (36) | SASYRAS (53) | 71% |
| E_D5 | ARRYFPFAY (108) | GFTLSTSGYGVG (115) | LANIWWDSDKYYVDSVKG (116) | QQYSNWPLT (107) | RASQNVGTYLA (117) | SASNRAT (118) | 71% |
| H_B2 | TRQYFPFAY (31) | GFSLSTSGMGMG (58) | LANIWWDDEKYYVDSVKG (97) | QQYNTWPLT (109) | RASQDVGTYLA (119) | SASNRAT (118) | 69% |
| H_D11 | ARRYFPFAY (108) | GFTLSASGYGMG (120) | VANIWWDDDKYYVDSVKG (121) | QQYSTWPLT (114) | RASQNVGSYLA (122) | SASYRAS (53) | 69% |
| G_G3 | TRMYFPFAY (95) | GFSLSTSSYGVS (60) | LANIWWDDEKYYVDSVKG (97) | QQYNNDPLT (98) | RASQNVGTYVA (123) | DASNRYS (124) | 69% |
| J_C5 | TRLYFPFAY (39) | GFSLSTSSYGVS (60) | VAHIWWDDEKYYVDSVKG (55) | QQYSNDPLT (38) | RASQSVGTNLA (36) | SASYRYT (33) | 69% |
| G_E9 | TDRYFPFAY (125) | GFTFSTSGWAWG (126) | LAHIWWDDDKYYVDSVKG (26) | QQRNNDPLT (127) | RASQSVGTYVA (103) | DASNRAT (128) | 69% |
| E_C6 | NRRYFPFAY (45) | GFTLSTSGYGMS (129) | LAHIWWDDDKYYVDSVKG (26) | QQYSNDPLT (38) | RASQSVGSNVA (57) | SASYRAT (46) | 69% |
| A_F2 | GRRYFPFAY (112) | GFSLSTSGYGMG (64) | LANIWWDSDKYYVDSVKG (116) | QQYSTWPLT (114) | RASQNVGSNLA (40) | SASNRAS (130) | 69% |
| E_E2 | ARRYFPFAY (108) | GFSLSTSGYGMG (64) | LANIWWDDDKYYVDSVKG (106) | QQYSTWPLT (114) | RASQSVGTNLA (36) | SASNRAS (130) | 69% |
| E_C12 | IRRYFPFAY (131) | GFTLSTSGYGMS (129) | LAHIWWDSDKYYVDSVKG (132) | QQYSNDPLT (38) | RASQSVGSNLA (32) | SASNRAS (130) | 69% |
| F_B11 | NRRYFPFAY (45) | GFSLSTSGMGVS (54) | VAHIWWDDEKYYVDSVKG (55) | QQYSTDPLT (34) | RASQSVGSNLA (32) | SASYRAT (46) | 68% |
| C_B10 | NRRYFPFAY (45) | GFSLSTSGMGMS (61) | LAHIWWDDDKYYVDSVKG (26) | QQYSNDPLT (38) | RASQNVGSNLA (40) | SASYRAT (46) | 68% |
| G_A6 | TRMYFPFAY (95) | GFSLSTFSYGVS (133) | LAHIWWDSDKYYVDSVKG (132) | QQYSNDPLT (38) | RASQNVGTYLA (117) | DASYRYT (134) | 68% |
| C_B12 | NRRYFPFAY (45) | GFTFSTSGMGVS (135) | VAHIWWDDEKYYVDSVKG (55) | QQYSTDPLT (34) | RASQSVGSNVA (57) | SASNRYT (44) | 68% |
| E_A1 | NRRYFPFAY (45) | GFTLSTSGMGMS (136) | LAHIWWDDDKYYVDSVKG (26) | QQYSNDPLT (38) | RASQSVGSNLA (32) | SASYRAS (53) | 68% |
| F_F2 | NRRYFPFAY (45) | GFSLSTSGMGMS (61) | VAHIWWDDEKYYVDSVKG (55) | QHYSTDPLT (137) | RASQSVGSNLA (32) | SASNRAS (130) | 68% |

TABLE 3-continued

Amino acid sequences of CDRs of 74 unique anti-GITR v-domains and % sequence identity to human germline (% ID) in the CDRs.

| Clone name | HCDR3 | HCDR1 | HCDR2 | LCDR3 | LCDR1 | LCDR2 | % ID |
|---|---|---|---|---|---|---|---|
| H_G4 | NRRYFPFAY (45) | GFTFSTSGMGMS (138) | VAHIWWDDEKYYVDSVKG (55) | QQYSTDPLT (34) | RASQNVGSNVA (139) | SASYRAT (46) | 68% |
| E_E4 | NRRYFPFAY (45) | GFSLSTSGMGMS (61) | LSHIWWDDEKYYVDSVKG (140) | QQYSTDPLT (34) | RASQSVGSNLA (32) | SASNRAS (130) | 68% |
| F_B9 | NRRYFPFAY (45) | GFSFSTSGMGVS (56) | VAHIWWDDEKYYVDSVKG (55) | QQYSTDPLT (34) | RASQSVGSNVA (57) | SASNRYT (44) | 68% |
| H_G5 | ARRYFPFAY (108) | GFSLSTSGYGMS (62) | LAHIWWDDEKYYVDSVKG (52) | QQYSTDPLT (34) | RASQNVGTNLA (43) | SASYRAT (46) | 68% |
| H_C8 | ARRYFPFAY (108) | GFSLSTSGYGMS (62) | VAHIWWDDDKYYVDSVKG (141) | QQYSTDPLT (34) | RASQNVGSNLA (40) | SASNRAS (130) | 68% |
| C_F2 | NRRYFPFAY (45) | GFSFSTSGYGVS (51) | LAHIWWDDEKYYVDSVKG (52) | QQYSTDPLT (34) | RASQNVGTNLA (43) | SASYRAS (53) | 66% |
| D_E3 | TTRYFPFAY (142) | GFSLSTSGYGVG (29) | LAHIWWDDEKYYVDSVKG (52) | QQYNNDPLT (98) | RASQNVGSYLA (122) | SASYRAS (53) | 66% |
| E_C4 | NRRYFPFAY (45) | GFSLSTSGMGMS (61) | VAHIWWDDDKYYVDSVKG (141) | QQYSNDPLT (38) | RASQNVGSNVA (139) | SASYRAT (46) | 66% |
| E_B10 | NRRYFPFAY (45) | GFSLSTSGYGVS (47) | LAHIWWDDEKYYVDSVKG (52) | QQYSTDPLT (34) | RASQSVGTNLA (36) | SASYRAS (53) | 66% |
| D_G11 | HRIYFPFAY (143) | GFSLSTSSMGMG (144) | VAHIWWDDEKYYVDSVKG (55) | QQYSTDPLT (34) | RASQSVGTYVA (103) | DASNRYS (124) | 66% |
| E_G11 | NRRYFPFAY (45) | GFSLSTSGMGVS (54) | LAHIWWDDEKYYVDSVKG (52) | QQYSNDPLT (38) | RASQNVGTNVA (145) | SASNRAT (118) | 66% |
| H_C5 | NRRYFPFAY (45) | GFSLSTSGMGMS (61) | VAHIWWDDEKYYVDSVKG (55) | QQYSTDPLT (34) | RASQSVGTNVA (49) | NASNRAS (146) | 66% |
| K_D6 | NRRYFPFAY (45) | GFSLSTSGMGMS (61) | LAHIWWDDDKYYVDSVKG (26) | QQYSNDPLT (38) | RASQSVGSNVA (57) | SASYRAS (53) | 66% |
| E_F10 | GRRYFPFAY (112) | GFSLSTSGYGVG (29) | VANIWWDDDKYYVDSVKG (121) | QQYNTWPLT (109) | RASQNVGSYLA (122) | SAYYRAT (147) | 66% |
| E_G3 | ARRYFPFAY (108) | GFSLSTSGYGVG (29) | LANIWWDDDKYYVDSVKG (106) | QQYSTWPLT (114) | RASQNVGTYLA (117) | SASYRAS (53) | 66% |
| C_D5 | NRRYFPFAY (45) | GFSLSTSGYGVS (47) | LAHVWWDDEKYYVDSVKG (48) | QQYNNWPLT (50) | RASQSVGTNVA (49) | SASYRAT (46) | 65% |
| F_H9 | TTRYFPFAY (142) | GFSLSTSGMGMG (58) | VAHIWWDDDKYYVDSVKG (141) | QQYSTLPLT (148) | RASQNVGSNLA (40) | SASYRAT (46) | 65% |
| E_D9 | NRRYFPFAY (45) | GFSLSTSGYGMS (62) | LAHIWWDDDKYYVDSVKG (26) | QQYSTDPLT (34) | RASQNVGTNLA (43) | SASYRAS (53) | 65% |
| D_A9 | SRLYFPFAY (149) | GFTLSTSGMGVS (150) | VAHIWWDDEKYYVDSVKG (55) | QQHNDPLT (151) | RASQNVGTYVA (123) | FASNRAT (152) | 65% |
| C_C11 | NRRYFPFAY (45) | GFTFSTSGMGVS (135) | LAHIWWDDDKYYVDSVKG (26) | QQYSTDPLT (34) | RASQNVGSNVA (139) | DASNRYS (124) | 65% |
| E_F4 | NRRYFPFAY (45) | GFTLSTSGYGVS (153) | VAHIWWDDDKYYVDSVKG (141) | QQYSTDPLT (34) | RASQNVGSNLA (40) | SASYRAS (53) | 65% |
| F_F1 | NRRYFPFAY (45) | GFTFSTSGMGVS (135) | LAHIWWDDDKYYVDSVKG (26) | QQYNNDPLT (98) | RASQNVGSNLA (40) | SASNRYS (41) | 65% |
| C_C10 | ARRYFPFAY (108) | GFSLSTSGMGVS (54) | LAHIWWDDEKYYVDSVKG (52) | QQYSTDPLT (34) | RASQNVGTNLA (43) | SASYRAT (46) | 65% |
| J_G8 | TRQYFPFAY (31) | GFSLSTSGMGVS (54) | VAHIWWDDDKYYVDSVKG (141) | QQYSNDPLT (38) | RASQSVGSNVA (57) | SASYRYT (33) | 65% |

TABLE 3-continued

Amino acid sequences of CDRs of 74 unique anti-GITR v-domains and % sequence identity to human germline (% ID) in the CDRs.

| Clone name | HCDR3 | HCDR1 | HCDR2 | LCDR3 | LCDR1 | LCDR2 | % ID |
|---|---|---|---|---|---|---|---|
| E_G12 | TRLYFPFAY (39) | GFSLSTSGMGMG (58) | LAHIWWDDDKYYVDSVKG (26) | QQYNNDPLT (98) | RASQNVGSYLA (122) | SASYRYT (33) | 65% |
| I_B7 | NRRYFPFAY (45) | GFSLSTSGYGVS (47) | VAHVWWDDEKYYVDSVKG (154) | QQYSNWPLT (107) | RASQSVGTNVA (49) | SASYRDT (155) | 65% |
| H_A7 | NRRYFPFAY (45) | GFSLSTSGYGMS (62) | LAHIWWDDDKYYVDSVKG (26) | QQYSNDPLT (38) | RASQNVGTNVA (145) | SASYRAS (53) | 65% |
| K_A12 | NRRYFPFAY (45) | GFSLSTSGMGMS (61) | LAHIWWDDEKYYVDSVKG (52) | QQYSTDPLT (34) | RASQSVGTNVA (49) | SASYRAS (53) | 65% |
| H_E11 | NRRYFPFAY (45) | GFSLSTSGFGMS (156) | LAHIWWDDEKYYVDSVKG (52) | QQYSTDPLT (34) | RASQSVGTNVA (49) | SASYRAS (53) | 65% |
| D_A4 | NRRYFPFAY (45) | GFSLSTSGMGMS (61) | LAHIWWDDEKYYVDSVKG (52) | QQYSTDPLT (34) | RASQNVGTNVA (145) | SASYRAS (53) | 63% |
| D_A11 | NRRYFPFAY (45) | GFTLSTSGMGMS (136) | VAHIWWDDEKYYVDSVKG (55) | QQYSTDPLT (34) | RASQNVGTNVA (145) | SASYRAS (53) | 63% |
| E_D10 | TVRYFPFAY (157) | GFSLSTSGYGVG (29) | LAHIWWDDDKYYVDSVKG (26) | QQYSTDPLT (34) | RASQSVGSNVA (57) | SASNRYS (41) | 63% |
| E_C8 | TRRYYPFAY (158) | GFSLSTSGYGVG (29) | VAHIWWDDDKYYVDSVKG (141) | QQYSTSPLT (159) | RASQSVGTYVA (103) | SASYRAS (53) | 63% |
| C_D10 | NRRYFPFAY (45) | GFSLSTSGMGMS (61) | LAHIWWDDDKYYVDSVKG (26) | QQYSTDPLT (34) | RASQNVGTNVA (145) | DASYRYT (134) | 63% |
| J_C6 | TRQYFPFAY (31) | GFSLSTSGYGVG (29) | VAHIWWDDDKYYVDSVKG (141) | QQYSTDPLT (34) | RASQSVGSNVA (57) | SASYRYT (33) | 63% |
| D_B7 | TRQYFPFAY (31) | GFSLSTSGYGMG (64) | LAHIWWDDDKYYVDSVKG (26) | QQYSNDPLT (38) | RASQNVGTNVA (145) | SASYRAS (53) | 63% |
| K_E12 | SRRYFPFAY (59) | GFTLSTSGMGMS (136) | VAHIWWDDDKYYVDSVKG (141) | QQYSTDPLT (34) | RASQNVGSNVA (139) | SASYRAS (53) | 63% |
| H_A3 | SRRYFPFAY (59) | GFSLSTSGMGMG (58) | LAHIWWDDDKYYVDSVKG (26) | QQYSTDPLT (34) | RASQNVGSNLA (40) | SASYRYT (33) | 63% |
| G_C11 | NRRYFPFAY (45) | GFSLSTSGYGVS (47) | VAHIWWDDDKYYVDSVKG (55) | QQYNNWPLT (50) | RASQSVGTNVA (49) | SASYRAS (53) | 63% |
| I_E12 | NRRYFPFAY (45) | GFSLSTSGFGVS (160) | LAHIWWDDEKYYVDSVKG (52) | QQYNNWPLT (50) | RASQSVGTNVA (49) | SASYRAT (46) | 63% |
| J_G10 | NRLYFPFAY (161) | GFSLSTSSLGMS (162) | VAHIWWDDDKYYVDSVKG (141) | QQYSTDPLT (34) | RASQNVGTNVA (145) | DASYRYT (134) | 63% |
| H_B3 | TRVYFPFAY (42) | GFSLSTSGYGVG (29) | LAHIWWDDDKYYVDSVKG (26) | QQYSTDPLT (34) | RASQNVGTNLA (43) | SASYRYT (33) | 62% |
| E_G7 | TRQYFPFAY (31) | GFTLSTSGMGVG (163) | VAHIWWDDEKYYVDSVKG (55) | QQYSTDPLT (34) | RASQNVSTNVA (164) | SASYRYT (33) | 62% |
| E_F6 | TRIYFPFAY (101) | GFSLSTSGYGVG (29) | LAHIWWDDEKYYVDSVKG (52) | QQYNNVPLT (165) | RASQNVGTNVA (145) | SASNRYS (41) | 62% |
| K_G9 | SRRYFPFAY (59) | GFSLSTSGMGVS (54) | VAHIWWEDEKYYVDSVKG (166) | QQYSTDPLT (34) | RASQNVGNNVA (167) | SASNRAS (130) | 62% |
| J_G6 | NRRYFPFAY (45) | GFSLSTSGYGVS (47) | VAHVWWDDEKYYVDSVKG (154) | QQYSTEPLT (168) | RASQSVGTNVA (49) | SASYRAS (53) | 62% |
| F_D2 | TRLYFPFAY (39) | GFTLSTSGMGVG (163) | LAHIWWDDDKYYVDSVKG (26) | QQYRTDPLT (169) | RASQNVGTNLA (43) | DASYRYT (134) | 60% |
| F_A8 | SRRYFPFAY (59) | GFSLSTSGMGMG (58) | LAHIWWDDDKYYVDSVKG (26) | QQYSTDPLT (34) | RASQNVGTNVA (145) | SASNRYS (41) | 60% |

TABLE 3-continued

Amino acid sequences of CDRs of 74 unique anti-GITR v-domains and % sequence identity to human germline (% ID) in the CDRs.

| Clone name | HCDR3 | HCDR1 | HCDR2 | LCDR3 | LCDR1 | LCDR2 | % ID |
|---|---|---|---|---|---|---|---|
| D_A10 | SRLYFPFAY (149) | GFTLSTSGMGVS (150) | VAHIWWDDEKYYVDSVKG (55) | QQHNKDPLT (170) | RTSQNVGTYVA (171) | LASNRVT (172) | 58% |

TABLE 4

Amino acid sequences of CDRs of 22 unique library-derived and designer anti-GITR IgGs.

| Clone name | HCDR3 | HCDR1 | HCDR2 | LCDR3 | LCDR1 | LCDR2 |
|---|---|---|---|---|---|---|
| C_B10 | NRRYFPFAY (45) | GFSLSTSGMGMS (61) | LAHIWWDDDKYYVDSVKG (26) | QQYSNDPLT (38) | RASQNVGSNLA (40) | SASYRAT (46) |
| C_D5 | NRRYFPFAY (45) | GFSLSTSGYGVS (47) | LAHVWWDDEKYYVDSVKG (48) | QQYNNWPLT (50) | RASQSVGTNVA (49) | SASYRAT (46) |
| C_F2 | NRRYFPFAY (45) | GFSFSTSGYGVS (51) | LAHIWWDDEKYYVDSVKG (52) | QQYSTDPLT (34) | RASQNVGTNLA (43) | SASYRAS (53) |
| D_A6 | TRQYFPFAY (31) | GFSLSTSGYGVG (29) | LAHIWWDDDKYYVDSVKG (26) | QQYSTDPLT (34) | RASQSVGSNLA (32) | SASYRYT (33) |
| F_B11 | NRRYFPFAY (45) | GFSLSTSGMGVS (54) | VAHIWWDDEKYYVDSVKG (55) | QQYSTDPLT (34) | RASQSVGSNLA (32) | SASYRAT (46) |
| F_B9 | NRRYFPFAY (45) | GFSFSTSGMGVS (56) | VAHIWWDDEKYYVDSVKG (55) | QQYSTDPLT (34) | RASQSVGSNVA (57) | SASNRYT (44) |
| G_G10 | TRQYFPFAY (31) | GFSLSTFGYGVG (35) | LAHIWWDDDKYYVDSVKG (26) | QQYSNDPLT (38) | RASQSVGTNLA (36) | YASYRYT (37) |
| H_A3 | SRRYFPFAY (59) | GFSLSTSGMGMG (58) | LAHIWWDDDKYYVDSVKG (26) | QQYSTDPLT (34) | RASQNVGSNLA (40) | SASYRYT (33) |
| I_C2 | TRLYFPFAY (39) | GFSLSTSGYGVG (29) | LAHIWWDDDKYYVDSVKG (26) | QQYSTDPLT (34) | RASQNVGSNLA (40) | SASNRYS (41) |
| J_C5 | TRLYFPFAY (39) | GFSLSTSSYGVS (60) | VAHIWWDDEKYYVDSVKG (55) | QQYSNDPLT (38) | RASQSVGTNLA (36) | SASYRYT (33) |
| K_A12 | NRRYFPFAY (45) | GFSLSTSGMGMS (61) | LAHIWWDDEKYYVDSVKG (52) | QQYSTDPLT (34) | RASQSVGTNVA (49) | SASYRAS (53) |
| MH | TRQYFPFAY (31) | GFSLSTSGYGMS (62) | VAHIWWDDEKYYVDSVKG (55) | QQYSTDPLT (34) | RASQSVGSNLA (32) | SASYRAT (46) |
| MH-1 | TRQYFPFAY (31) | GFSLSTSGMGMS (61) | VAHIWWDDEKYYVDSVKG (55) | QQYSTDPLT (34) | RASQSVGSNLA (32) | SASYRAT (46) |
| MH-2 | TRQYFPFAY (31) | GFSLSTSGYGVS (47) | VAHIWWDDEKYYVDSVKG (55) | QQYSTDPLT (34) | RASQSVGSNLA (32) | SASYRAT (46) |
| MH-3 | TRQYFPFAY (31) | GFSLSTSGYGMS (62) | VAHIWWDDEKYYVDSVKG (55) | QQYSTDPLT (34) | RASQNVGSNLA (40) | SASYRAT (46) |
| MH-4 | TRQYFPFAY (31) | GFSLSTSGYGMS (62) | VAHIWWDDEKYYVDSVKG (55) | QQYSTDPLT (34) | RASQSVGSNVA (57) | SASYRAT (46) |
| MH-5 | TRQYFPFAY (31) | GFSLSTSGYGMS (62) | VAHIWWDDEKYYVDSVKG (55) | QQYSTDPLT (34) | RASQSVGSNLA (32) | SASYRYT (33) |
| A6.1 | TRQYFPFAY (31) | GFSLSTSGYGVG (29) | LAHIWWDDDKYYVDSVKG (26) | QQYSTDPLT (34) | RASQSVGSNLA (32) | SASNRYT (44) |
| A6.2 | TRQYFPFAY (31) | GFSLSTSGYGVG (29) | LAHIWWDDDKYYVDSVKG (26) | QQYSTNPLT (63) | RASQSVGSNLA (32) | SASNRYT (44) |
| A6.3 | TRQYFPFAY (31) | GFSLSTSGYGVS (47) | LAHIWWDDDKYYVDSVKG (26) | QQYSTDPLT (34) | RASQSVGSNLA (32) | SASNRYT (44) |

TABLE 4-continued

Amino acid sequences of CDRs of 22 unique library-derived and designer anti-GITR IgGs.

| Clone name | HCDR3 | HCDR1 | HCDR2 | LCDR3 | LCDR1 | LCDR2 |
|---|---|---|---|---|---|---|
| A6.4 | TRQYFPFAY (31) | GFSLSTSGYGMS (62) | LAHIWWDDDKYYVDSVKG (26) | QQYSTDPLT (34) | RASQSVGSNLA (32) | SASNRYT (44) |
| A6.5 | TRQYFPFAY (31) | GFSLSTSGYGMG (64) | LAHIWWDDDKYYVDSVKG (26) | QQYSTDPLT (34) | RASQSVGSNLA (32) | SASNRYT (44) |

TABLE 5

Epibase DRB1 scores for lead anti-GITR IgG CDRs.

| Clone name | Total DRB1 | VL | VH |
|---|---|---|---|
| mVH/mVL | 1680.4 | 720.4 | 960 |
| G-VH3/VL2 | 994 | 426.3 | 567.7 |
| I-C2 | 1022.7 | 412.1 | 610.6 |
| G-G10 | 842.8 | 442.4 | 400.4 |
| D-A6 | 932.5 | 499.7 | 432.8 |
| A6.1 | 888.7 | 455.9 | 432.8 |
| A6.2 | 888.7 | 455.9 | 432.8 |
| A6.3 | 895.4 | 455.9 | 439.5 |
| A6.4 | 845.9 | 455.9 | 390 |
| A6.5 | 900.3 | 455.9 | 444.4 |

TABLE 6

SPR-derived affinity values for anti-GITR Fab vs hGITR and cGITR.

| Fab name (target) | $K_{on}$ $M^{-1} S^{-1}$ | $K_{off}$ $S^{-1}$ | $K_D$ M | chi$^2$ |
|---|---|---|---|---|
| VH1/VL1 (hGITR) | $4.5 \times 10^4$ | $5.1 \times 10^{-3}$ | $1.1 \times 10^{-7}$ | 0.0568 |
| VH1/VL1 (cGITR) | $2.2 \times 10^4$ | $6.1 \times 10^{-3}$ | $2.7 \times 10^{-7}$ | 0.0747 |
| D-A6 (hGITR) | $9.2 \times 10^4$ | $1.1 \times 10^{-2}$ | $1.2 \times 10^{-7}$ | 0.0574 |
| D-A6 (cGITR) | $3.7 \times 10^4$ | $2.1 \times 10^{-3}$ | $5.7 \times 10^{-8}$ | 0.140 |

The invention claimed is:

1. An antibody molecule that specifically binds to human glucocorticoid-induced TNF receptor (GITR) or an antigen-binding portion thereof, wherein the antibody molecule or antigen-binding portion comprises:
   (a) a heavy chain variable region comprising a HCDR1 of SEQ ID NO:29, a HCDR2 of SEQ ID NO:26, a HCDR3 of SEQ ID NO:31; and a light chain variable region comprising a LCDR1 of SEQ ID NO:32, a LCDR2 of SEQ ID NO:33, a LCDR3 of SEQ ID NO:34; or
   (b) a heavy chain variable region comprising a HCDR1 of SEQ ID NO:29, a HCDR2 of SEQ ID NO:26, a HCDR3 of SEQ ID NO:31; and a light chain variable region comprising a LCDR1 of SEQ ID NO:32, a LCDR2 of SEQ ID NO:44, a LCDR3 of SEQ ID NO:34.

2. The antibody molecule or antigen-binding portion of claim 1, wherein the heavy chain variable region, the light chain variable region, or both the heavy chain variable region and the light chain variable region comprise a human variable domain framework scaffold into which the CDRs have been inserted.

3. The antibody molecule or antigen-binding portion of claim 2, wherein the heavy chain variable region comprises an IGHV3-7 human germline scaffold into which the HCDR1, HCDR2 and HCDR3 sequences have been inserted.

4. The antibody molecule or antigen-binding portion of claim 2, wherein the light chain variable region comprises an IGKV3-11 human germline scaffold into which the LCDR1, LCDR2 and LCDR3 sequences have been inserted.

5. The antibody molecule or antigen-binding portion of claim 2, wherein the heavy chain variable region comprises an IGHV3-7 human germline scaffold into which the HCDR1, HCDR2 and HCDR3 sequences have been inserted; and wherein the light chain variable region comprises an IGKV3-11 human germline scaffold into which the LCDR1, LCDR2 and LCDR3 sequences have been inserted.

6. The antibody molecule or antigen-binding portion of claim 1, wherein the antibody molecule or antigen-binding portion specifically binds to cynomolgus GITR.

7. The antibody molecule or antigen-binding portion of claim 1, wherein the antibody molecule or antigen-binding portion is human, humanized or chimeric.

8. The antibody molecule or antigen-binding portion of claim 1, further comprising a constant region.

9. The antibody molecule or antigen-binding portion of claim 1, further comprising an immunologically inert constant region.

10. The antibody molecule or antigen-binding portion of claim 1, wherein the antibody molecule or antigen-binding portion is a Fab fragment, a F(ab)2 fragment, an Fv fragment, an scFv, a tetrameric antibody, a tetravalent antibody, a multispecific antibody, a bis-scFv or a diabody.

11. The antibody molecule or antigen-binding portion of claim 1, wherein the antibody molecule or antigen-binding portion has improved GITR activation compared to a humanized murine anti-GITR IgG antibody comprising a heavy chain variable region of SEQ ID NO:87 and a light chain variable region of SEQ ID NO:92.

12. The antibody molecule or antigen-binding portion of claim 1, wherein the antibody molecule or antigen-binding portion has improved in silico immunogenicity compared to a humanized murine anti-GITR IgG antibody comprising a heavy chain variable region of SEQ ID NO:87 and a light chain variable region of SEQ ID NO:92.

13. The antibody molecule or antigen-binding portion of claim 1, wherein the antibody molecule or antigen-binding portion has improved affinity for cynomolgus GITR compared to a humanized murine anti-GITR IgG antibody comprising a heavy chain variable region of SEQ ID NO:87 and a light chain variable region of SEQ ID NO:92.

14. A pharmaceutical composition comprising the antibody molecule or antigen-binding portion of claim 1.

15. The pharmaceutical composition of claim 14, further comprising a pharmaceutically acceptable excipient, carrier, buffer or stabilizer.

16. The pharmaceutical composition of claim 14, wherein the antibody molecule or antigen-binding portion is further linked to a therapeutic agent.

17. The pharmaceutical composition of claim 16, wherein the therapeutic agent is a cytotoxin, a radioisotope, a chemotherapeutic agent, an immunomodulatory agent, an anti-angiogenic agent, an antiproliferative agent, a pro-apoptotic agent, a cytostatic enzyme, a cytolytic enzyme or a therapeutic nucleic acid.

18. A nucleic acid molecule encoding the antibody molecule or antigen-binding portion of claim 1.

19. A method for treating cancer in a subject, comprising administering to the subject an effective amount of the antibody molecule or antigen-binding portion of claim 1.

20. The method of claim 19, wherein the cancer is pancreatic cancer, melanoma, breast cancer, lung cancer, bronchial cancer, colorectal cancer, prostate cancer, stomach cancer, ovarian cancer, urinary bladder cancer, brain cancer, central nervous system cancer, peripheral nervous system cancer, esophageal cancer, cervical cancer, uterine cancer, endometrial cancer, cancer of the oral cavity or pharynx, liver cancer, kidney cancer, testicular cancer, biliary tract cancer, small bowel cancer, appendix cancer, salivary gland cancer, thyroid gland cancer, adrenal gland cancer, osteosarcoma, chondrosarcoma or cancer of hematological tissues.

* * * * *

SEQUENCE LISTING

```
<160> NUMBER OF SEQ ID NOS: 174

<210> SEQ ID NO 1
<211> LENGTH: 12
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Xaa is Ser or a conservative substitution of
      Ser
<220> FEATURE:
<221> NAME/KEY: VARIANT
<222> LOCATION: (4)..(4)
<223> OTHER INFORMATION: Xaa is Leu or a conservative substitution of
      Leu
<220> FEATURE:
<221> NAME/KEY: VARIANT
<222> LOCATION: (6)..(6)
<223> OTHER INFORMATION: Xaa is Thr or a conservative substitution of
      Thr
<220> FEATURE:
<221> NAME/KEY: VARIANT
<222> LOCATION: (7)..(7)
<223> OTHER INFORMATION: Xaa is Ser or any amino acid (for example, Phe)
<220> FEATURE:
<221> NAME/KEY: VARIANT
<222> LOCATION: (8)..(8)
<223> OTHER INFORMATION: Xaa is Gly or a conservative substitution of
      Gly
<220> FEATURE:
```

```
<221> NAME/KEY: VARIANT
<222> LOCATION: (9)..(9)
<223> OTHER INFORMATION: Xaa is Met or any amino acid (for example, Tyr,
      Phe, Leu or Trp)
<220> FEATURE:
<221> NAME/KEY: VARIANT
<222> LOCATION: (10)..(10)
<223> OTHER INFORMATION: Xaa is Gly or a conservative substitution of
      Gly
<220> FEATURE:
<221> NAME/KEY: VARIANT
<222> LOCATION: (11)..(11)
<223> OTHER INFORMATION: Xaa is Val or a conservative substitution of
      Val
<220> FEATURE:
<221> NAME/KEY: VARIANT
<222> LOCATION: (12)..(12)
<223> OTHER INFORMATION: Xaa is Gly or a conservative substitution of
      Gly

<400> SEQUENCE: 1

Gly Phe Xaa Xaa Ser Xaa Xaa Xaa Xaa Xaa Xaa Xaa
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Leu or a conservative substitution of
      Leu
<220> FEATURE:
<221> NAME/KEY: VARIANT
<222> LOCATION: (2)..(2)
<223> OTHER INFORMATION: Xaa is Ala or a conservative substitution of
      Ala
<220> FEATURE:
<221> NAME/KEY: VARIANT
<222> LOCATION: (3)..(3)
<223> OTHER INFORMATION: Xaa is His or a conservative substitution of
      His
<220> FEATURE:
<221> NAME/KEY: VARIANT
<222> LOCATION: (4)..(4)
<223> OTHER INFORMATION: Xaa is Asp or a conservative substitution of
      Asp
<220> FEATURE:
<221> NAME/KEY: VARIANT
<222> LOCATION: (7)..(7)
<223> OTHER INFORMATION: Xaa is Asp or a conservative substitution of
      Asp
<220> FEATURE:
<221> NAME/KEY: VARIANT
<222> LOCATION: (8)..(8)
<223> OTHER INFORMATION: Xaa is Asp or a conservative substitution of
      Asp
<220> FEATURE:
<221> NAME/KEY: VARIANT
<222> LOCATION: (9)..(9)
<223> OTHER INFORMATION: Xaa is Asp or a conservative substitution of
      Asp
<220> FEATURE:
<221> NAME/KEY: VARIANT
<222> LOCATION: (13)..(13)
<223> OTHER INFORMATION: Xaa is Asn or any amino acid (for example, Val)
<220> FEATURE:
<221> NAME/KEY: VARIANT
<222> LOCATION: (14)..(14)
<223> OTHER INFORMATION: Xaa is Pro or any amino acid (for example, Asp)
<220> FEATURE:
<221> NAME/KEY: VARIANT
<222> LOCATION: (16)..(16)
<223> OTHER INFORMATION: Xaa is Leu or a conservative substitution of
```

```
        Leu
<220> FEATURE:
<221> NAME/KEY: VARIANT
<222> LOCATION: (18)..(18)
<223> OTHER INFORMATION: Xaa is Ser or any amino acid (for example, Gly)

<400> SEQUENCE: 2

Xaa Xaa Xaa Xaa Trp Trp Xaa Xaa Xaa Lys Tyr Tyr Xaa Xaa Lys Xaa
1               5                   10                  15

Lys Xaa

<210> SEQ ID NO 3
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Thr or any amino acid (for example, Gly,
      Ala, Asn, Ser or Ile)
<220> FEATURE:
<221> NAME/KEY: VARIANT
<222> LOCATION: (2)..(2)
<223> OTHER INFORMATION: Xaa is Arg or any amino acid (for example, Asp,
      Thr or Val)
<220> FEATURE:
<221> NAME/KEY: VARIANT
<222> LOCATION: (3)..(3)
<223> OTHER INFORMATION: Xaa is Arg or any amino acid (for example, Gln,
      Leu, Met, Ile or Val)
<220> FEATURE:
<221> NAME/KEY: VARIANT
<222> LOCATION: (5)..(5)
<223> OTHER INFORMATION: Xaa is Phe or a conservative substitution of
      Phe

<400> SEQUENCE: 3

Xaa Xaa Xaa Tyr Xaa Pro Phe Ala Tyr
1               5

<210> SEQ ID NO 4
<211> LENGTH: 12
<212> TYPE: PRT
<213> ORGANISM: Mus musculus

<400> SEQUENCE: 4

Gly Phe Ser Leu Ser Thr Ser Gly Met Gly Val Gly
1               5                   10

<210> SEQ ID NO 5
<211> LENGTH: 18
<212> TYPE: PRT
<213> ORGANISM: Mus musculus

<400> SEQUENCE: 5

Leu Ala His Ile Trp Trp Asp Asp Asp Lys Tyr Tyr Asn Pro Ser Leu
1               5                   10                  15

Lys Ser

<210> SEQ ID NO 6
<211> LENGTH: 9
<212> TYPE: PRT
<213> ORGANISM: Mus musculus

<400> SEQUENCE: 6

Thr Arg Arg Tyr Phe Pro Phe Ala Tyr
```

```
<210> SEQ ID NO 7
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (6)..(6)
<223> OTHER INFORMATION: Xaa is Ser or Phe

<400> SEQUENCE: 7

Phe Ser Leu Ser Thr Xaa Gly Tyr Gly
1               5

<210> SEQ ID NO 8
<211> LENGTH: 15
<212> TYPE: PRT
<213> ORGANISM: Artificial Sequence
<220> FEATURE:
<223> OTHER INFORMATION: Modified CDR

<400> SEQUENCE: 8

Ile Trp Trp Asp Asp Asp Lys Tyr Tyr Val Asp Ser Val Lys Gly
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Xaa is Gln, Leu or Val

<400> SEQUENCE: 9

Thr Arg Xaa Tyr Phe Pro Phe Ala
1               5

<210> SEQ ID NO 10
<211> LENGTH: 11
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Lys or a conservative substitution of
      Lys
<220> FEATURE:
<221> NAME/KEY: VARIANT
<222> LOCATION: (2)..(2)
<223> OTHER INFORMATION: Xaa is Ala or a conservative substitution of
      Ala
<220> FEATURE:
<221> NAME/KEY: VARIANT
<222> LOCATION: (5)..(5)
<223> OTHER INFORMATION: Xaa is Asn or a conservative substitution of
      Asn
<220> FEATURE:
<221> NAME/KEY: VARIANT
<222> LOCATION: (7)..(7)
<223> OTHER INFORMATION: Xaa is Gly or a conservative substitution of
      Gly
<220> FEATURE:
<221> NAME/KEY: VARIANT
<222> LOCATION: (8)..(8)
```

```
<223> OTHER INFORMATION: Xaa is Thr or a conservative substitution of
      Thr
<220> FEATURE:
<221> NAME/KEY: VARIANT
<222> LOCATION: (9)..(9)
<223> OTHER INFORMATION: Xaa is Asn or any amino acid (for example, Tyr)
<220> FEATURE:
<221> NAME/KEY: VARIANT
<222> LOCATION: (10)..(10)
<223> OTHER INFORMATION: Xaa is Val or a conservative substitution of
      Val

<400> SEQUENCE: 10

Xaa Xaa Ser Gln Xaa Val Xaa Xaa Xaa Xaa Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Ser or any amino acid (for example Tyr,
      Glu, Asp, Phe, Leu or Asn)
<220> FEATURE:
<221> NAME/KEY: VARIANT
<222> LOCATION: (3)..(3)
<223> OTHER INFORMATION: Xaa is Ser or any amino acid (for example, Tyr)
<220> FEATURE:
<221> NAME/KEY: VARIANT
<222> LOCATION: (4)..(4)
<223> OTHER INFORMATION: Xaa is Tyr or any amino acid (for example, Asn)
<220> FEATURE:
<221> NAME/KEY: VARIANT
<222> LOCATION: (6)..(6)
<223> OTHER INFORMATION: Xaa is Tyr or any amino acid (for example Ala
      or Asp)
<220> FEATURE:
<221> NAME/KEY: VARIANT
<222> LOCATION: (7)..(7)
<223> OTHER INFORMATION: Xaa is Ser or a conservative substitution of
      Ser

<400> SEQUENCE: 11

Xaa Ala Xaa Xaa Arg Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (2)..(2)
<223> OTHER INFORMATION: Xaa is Gln or a conservative substitution of
      Gln
<220> FEATURE:
<221> NAME/KEY: VARIANT
<222> LOCATION: (3)..(3)
<223> OTHER INFORMATION: Xaa is Tyr or any amino acid (for example, Arg
      or His)
<220> FEATURE:
<221> NAME/KEY: VARIANT
<222> LOCATION: (4)..(4)
<223> OTHER INFORMATION: Xaa is Asn or a conservative substitution of
      Asn
<220> FEATURE:
<221> NAME/KEY: VARIANT
<222> LOCATION: (5)..(5)
<223> OTHER INFORMATION: Xaa is Thr or any amino acid (for example Lys
```

```
                                or Asn)
<220> FEATURE:
<221> NAME/KEY: VARIANT
<222> LOCATION: (6)..(6)
<223> OTHER INFORMATION: Xaa is Asp or any amino acid (for example, Trp,
      Leu, Ser, Glu, Val or Asn)

<400> SEQUENCE: 12

Gln Xaa Xaa Xaa Xaa Xaa Pro Leu Thr
1               5

<210> SEQ ID NO 13
<211> LENGTH: 11
<212> TYPE: PRT
<213> ORGANISM: Mus musculus

<400> SEQUENCE: 13

Lys Ala Ser Gln Asn Val Gly Thr Asn Val Ala
1               5                   10

<210> SEQ ID NO 14
<211> LENGTH: 7
<212> TYPE: PRT
<213> ORGANISM: Mus musculus

<400> SEQUENCE: 14

Ser Ala Ser Tyr Arg Tyr Ser
1               5

<210> SEQ ID NO 15
<211> LENGTH: 9
<212> TYPE: PRT
<213> ORGANISM: Mus musculus

<400> SEQUENCE: 15

Gln Gln Tyr Asn Thr Asp Pro Leu Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (4)..(4)
<223> OTHER INFORMATION: Xaa is Asn or Ser
<220> FEATURE:
<221> NAME/KEY: VARIANT
<222> LOCATION: (7)..(7)
<223> OTHER INFORMATION: Xaa is Thr or Ser

<400> SEQUENCE: 16

Ala Ser Gln Xaa Val Gly Xaa Asn
1               5

<210> SEQ ID NO 17
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Ser or Tyr
<220> FEATURE:
<221> NAME/KEY: VARIANT
```

```
<222> LOCATION: (4)..(4)
<223> OTHER INFORMATION: Xaa is Tyr or Asn
<220> FEATURE:
<221> NAME/KEY: VARIANT
<222> LOCATION: (7)..(7)
<223> OTHER INFORMATION: Xaa is Ser or Thr

<400> SEQUENCE: 17

Xaa Ala Ser Xaa Arg Tyr Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Xaa is Thr or Asn

<400> SEQUENCE: 18

Tyr Ser Xaa Asp Pro Leu
1               5

<210> SEQ ID NO 19
<211> LENGTH: 12
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Xaa is Ser or Thr
<220> FEATURE:
<221> NAME/KEY: VARIANT
<222> LOCATION: (4)..(4)
<223> OTHER INFORMATION: Xaa is Leu or Phe
<220> FEATURE:
<221> NAME/KEY: VARIANT
<222> LOCATION: (6)..(6)
<223> OTHER INFORMATION: Xaa is Thr or Ala
<220> FEATURE:
<221> NAME/KEY: VARIANT
<222> LOCATION: (7)..(7)
<223> OTHER INFORMATION: Xaa is Ser or Phe
<220> FEATURE:
<221> NAME/KEY: VARIANT
<222> LOCATION: (8)..(8)
<223> OTHER INFORMATION: Xaa is Gly or Ser
<220> FEATURE:
<221> NAME/KEY: VARIANT
<222> LOCATION: (9)..(9)
<223> OTHER INFORMATION: Xaa is Met, Tyr, Phe, Leu or Trp
<220> FEATURE:
<221> NAME/KEY: VARIANT
<222> LOCATION: (10)..(10)
<223> OTHER INFORMATION: Xaa is Gly or Ala
<220> FEATURE:
<221> NAME/KEY: VARIANT
<222> LOCATION: (11)..(11)
<223> OTHER INFORMATION: Xaa is Val or Met
<220> FEATURE:
<221> NAME/KEY: VARIANT
<222> LOCATION: (12)..(12)
<223> OTHER INFORMATION: Xaa is Gly or Ser

<400> SEQUENCE: 19

Gly Phe Xaa Xaa Ser Xaa Xaa Xaa Xaa Xaa Xaa Xaa
1               5                   10
```

-continued

```
<210> SEQ ID NO 20
<211> LENGTH: 18
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Leu or Val
<220> FEATURE:
<221> NAME/KEY: VARIANT
<222> LOCATION: (2)..(2)
<223> OTHER INFORMATION: Xaa is Ala or Ser
<220> FEATURE:
<221> NAME/KEY: VARIANT
<222> LOCATION: (3)..(3)
<223> OTHER INFORMATION: Xaa is His or Asn
<220> FEATURE:
<221> NAME/KEY: VARIANT
<222> LOCATION: (4)..(4)
<223> OTHER INFORMATION: Xaa is Ile or Val
<220> FEATURE:
<221> NAME/KEY: VARIANT
<222> LOCATION: (7)..(7)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Asp or Ser
<220> FEATURE:
<221> NAME/KEY: VARIANT
<222> LOCATION: (9)..(9)
<223> OTHER INFORMATION: Xaa is Asp or Glu
<220> FEATURE:
<221> NAME/KEY: VARIANT
<222> LOCATION: (13)..(13)
<223> OTHER INFORMATION: Xaa is Asn or Val
<220> FEATURE:
<221> NAME/KEY: VARIANT
<222> LOCATION: (14)..(14)
<223> OTHER INFORMATION: Xaa is Pro or Asp
<220> FEATURE:
<221> NAME/KEY: VARIANT
<222> LOCATION: (16)..(16)
<223> OTHER INFORMATION: Xaa is Leu or Val
<220> FEATURE:
<221> NAME/KEY: VARIANT
<222> LOCATION: (18)..(18)
<223> OTHER INFORMATION: Xaa is Ser or Gly

<400> SEQUENCE: 20

Xaa Xaa Xaa Xaa Trp Trp Xaa Xaa Xaa Lys Tyr Tyr Xaa Xaa Ser Xaa
1               5                   10                  15

Lys Xaa

<210> SEQ ID NO 21
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Thr, Gly, Ala, Asn, Ser or Ile
<220> FEATURE:
<221> NAME/KEY: VARIANT
<222> LOCATION: (2)..(2)
<223> OTHER INFORMATION: Xaa is Arg, Asp, Thr or Val
<220> FEATURE:
<221> NAME/KEY: VARIANT
<222> LOCATION: (3)..(3)
<223> OTHER INFORMATION: Xaa is Arg, Gln, Leu, Met, Ile or Val
<220> FEATURE:
<221> NAME/KEY: VARIANT
```

```
<222> LOCATION: (5)..(5)
<223> OTHER INFORMATION: Xaa is Phe or Tyr

<400> SEQUENCE: 21

Xaa Xaa Xaa Tyr Xaa Pro Phe Ala Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Lys or Arg
<220> FEATURE:
<221> NAME/KEY: VARIANT
<222> LOCATION: (2)..(2)
<223> OTHER INFORMATION: Xaa is Ala or Thr
<220> FEATURE:
<221> NAME/KEY: VARIANT
<222> LOCATION: (5)..(5)
<223> OTHER INFORMATION: Xaa is Asn, Asp or Ser
<220> FEATURE:
<221> NAME/KEY: VARIANT
<222> LOCATION: (7)..(7)
<223> OTHER INFORMATION: Xaa is Gly or Ser
<220> FEATURE:
<221> NAME/KEY: VARIANT
<222> LOCATION: (8)..(8)
<223> OTHER INFORMATION: Xaa is Thr, Ser or Asn
<220> FEATURE:
<221> NAME/KEY: VARIANT
<222> LOCATION: (9)..(9)
<223> OTHER INFORMATION: Xaa is Asn or Tyr
<220> FEATURE:
<221> NAME/KEY: VARIANT
<222> LOCATION: (10)..(10)
<223> OTHER INFORMATION: Xaa is Val or Leu

<400> SEQUENCE: 22

Xaa Xaa Ser Gln Xaa Val Xaa Xaa Xaa Xaa Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Ser, Tyr, Glu, Asp, Phe, Leu or Asn
<220> FEATURE:
<221> NAME/KEY: VARIANT
<222> LOCATION: (3)..(3)
<223> OTHER INFORMATION: Xaa is Ser or Tyr
<220> FEATURE:
<221> NAME/KEY: VARIANT
<222> LOCATION: (4)..(4)
<223> OTHER INFORMATION: Xaa is Tyr or Asn
<220> FEATURE:
<221> NAME/KEY: VARIANT
<222> LOCATION: (6)..(6)
<223> OTHER INFORMATION: Xaa is Tyr, Ala or Asp
<220> FEATURE:
<221> NAME/KEY: VARIANT
<222> LOCATION: (7)..(7)
<223> OTHER INFORMATION: Xaa is Ser or Thr

<400> SEQUENCE: 23
```

Xaa Ala Xaa Xaa Arg Xaa Xaa
1               5

<210> SEQ ID NO 24
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (2)..(2)
<223> OTHER INFORMATION: Xaa is Gln or His
<220> FEATURE:
<221> NAME/KEY: VARIANT
<222> LOCATION: (3)..(3)
<223> OTHER INFORMATION: Xaa is Tyr, Arg or His
<220> FEATURE:
<221> NAME/KEY: VARIANT
<222> LOCATION: (4)..(4)
<223> OTHER INFORMATION: Xaa is Asn, Ser or Arg
<220> FEATURE:
<221> NAME/KEY: VARIANT
<222> LOCATION: (5)..(5)
<223> OTHER INFORMATION: Xaa is Thr, Lys or Asn
<220> FEATURE:
<221> NAME/KEY: VARIANT
<222> LOCATION: (6)..(6)
<223> OTHER INFORMATION: Xaa is Asp, Trp, Leu, Ser, Glu, Val or Asn

<400> SEQUENCE: 24

Gln Xaa Xaa Xaa Xaa Xaa Pro Leu Thr
1               5

<210> SEQ ID NO 25
<211> LENGTH: 12
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (7)..(7)
<223> OTHER INFORMATION: Xaa is Ser or Phe

<400> SEQUENCE: 25

Gly Phe Ser Leu Ser Thr Xaa Gly Tyr Gly Val Gly
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Modified CDR

<400> SEQUENCE: 26

Leu Ala His Ile Trp Trp Asp Asp Asp Lys Tyr Tyr Val Asp Ser Val
1               5                   10                  15

Lys Gly

<210> SEQ ID NO 27
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (3)..(3)
<223> OTHER INFORMATION: Xaa is Gln, Leu or Val

<400> SEQUENCE: 27

Thr Arg Xaa Tyr Phe Pro Phe Ala Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: Xaa is Asn or Ser
<220> FEATURE:
<221> NAME/KEY: VARIANT
<222> LOCATION: (8)..(8)
<223> OTHER INFORMATION: Xaa is Thr or Ser

<400> SEQUENCE: 28

Arg Ala Ser Gln Xaa Val Gly Xaa Asn Leu Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Modified CDR

<400> SEQUENCE: 29

Gly Phe Ser Leu Ser Thr Ser Gly Tyr Gly Val Gly
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (1)..(1)
<223> OTHER INFORMATION: Xaa is Leu or Val
<220> FEATURE:
<221> NAME/KEY: VARIANT
<222> LOCATION: (2)..(2)
<223> OTHER INFORMATION: Xaa is Ala or Ser
<220> FEATURE:
<221> NAME/KEY: VARIANT
<222> LOCATION: (3)..(3)
<223> OTHER INFORMATION: Xaa is His or Asn
<220> FEATURE:
<221> NAME/KEY: VARIANT
<222> LOCATION: (4)..(4)
<223> OTHER INFORMATION: Xaa is Ile or Val
<220> FEATURE:
<221> NAME/KEY: VARIANT
<222> LOCATION: (7)..(7)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Asp or Ser
<220> FEATURE:
<221> NAME/KEY: VARIANT
<222> LOCATION: (9)..(9)
<223> OTHER INFORMATION: Xaa is Asp or Glu

<400> SEQUENCE: 30

Xaa Xaa Xaa Xaa Trp Trp Xaa Xaa Xaa Lys Tyr Tyr Val Asp Ser Val

```
1               5                   10                  15
Lys Gly

<210> SEQ ID NO 31
<211> LENGTH: 9
<212> TYPE: PRT
<213> ORGANISM: Artificial Sequence
<220> FEATURE:
<223> OTHER INFORMATION: Modified CDR

<400> SEQUENCE: 31

Thr Arg Gln Tyr Phe Pro Phe Ala Tyr
1               5

<210> SEQ ID NO 32
<211> LENGTH: 11
<212> TYPE: PRT
<213> ORGANISM: Artificial Sequence
<220> FEATURE:
<223> OTHER INFORMATION: Modified CDR

<400> SEQUENCE: 32

Arg Ala Ser Gln Ser Val Gly Ser Asn Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Modified CDR

<400> SEQUENCE: 33

Ser Ala Ser Tyr Arg Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Modified CDR

<400> SEQUENCE: 34

Gln Gln Tyr Ser Thr Asp Pro Leu Thr
1               5

<210> SEQ ID NO 35
<211> LENGTH: 12
<212> TYPE: PRT
<213> ORGANISM: Artificial Sequence
<220> FEATURE:
<223> OTHER INFORMATION: Modified CDR

<400> SEQUENCE: 35

Gly Phe Ser Leu Ser Thr Phe Gly Tyr Gly Val Gly
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Modified CDR

<400> SEQUENCE: 36
```

Arg Ala Ser Gln Ser Val Gly Thr Asn Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Modified CDR

<400> SEQUENCE: 37

Tyr Ala Ser Tyr Arg Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Modified CDR

<400> SEQUENCE: 38

Gln Gln Tyr Ser Asn Asp Pro Leu Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Modified CDR

<400> SEQUENCE: 39

Thr Arg Leu Tyr Phe Pro Phe Ala Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: Modified CDR

<400> SEQUENCE: 40

Arg Ala Ser Gln Asn Val Gly Ser Asn Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Modified CDR

<400> SEQUENCE: 41

Ser Ala Ser Asn Arg Tyr Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Modified CDR

<400> SEQUENCE: 42

Thr Arg Val Tyr Phe Pro Phe Ala Tyr

<210> SEQ ID NO 43
<211> LENGTH: 11
<212> TYPE: PRT
<213> ORGANISM: Artificial Sequence
<220> FEATURE:
<223> OTHER INFORMATION: Modified CDR

<400> SEQUENCE: 43

Arg Ala Ser Gln Asn Val Gly Thr Asn Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Modified CDR

<400> SEQUENCE: 44

Ser Ala Ser Asn Arg Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Modified CDR

<400> SEQUENCE: 45

Asn Arg Arg Tyr Phe Pro Phe Ala Tyr
1               5

<210> SEQ ID NO 46
<211> LENGTH: 7
<212> TYPE: PRT
<213> ORGANISM: Artificial Sequence
<220> FEATURE:
<223> OTHER INFORMATION: Modified CDR

<400> SEQUENCE: 46

Ser Ala Ser Tyr Arg Ala Thr
1               5

<210> SEQ ID NO 47
<211> LENGTH: 12
<212> TYPE: PRT
<213> ORGANISM: Artificial Sequence
<220> FEATURE:
<223> OTHER INFORMATION: Modified CDR

<400> SEQUENCE: 47

Gly Phe Ser Leu Ser Thr Ser Gly Tyr Gly Val Ser
1               5                   10

<210> SEQ ID NO 48
<211> LENGTH: 18
<212> TYPE: PRT
<213> ORGANISM: Artificial Sequence
<220> FEATURE:
<223> OTHER INFORMATION: Modified CDR

<400> SEQUENCE: 48

Leu Ala His Val Trp Trp Asp Asp Glu Lys Tyr Tyr Val Asp Ser Val
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Modified CDR

<400> SEQUENCE: 49

Arg Ala Ser Gln Ser Val Gly Thr Asn Val Ala
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Modified CDR

<400> SEQUENCE: 50

Gln Gln Tyr Asn Asn Trp Pro Leu Thr
1               5

<210> SEQ ID NO 51
<211> LENGTH: 12
<212> TYPE: PRT
<213> ORGANISM: Artificial Sequence
<220> FEATURE:
<223> OTHER INFORMATION: Modified CDR

<400> SEQUENCE: 51

Gly Phe Ser Phe Ser Thr Ser Gly Tyr Gly Val Ser
1               5                   10

<210> SEQ ID NO 52
<211> LENGTH: 18
<212> TYPE: PRT
<213> ORGANISM: Artificial Sequence
<220> FEATURE:
<223> OTHER INFORMATION: Modified CDR

<400> SEQUENCE: 52

Leu Ala His Ile Trp Trp Asp Asp Glu Lys Tyr Tyr Val Asp Ser Val
1               5                   10                  15

Lys Gly

<210> SEQ ID NO 53
<211> LENGTH: 7
<212> TYPE: PRT
<213> ORGANISM: Artificial Sequence
<220> FEATURE:
<223> OTHER INFORMATION: Modified CDR

<400> SEQUENCE: 53

Ser Ala Ser Tyr Arg Ala Ser
1               5

<210> SEQ ID NO 54
<211> LENGTH: 12
<212> TYPE: PRT
<213> ORGANISM: Artificial Sequence
<220> FEATURE:
<223> OTHER INFORMATION: Modified CDR

<400> SEQUENCE: 54

Gly Phe Ser Leu Ser Thr Ser Gly Met Gly Val Ser
1               5                   10

<210> SEQ ID NO 55
<211> LENGTH: 18
<212> TYPE: PRT
<213> ORGANISM: Artificial Sequence
<220> FEATURE:
<223> OTHER INFORMATION: Modified CDR

<400> SEQUENCE: 55

Val Ala His Ile Trp Trp Asp Asp Glu Lys Tyr Tyr Val Asp Ser Val
1               5                   10                  15

Lys Gly

<210> SEQ ID NO 56
<211> LENGTH: 12
<212> TYPE: PRT
<213> ORGANISM: Artificial Sequence
<220> FEATURE:
<223> OTHER INFORMATION: Modified CDR

<400> SEQUENCE: 56

Gly Phe Ser Phe Ser Thr Ser Gly Met Gly Val Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Modified CDR

<400> SEQUENCE: 57

Arg Ala Ser Gln Ser Val Gly Ser Asn Val Ala
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Modified CDR

<400> SEQUENCE: 58

Gly Phe Ser Leu Ser Thr Ser Gly Met Gly Met Gly
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Modified CDR

<400> SEQUENCE: 59

Ser Arg Arg Tyr Phe Pro Phe Ala Tyr
1               5

<210> SEQ ID NO 60
<211> LENGTH: 12
<212> TYPE: PRT
<213> ORGANISM: Artificial Sequence
<220> FEATURE:
<223> OTHER INFORMATION: Modified CDR -continued

<400> SEQUENCE: 60

Gly Phe Ser Leu Ser Thr Ser Ser Tyr Gly Val Ser
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Modified CDR

<400> SEQUENCE: 61

Gly Phe Ser Leu Ser Thr Ser Gly Met Gly Met Ser
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Modified CDR

<400> SEQUENCE: 62

Gly Phe Ser Leu Ser Thr Ser Gly Tyr Gly Met Ser
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Modified CDR

<400> SEQUENCE: 63

Gln Gln Tyr Ser Thr Asn Pro Leu Thr
1               5

<210> SEQ ID NO 64
<211> LENGTH: 12
<212> TYPE: PRT
<213> ORGANISM: Artificial Sequence
<220> FEATURE:
<223> OTHER INFORMATION: Modified CDR

<400> SEQUENCE: 64

Gly Phe Ser Leu Ser Thr Ser Gly Tyr Gly Met Gly
1               5                   10

<210> SEQ ID NO 65
<211> LENGTH: 18
<212> TYPE: PRT
<213> ORGANISM: Artificial Sequence
<220> FEATURE:
<223> OTHER INFORMATION: Modified CDR

<400> SEQUENCE: 65

Leu Ala His Ile Trp Trp Asp Asp Asp Lys Tyr Tyr Gln Pro Ser Leu
1               5                   10                  15

Lys Ser

<210> SEQ ID NO 66
<211> LENGTH: 7
<212> TYPE: PRT
<213> ORGANISM: Mus musculus

<400> SEQUENCE: 66

Thr Ser Gly Met Gly Val Gly
1               5

<210> SEQ ID NO 67
<211> LENGTH: 16
<212> TYPE: PRT
<213> ORGANISM: Mus musculus

<400> SEQUENCE: 67

His Ile Trp Trp Asp Asp Asp Lys Tyr Tyr Asn Pro Ser Leu Lys Ser
1               5                   10                  15

<210> SEQ ID NO 68
<211> LENGTH: 9
<212> TYPE: PRT
<213> ORGANISM: Mus musculus

<400> SEQUENCE: 68

Gly Phe Ser Leu Ser Thr Ser Gly Met
1               5

<210> SEQ ID NO 69
<211> LENGTH: 6
<212> TYPE: PRT
<213> ORGANISM: Mus musculus

<400> SEQUENCE: 69

Trp Trp Asp Asp Asp Lys
1               5

<210> SEQ ID NO 70
<211> LENGTH: 11
<212> TYPE: PRT
<213> ORGANISM: Mus musculus

<400> SEQUENCE: 70

Ala Arg Thr Arg Arg Tyr Phe Pro Phe Ala Tyr
1               5                   10

<210> SEQ ID NO 71
<211> LENGTH: 10
<212> TYPE: PRT
<213> ORGANISM: Mus musculus

<400> SEQUENCE: 71

Gly Phe Ser Leu Ser Thr Ser Gly Met Gly
1               5                   10

<210> SEQ ID NO 72
<211> LENGTH: 7
<212> TYPE: PRT
<213> ORGANISM: Mus musculus

<400> SEQUENCE: 72

Ile Trp Trp Asp Asp Asp Lys
1               5

<210> SEQ ID NO 73
<211> LENGTH: 6
<212> TYPE: PRT
<213> ORGANISM: Mus musculus

<400> SEQUENCE: 73

Gln Asn Val Gly Thr Asn

-continued

```
<210> SEQ ID NO 74
<211> LENGTH: 9
<212> TYPE: PRT
<213> ORGANISM: Mus musculus

<400> SEQUENCE: 74

Phe Ser Leu Ser Thr Ser Gly Met Gly
1               5

<210> SEQ ID NO 75
<211> LENGTH: 15
<212> TYPE: PRT
<213> ORGANISM: Mus musculus

<400> SEQUENCE: 75

Ile Trp Trp Asp Asp Asp Lys Tyr Tyr Asn Pro Ser Leu Lys Ser
1               5                   10                  15

<210> SEQ ID NO 76
<211> LENGTH: 8
<212> TYPE: PRT
<213> ORGANISM: Mus musculus

<400> SEQUENCE: 76

Thr Arg Arg Tyr Phe Pro Phe Ala
1               5

<210> SEQ ID NO 77
<211> LENGTH: 8
<212> TYPE: PRT
<213> ORGANISM: Mus musculus

<400> SEQUENCE: 77

Ala Ser Gln Asn Val Gly Thr Asn
1               5

<210> SEQ ID NO 78
<211> LENGTH: 6
<212> TYPE: PRT
<213> ORGANISM: Mus musculus

<400> SEQUENCE: 78

Tyr Asn Thr Asp Pro Leu
1               5

<210> SEQ ID NO 79
<211> LENGTH: 10
<212> TYPE: PRT
<213> ORGANISM: Mus musculus

<400> SEQUENCE: 79

His Ile Trp Trp Asp Asp Asp Lys Tyr Tyr
1               5                   10

<210> SEQ ID NO 80
<211> LENGTH: 8
<212> TYPE: PRT
<213> ORGANISM: Mus musculus

<400> SEQUENCE: 80

Ser Thr Ser Gly Met Gly Val Gly
1               5
```

<210> SEQ ID NO 81
<211> LENGTH: 12
<212> TYPE: PRT
<213> ORGANISM: Mus musculus

<400> SEQUENCE: 81

Leu Ala His Ile Trp Trp Asp Asp Lys Tyr Tyr
1               5                   10

<210> SEQ ID NO 82
<211> LENGTH: 10
<212> TYPE: PRT
<213> ORGANISM: Mus musculus

<400> SEQUENCE: 82

Ala Arg Thr Arg Arg Tyr Phe Pro Phe Ala
1               5                   10

<210> SEQ ID NO 83
<211> LENGTH: 7
<212> TYPE: PRT
<213> ORGANISM: Mus musculus

<400> SEQUENCE: 83

Gly Thr Asn Val Ala Trp Tyr
1               5

<210> SEQ ID NO 84
<211> LENGTH: 10
<212> TYPE: PRT
<213> ORGANISM: Mus musculus

<400> SEQUENCE: 84

Leu Leu Ile Tyr Ser Ala Ser Tyr Arg Tyr
1               5                   10

<210> SEQ ID NO 85
<211> LENGTH: 8
<212> TYPE: PRT
<213> ORGANISM: Mus musculus

<400> SEQUENCE: 85

Gln Gln Tyr Asn Thr Asp Pro Leu
1               5

<210> SEQ ID NO 86
<211> LENGTH: 119
<212> TYPE: PRT
<213> ORGANISM: Mus musculus

<400> SEQUENCE: 86

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr

-continued

```
                 85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: VH DOMAIN

<400> SEQUENCE: 87

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

<210> SEQ ID NO 88
<211> LENGTH: 117
<212> TYPE: PRT
<213> ORGANISM: Artificial Sequence
<220> FEATURE:
<223> OTHER INFORMATION: VH DOMAIN

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Leu
        35                  40                  45

Ala His Ile Trp Trp Asp Asp Asp Lys Tyr Tyr Val Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Thr Arg Arg Tyr Phe Pro Phe Ala Tyr Trp Gly Gln Gly Thr Leu
            100                 105                 110

Val Thr Val Ser Ser
        115

<210> SEQ ID NO 89
<211> LENGTH: 119
```

```
<212> TYPE: PRT
<213> ORGANISM: Artificial Sequence
<220> FEATURE:
<223> OTHER INFORMATION: VH DOMAIN

<400> SEQUENCE: 89
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Leu Ala His Ile Trp Trp Asp Asp Lys Tyr Tyr Val Asp Ser
50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
            85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

```
<210> SEQ ID NO 90
<211> LENGTH: 119
<212> TYPE: PRT
<213> ORGANISM: Artificial Sequence
<220> FEATURE:
<223> OTHER INFORMATION: VH DOMAIN

<400> SEQUENCE: 90
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Ser Leu Ser Thr Ser
            20                  25                  30

Gly Met Gly Val Gly Trp Val Arg Gln Met Pro Gly Lys Gly Leu Glu
        35                  40                  45

Trp Leu Ala His Ile Trp Trp Asp Asp Lys Tyr Tyr Ser Pro Ser
50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
            85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

```
<210> SEQ ID NO 91
<211> LENGTH: 107
<212> TYPE: PRT
<213> ORGANISM: Mus musculus

<400> SEQUENCE: 91
```

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val His Ser
65                  70                  75                  80

Glu Asp Leu Ala Glu Tyr Phe Cys Gln Gln Tyr Asn Thr Asp Pro Leu
                85                  90                  95

Thr Phe Gly Ala Gly Thr Lys Leu Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: VL DOMAIN

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: VL DOMAIN

<400> SEQUENCE: 93

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Gly Thr Asn
            20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 94

```
<211> LENGTH: 107
<212> TYPE: PRT
<213> ORGANISM: Artificial Sequence
<220> FEATURE:
<223> OTHER INFORMATION: VL DOMAIN

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 95
<211> LENGTH: 9
<212> TYPE: PRT
<213> ORGANISM: Artificial Sequence
<220> FEATURE:
<223> OTHER INFORMATION: Modified CDR

<400> SEQUENCE: 95

Thr Arg Met Tyr Phe Pro Phe Ala Tyr
1               5

<210> SEQ ID NO 96
<211> LENGTH: 12
<212> TYPE: PRT
<213> ORGANISM: Artificial Sequence
<220> FEATURE:
<223> OTHER INFORMATION: Modified CDR

<400> SEQUENCE: 96

Gly Phe Thr Phe Ser Thr Ser Ser Tyr Gly Met Ser
1               5                   10

<210> SEQ ID NO 97
<211> LENGTH: 18
<212> TYPE: PRT
<213> ORGANISM: Artificial Sequence
<220> FEATURE:
<223> OTHER INFORMATION: Modified CDR

<400> SEQUENCE: 97

Leu Ala Asn Ile Trp Trp Asp Asp Glu Lys Tyr Tyr Val Asp Ser Val
1               5                   10                  15

Lys Gly

<210> SEQ ID NO 98
<211> LENGTH: 9
<212> TYPE: PRT
<213> ORGANISM: Artificial Sequence
<220> FEATURE:
<223> OTHER INFORMATION: Modified CDR

<400> SEQUENCE: 98
```

Gln Gln Tyr Asn Asn Asp Pro Leu Thr
1               5

<210> SEQ ID NO 99
<211> LENGTH: 11
<212> TYPE: PRT
<213> ORGANISM: Artificial Sequence
<220> FEATURE:
<223> OTHER INFORMATION: Modified CDR

<400> SEQUENCE: 99

Arg Ala Ser Gln Ser Val Gly Ser Tyr Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Modified CDR

<400> SEQUENCE: 100

Glu Ala Ser Tyr Arg Ala Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Modified CDR

<400> SEQUENCE: 101

Thr Arg Ile Tyr Phe Pro Phe Ala Tyr
1               5

<210> SEQ ID NO 102
<211> LENGTH: 18
<212> TYPE: PRT
<213> ORGANISM: Artificial Sequence
<220> FEATURE:
<223> OTHER INFORMATION: Modified CDR

<400> SEQUENCE: 102

Val Ala Asn Ile Trp Trp Asp Asp Glu Lys Tyr Tyr Val Asp Ser Val
1               5                   10                  15

Lys Gly

<210> SEQ ID NO 103
<211> LENGTH: 11
<212> TYPE: PRT
<213> ORGANISM: Artificial Sequence
<220> FEATURE:
<223> OTHER INFORMATION: Modified CDR

<400> SEQUENCE: 103

Arg Ala Ser Gln Ser Val Gly Thr Tyr Val Ala
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Modified CDR

```
<400> SEQUENCE: 104

Asp Ala Ser Asn Arg Tyr Thr
1               5

<210> SEQ ID NO 105
<211> LENGTH: 12
<212> TYPE: PRT
<213> ORGANISM: Artificial Sequence
<220> FEATURE:
<223> OTHER INFORMATION: Modified CDR

<400> SEQUENCE: 105

Gly Phe Ser Phe Ser Thr Ser Gly Tyr Gly Met Gly
1               5                   10

<210> SEQ ID NO 106
<211> LENGTH: 18
<212> TYPE: PRT
<213> ORGANISM: Artificial Sequence
<220> FEATURE:
<223> OTHER INFORMATION: Modified CDR

<400> SEQUENCE: 106

Leu Ala Asn Ile Trp Trp Asp Asp Asp Lys Tyr Tyr Val Asp Ser Val
1               5                   10                  15

Lys Gly

<210> SEQ ID NO 107
<211> LENGTH: 9
<212> TYPE: PRT
<213> ORGANISM: Artificial Sequence
<220> FEATURE:
<223> OTHER INFORMATION: Modified CDR

<400> SEQUENCE: 107

Gln Gln Tyr Ser Asn Trp Pro Leu Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Modified CDR

<400> SEQUENCE: 108

Ala Arg Arg Tyr Phe Pro Phe Ala Tyr
1               5

<210> SEQ ID NO 109
<211> LENGTH: 9
<212> TYPE: PRT
<213> ORGANISM: Artificial Sequence
<220> FEATURE:
<223> OTHER INFORMATION: Modified CDR

<400> SEQUENCE: 109

Gln Gln Tyr Asn Thr Trp Pro Leu Thr
1               5

<210> SEQ ID NO 110
<211> LENGTH: 12
<212> TYPE: PRT
<213> ORGANISM: Artificial Sequence
<220> FEATURE:
<223> OTHER INFORMATION: Modified CDR
```

<400> SEQUENCE: 110

Gly Phe Ser Leu Ser Thr Ser Ser Met Gly Met Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Modified CDR

<400> SEQUENCE: 111

Arg Ala Ser Gln Asn Val Gly Ser Tyr Val Ala
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Modified CDR

<400> SEQUENCE: 112

Gly Arg Arg Tyr Phe Pro Phe Ala Tyr
1               5

<210> SEQ ID NO 113
<211> LENGTH: 12
<212> TYPE: PRT
<213> ORGANISM: Artificial Sequence
<220> FEATURE:
<223> OTHER INFORMATION: Modified CDR

<400> SEQUENCE: 113

Gly Phe Thr Phe Ser Thr Ser Gly Tyr Gly Met Gly
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Modified CDR

<400> SEQUENCE: 114

Gln Gln Tyr Ser Thr Trp Pro Leu Thr
1               5

<210> SEQ ID NO 115
<211> LENGTH: 12
<212> TYPE: PRT
<213> ORGANISM: Artificial Sequence
<220> FEATURE:
<223> OTHER INFORMATION: Modified CDR

<400> SEQUENCE: 115

Gly Phe Thr Leu Ser Thr Ser Gly Tyr Gly Val Gly
1               5                   10

<210> SEQ ID NO 116
<211> LENGTH: 18
<212> TYPE: PRT
<213> ORGANISM: Artificial Sequence
<220> FEATURE:
<223> OTHER INFORMATION: Modified CDR

```
<400> SEQUENCE: 116

Leu Ala Asn Ile Trp Trp Asp Ser Asp Lys Tyr Tyr Val Asp Ser Val
1               5                   10                  15

Lys Gly

<210> SEQ ID NO 117
<211> LENGTH: 11
<212> TYPE: PRT
<213> ORGANISM: Artificial Sequence
<220> FEATURE:
<223> OTHER INFORMATION: Modified CDR

<400> SEQUENCE: 117

Arg Ala Ser Gln Asn Val Gly Thr Tyr Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Modified CDR

<400> SEQUENCE: 118

Ser Ala Ser Asn Arg Ala Thr
1               5

<210> SEQ ID NO 119
<211> LENGTH: 11
<212> TYPE: PRT
<213> ORGANISM: Artificial Sequence
<220> FEATURE:
<223> OTHER INFORMATION: Modified CDR

<400> SEQUENCE: 119

Arg Ala Ser Gln Asp Val Gly Thr Tyr Leu Ala
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Modified CDR

<400> SEQUENCE: 120

Gly Phe Thr Leu Ser Ala Ser Gly Tyr Gly Met Gly
1               5                   10

<210> SEQ ID NO 121
<211> LENGTH: 18
<212> TYPE: PRT
<213> ORGANISM: Artificial Sequence
<220> FEATURE:
<223> OTHER INFORMATION: Modified CDR

<400> SEQUENCE: 121

Val Ala Asn Ile Trp Trp Asp Asp Lys Tyr Tyr Val Asp Ser Val
1               5                   10                  15

Lys Gly

<210> SEQ ID NO 122
<211> LENGTH: 11
<212> TYPE: PRT
<213> ORGANISM: Artificial Sequence
```

```
<220> FEATURE:
<223> OTHER INFORMATION: Modified CDR

<400> SEQUENCE: 122

Arg Ala Ser Gln Asn Val Gly Ser Tyr Leu Ala
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Modified CDR

<400> SEQUENCE: 123

Arg Ala Ser Gln Asn Val Gly Thr Tyr Val Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Modified CDR

<400> SEQUENCE: 124

Asp Ala Ser Asn Arg Tyr Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Modified CDR

<400> SEQUENCE: 125

Thr Asp Arg Tyr Phe Pro Phe Ala Tyr
1               5

<210> SEQ ID NO 126
<211> LENGTH: 12
<212> TYPE: PRT
<213> ORGANISM: Artificial Sequence
<220> FEATURE:
<223> OTHER INFORMATION: Modified CDR

<400> SEQUENCE: 126

Gly Phe Thr Phe Ser Thr Ser Gly Trp Ala Trp Gly
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Modified CDR

<400> SEQUENCE: 127

Gln Gln Arg Asn Asn Asp Pro Leu Thr
1               5

<210> SEQ ID NO 128
<211> LENGTH: 7
<212> TYPE: PRT
<213> ORGANISM: Artificial Sequence
<220> FEATURE:
```

<223> OTHER INFORMATION: Modified CDR

<400> SEQUENCE: 128

Asp Ala Ser Asn Arg Ala Thr
1               5

<210> SEQ ID NO 129
<211> LENGTH: 12
<212> TYPE: PRT
<213> ORGANISM: Artificial Sequence
<220> FEATURE:
<223> OTHER INFORMATION: Modified CDR

<400> SEQUENCE: 129

Gly Phe Thr Leu Ser Thr Ser Gly Tyr Gly Met Ser
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Modified CDR

<400> SEQUENCE: 130

Ser Ala Ser Asn Arg Ala Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Modified CDR

<400> SEQUENCE: 131

Ile Arg Arg Tyr Phe Pro Phe Ala Tyr
1               5

<210> SEQ ID NO 132
<211> LENGTH: 18
<212> TYPE: PRT
<213> ORGANISM: Artificial Sequence
<220> FEATURE:
<223> OTHER INFORMATION: Modified CDR

<400> SEQUENCE: 132

Leu Ala His Ile Trp Trp Asp Ser Asp Lys Tyr Tyr Val Asp Ser Val
1               5                   10                  15

Lys Gly

<210> SEQ ID NO 133
<211> LENGTH: 12
<212> TYPE: PRT
<213> ORGANISM: Artificial Sequence
<220> FEATURE:
<223> OTHER INFORMATION: Modified CDR

<400> SEQUENCE: 133

Gly Phe Ser Leu Ser Thr Phe Ser Tyr Gly Val Ser
1               5                   10

<210> SEQ ID NO 134
<211> LENGTH: 7
<212> TYPE: PRT
<213> ORGANISM: Artificial Sequence

```
<220> FEATURE:
<223> OTHER INFORMATION: Modified CDR

<400> SEQUENCE: 134

Asp Ala Ser Tyr Arg Tyr Thr
1               5

<210> SEQ ID NO 135
<211> LENGTH: 12
<212> TYPE: PRT
<213> ORGANISM: Artificial Sequence
<220> FEATURE:
<223> OTHER INFORMATION: Modified CDR

<400> SEQUENCE: 135

Gly Phe Thr Phe Ser Thr Ser Gly Met Gly Val Ser
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Modified CDR

<400> SEQUENCE: 136

Gly Phe Thr Leu Ser Thr Ser Gly Met Gly Met Ser
1               5                   10

<210> SEQ ID NO 137
<211> LENGTH: 9
<212> TYPE: PRT
<213> ORGANISM: Artificial Sequence
<220> FEATURE:
<223> OTHER INFORMATION: Modified CDR

<400> SEQUENCE: 137

Gln His Tyr Ser Thr Asp Pro Leu Thr
1               5

<210> SEQ ID NO 138
<211> LENGTH: 12
<212> TYPE: PRT
<213> ORGANISM: Artificial Sequence
<220> FEATURE:
<223> OTHER INFORMATION: Modified CDR

<400> SEQUENCE: 138

Gly Phe Thr Phe Ser Thr Ser Gly Met Gly Met Ser
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Modified CDR

<400> SEQUENCE: 139

Arg Ala Ser Gln Asn Val Gly Ser Asn Val Ala
1               5                   10

<210> SEQ ID NO 140
<211> LENGTH: 18
<212> TYPE: PRT
<213> ORGANISM: Artificial Sequence
<220> FEATURE:
```

<223> OTHER INFORMATION: Modified CDR

<400> SEQUENCE: 140

Leu Ser His Ile Trp Trp Asp Asp Glu Lys Tyr Tyr Val Asp Ser Val
1               5                   10                  15
Lys Gly

<210> SEQ ID NO 141
<211> LENGTH: 18
<212> TYPE: PRT
<213> ORGANISM: Artificial Sequence
<220> FEATURE:
<223> OTHER INFORMATION: Modified CDR

<400> SEQUENCE: 141

Val Ala His Ile Trp Trp Asp Asp Lys Tyr Tyr Val Asp Ser Val
1               5                   10                  15
Lys Gly

<210> SEQ ID NO 142
<211> LENGTH: 9
<212> TYPE: PRT
<213> ORGANISM: Artificial Sequence
<220> FEATURE:
<223> OTHER INFORMATION: Modified CDR

<400> SEQUENCE: 142

Thr Thr Arg Tyr Phe Pro Phe Ala Tyr
1               5

<210> SEQ ID NO 143
<211> LENGTH: 9
<212> TYPE: PRT
<213> ORGANISM: Artificial Sequence
<220> FEATURE:
<223> OTHER INFORMATION: Modified CDR

<400> SEQUENCE: 143

His Arg Ile Tyr Phe Pro Phe Ala Tyr
1               5

<210> SEQ ID NO 144
<211> LENGTH: 12
<212> TYPE: PRT
<213> ORGANISM: Artificial Sequence
<220> FEATURE:
<223> OTHER INFORMATION: Modified CDR

<400> SEQUENCE: 144

Gly Phe Ser Leu Ser Thr Ser Ser Met Gly Met Gly
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Modified CDR

<400> SEQUENCE: 145

Arg Ala Ser Gln Asn Val Gly Thr Asn Val Ala
1               5                   10

<210> SEQ ID NO 146
<211> LENGTH: 7

```
<212> TYPE: PRT
<213> ORGANISM: Artificial Sequence
<220> FEATURE:
<223> OTHER INFORMATION: Modified CDR

<400> SEQUENCE: 146

Asn Ala Ser Asn Arg Ala Ser
1               5

<210> SEQ ID NO 147
<211> LENGTH: 7
<212> TYPE: PRT
<213> ORGANISM: Artificial Sequence
<220> FEATURE:
<223> OTHER INFORMATION: Modified CDR

<400> SEQUENCE: 147

Ser Ala Tyr Tyr Arg Ala Thr
1               5

<210> SEQ ID NO 148
<211> LENGTH: 9
<212> TYPE: PRT
<213> ORGANISM: Artificial Sequence
<220> FEATURE:
<223> OTHER INFORMATION: Modified CDR

<400> SEQUENCE: 148

Gln Gln Tyr Ser Thr Leu Pro Leu Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Modified CDR

<400> SEQUENCE: 149

Ser Arg Leu Tyr Phe Pro Phe Ala Tyr
1               5

<210> SEQ ID NO 150
<211> LENGTH: 12
<212> TYPE: PRT
<213> ORGANISM: Artificial Sequence
<220> FEATURE:
<223> OTHER INFORMATION: Modified CDR

<400> SEQUENCE: 150

Gly Phe Thr Leu Ser Thr Ser Gly Met Gly Val Ser
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Modified CDR

<400> SEQUENCE: 151

Gln Gln His Asn Asn Asp Pro Leu Thr
1               5

<210> SEQ ID NO 152
<211> LENGTH: 7
<212> TYPE: PRT
```

```
<213> ORGANISM: Artificial Sequence
<220> FEATURE:
<223> OTHER INFORMATION: Modified CDR

<400> SEQUENCE: 152

Phe Ala Ser Asn Arg Ala Thr
1               5

<210> SEQ ID NO 153
<211> LENGTH: 12
<212> TYPE: PRT
<213> ORGANISM: Artificial Sequence
<220> FEATURE:
<223> OTHER INFORMATION: Modified CDR

<400> SEQUENCE: 153

Gly Phe Thr Leu Ser Thr Ser Gly Tyr Gly Val Ser
1               5                   10

<210> SEQ ID NO 154
<211> LENGTH: 18
<212> TYPE: PRT
<213> ORGANISM: Artificial Sequence
<220> FEATURE:
<223> OTHER INFORMATION: Modified

<400> SEQUENCE: 154

Val Ala His Val Trp Trp Asp Asp Glu Lys Tyr Tyr Val Asp Ser Val
1               5                   10                  15

Lys Gly

<210> SEQ ID NO 155
<211> LENGTH: 7
<212> TYPE: PRT
<213> ORGANISM: Artificial Sequence
<220> FEATURE:
<223> OTHER INFORMATION: Modified CDR

<400> SEQUENCE: 155

Ser Ala Ser Tyr Arg Asp Thr
1               5

<210> SEQ ID NO 156
<211> LENGTH: 12
<212> TYPE: PRT
<213> ORGANISM: Artificial Sequence
<220> FEATURE:
<223> OTHER INFORMATION: Modified CDR

<400> SEQUENCE: 156

Gly Phe Ser Leu Ser Thr Ser Gly Phe Gly Met Ser
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Modified CDR

<400> SEQUENCE: 157

Thr Val Arg Tyr Phe Pro Phe Ala Tyr
1               5

<210> SEQ ID NO 158
<211> LENGTH: 9
```

```
<212> TYPE: PRT
<213> ORGANISM: Artificial Sequence
<220> FEATURE:
<223> OTHER INFORMATION: Modified CDR

<400> SEQUENCE: 158

Thr Arg Arg Tyr Tyr Pro Phe Ala Tyr
1               5

<210> SEQ ID NO 159
<211> LENGTH: 9
<212> TYPE: PRT
<213> ORGANISM: Artificial Sequence
<220> FEATURE:
<223> OTHER INFORMATION: Modified CDR

<400> SEQUENCE: 159

Gln Gln Tyr Ser Thr Ser Pro Leu Thr
1               5

<210> SEQ ID NO 160
<211> LENGTH: 12
<212> TYPE: PRT
<213> ORGANISM: Artificial Sequence
<220> FEATURE:
<223> OTHER INFORMATION: Modified CDR

<400> SEQUENCE: 160

Gly Phe Ser Leu Ser Thr Ser Gly Phe Gly Val Ser
1               5                   10

<210> SEQ ID NO 161
<211> LENGTH: 9
<212> TYPE: PRT
<213> ORGANISM: Artificial Sequence
<220> FEATURE:
<223> OTHER INFORMATION: Modified CDR

<400> SEQUENCE: 161

Asn Arg Leu Tyr Phe Pro Phe Ala Tyr
1               5

<210> SEQ ID NO 162
<211> LENGTH: 12
<212> TYPE: PRT
<213> ORGANISM: Artificial Sequence
<220> FEATURE:
<223> OTHER INFORMATION: Modified CDR

<400> SEQUENCE: 162

Gly Phe Ser Leu Ser Thr Ser Ser Leu Gly Met Ser
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Modified CDR

<400> SEQUENCE: 163

Gly Phe Thr Leu Ser Thr Ser Gly Met Gly Val Gly
1               5                   10

<210> SEQ ID NO 164
<211> LENGTH: 11
<212> TYPE: PRT
```

```
<213> ORGANISM: Artificial Sequence
<220> FEATURE:
<223> OTHER INFORMATION: Modified CDR

<400> SEQUENCE: 164

Arg Ala Ser Gln Asn Val Ser Thr Asn Val Ala
1               5                   10

<210> SEQ ID NO 165
<211> LENGTH: 9
<212> TYPE: PRT
<213> ORGANISM: Artificial Sequence
<220> FEATURE:
<223> OTHER INFORMATION: Modified CDR

<400> SEQUENCE: 165

Gln Gln Tyr Asn Asn Val Pro Leu Thr
1               5

<210> SEQ ID NO 166
<211> LENGTH: 18
<212> TYPE: PRT
<213> ORGANISM: Artificial Sequence
<220> FEATURE:
<223> OTHER INFORMATION: Modified CDR

<400> SEQUENCE: 166

Val Ala His Ile Trp Trp Glu Asp Glu Lys Tyr Tyr Val Asp Ser Val
1               5                   10                  15

Lys Gly

<210> SEQ ID NO 167
<211> LENGTH: 11
<212> TYPE: PRT
<213> ORGANISM: Artificial Sequence
<220> FEATURE:
<223> OTHER INFORMATION: Modified CDR

<400> SEQUENCE: 167

Arg Ala Ser Gln Asn Val Gly Asn Asn Val Ala
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Modified CDR

<400> SEQUENCE: 168

Gln Gln Tyr Ser Thr Glu Pro Leu Thr
1               5

<210> SEQ ID NO 169
<211> LENGTH: 9
<212> TYPE: PRT
<213> ORGANISM: Artificial Sequence
<220> FEATURE:
<223> OTHER INFORMATION: Modified CDR

<400> SEQUENCE: 169

Gln Gln Tyr Arg Thr Asp Pro Leu Thr
1               5

<210> SEQ ID NO 170
<211> LENGTH: 9
```

```
<212> TYPE: PRT
<213> ORGANISM: Artificial Sequence
<220> FEATURE:
<223> OTHER INFORMATION: Modified CDR

<400> SEQUENCE: 170

Gln Gln His Asn Lys Asp Pro Leu Thr
1               5

<210> SEQ ID NO 171
<211> LENGTH: 11
<212> TYPE: PRT
<213> ORGANISM: Artificial Sequence
<220> FEATURE:
<223> OTHER INFORMATION: Modified CDR

<400> SEQUENCE: 171

Arg Thr Ser Gln Asn Val Gly Thr Tyr Val Ala
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Modified CDR

<400> SEQUENCE: 172

Leu Ala Ser Asn Arg Val Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Modified CDR
<220> FEATURE:
<221> NAME/KEY: VARIANT
<222> LOCATION: (5)..(5)
<223> OTHER INFORMATION: Xaa is Thr or Asn

<400> SEQUENCE: 173

Gln Gln Tyr Ser Xaa Asp Pro Leu Thr
1               5

<210> SEQ ID NO 174
<211> LENGTH: 11
<212> TYPE: PRT
<213> ORGANISM: Artificial Sequence
<220> FEATURE:
<223> OTHER INFORMATION: CDR
<220> FEATURE:
<221> NAME/KEY: VARIANT
<222> LOCATION: (2)..(2)
<223> OTHER INFORMATION: Xaa is Ala or Thr
<220> FEATURE:
<221> NAME/KEY: VARIANT
<222> LOCATION: (5)..(5)
<223> OTHER INFORMATION: Xaa is Asn, Asp or Ser
<220> FEATURE:
<221> NAME/KEY: VARIANT
<222> LOCATION: (7)..(7)
<223> OTHER INFORMATION: Xaa is Gly or Ser
<220> FEATURE:
<221> NAME/KEY: VARIANT
<222> LOCATION: (8)..(8)
<223> OTHER INFORMATION: Xaa is Thr, Ser or Asn
<220> FEATURE:
<221> NAME/KEY: VARIANT
<222> LOCATION: (9)..(9)
```

```
<223> OTHER INFORMATION: Xaa is Asn or Tyr
<220> FEATURE:
<221> NAME/KEY: VARIANT
<222> LOCATION: (1)..(1)0
<223> OTHER INFORMATION: Xaa is Val or Leu

<400> SEQUENCE: 174

Arg Xaa Ser Gln Xaa Val Xaa Xaa Xaa Xaa Ala
1               5                   10
```